US009816107B2

(12) United States Patent
Geisler et al.

(10) Patent No.: US 9,816,107 B2
(45) Date of Patent: *Nov. 14, 2017

(54) TRANSGENIC INSECT CELLS COMPRISING A BACTERIAL GLCNAC-6-P 2'-EPIMERASE

(71) Applicant: The University of Wyoming, Laramie, WY (US)

(72) Inventors: Christoph Geisler, Laramie, WY (US); Donald Jarvis, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 61 days.

This patent is subject to a terminal disclaimer.

(21) Appl. No.: 13/827,546

(22) Filed: Mar. 14, 2013

(65) Prior Publication Data

US 2014/0283154 A1    Sep. 18, 2014

Related U.S. Application Data

(62) Division of application No. 13/559,912, filed on Jul. 27, 2012, now Pat. No. 8,846,373.

(60) Provisional application No. 61/513,254, filed on Jul. 29, 2011.

(51) Int. Cl.
*A01K 67/00* (2006.01)
*C12N 15/85* (2006.01)
*A01K 67/033* (2006.01)
*C12N 15/86* (2006.01)

(52) U.S. Cl.
CPC .......... *C12N 15/85* (2013.01); *A01K 67/0339* (2013.01); *C12N 15/86* (2013.01); *C12N 2710/14043* (2013.01)

(58) Field of Classification Search
CPC ..................................................... C12N 15/85
USPC .......................................................... 800/8
See application file for complete search history.

(56) References Cited

U.S. PATENT DOCUMENTS

| | | |
|---|---|---|
| 6,949,372 B2 | 9/2005 | Betenbaugh |
| 7,776,565 B2 | 8/2010 | Betenbaugh |
| 7,781,647 B2 | 8/2010 | Bakker |
| 7,863,020 B2 | 1/2011 | Hamilton, Sr. |
| 2007/0067855 A1 | 3/2007 | Jarvis |
| 2008/0145899 A1 | 6/2008 | Johnson |
| 2009/0226968 A1 | 9/2009 | Betenbaugh et al. |
| 2010/0186099 A1 | 7/2010 | Fraser |
| 2010/0279356 A1 | 11/2010 | Hamilton |
| 2011/0014661 A1 | 1/2011 | Samain |
| 2011/0165626 A1 | 7/2011 | Samain |
| 2011/0207179 A1 | 8/2011 | Noguchi |

FOREIGN PATENT DOCUMENTS

CA WO 2011/130836 A1 * 10/2011 ............. C12P 19/32
EP      1541693 A1     6/2005

OTHER PUBLICATIONS

Hollister et al. (1998, Glycobiology, vol. 8(5), pp. 473-480).*
Devos et al., Proteins: Structure, Function and Genetics, 2000, vol. 41, pp. 98-107.*
Atkinson et al., 2001, Annu., Rev. Entomol., vol. 46, pp. 317-346.*
Spradling et al., 1982, Science, vol. 218, pp. 341-347.*
Nitasaka et al., PNAS, 1987, vol. 84, pp. 7605-7608.*
O'Brochta et al., 2003, J. Exp. Biol., vol. 206, pp. 3823-3834.*
Franz et al. (2009, Insect Mol. Biol., vol. 18(5), pp. 661-672).*
Seppala, R., Lehto, V.-P., Gahl, W. A., 1999. Mutations in the human UDP-Nacetylglucosamine 2-epimerase gene define the disease sialuria and the allosteric site of the enzyme. The American Journal of Human Genetics. 64, 1563-1569.
Wen, D. X. E. C. Svensson, et al. (1992) Tissue-specific alternative splicing of the B-galactoside a2,6-sialyltransferase gene. J Biol Chem, 267(4): 2512-2518.
Seal R.L., Gordon S.M., Lush M.J., Wright M.W., Bruford E.A., (Jan. 2011) genenames.org: the HGNC resources in 2011. Nucleic Acids Res. 39(Database issue): D519-9. PMID:20929869 PMCID:PMC3013772 (Nucleic Acids Research Advance Access published Oct. 6, 2010, Nucleic Acids Research, 2010, 1-6 doi:10.1093/nar/gkq892).
Vann W.F., Daines D.A., Murkin A.S., Tanner M.E., Chaffin D.O., Rubens C.E., Vionnet J., Silver R.P. (Feb. 2004) The NeuC Protein of *Escherichia coli* K1 Is a UDP N-Acetylglucosamine 2-Epimerase. J Bacteriol 186(3): 706-712. doi: 10.1128/JB.186.3.706-712.2004 PMCID: PMC321479.
Broun et al., Catalytic plasticity of fatty acid modification enzymes underlying chemical diversity of plant lipids. Science 1998, vol. 282: 1315-1317.
Chica et al., Semi-rational approaches to engineering enzyme activity: combining the benefits of directed evolution and rational design. Curr. Opi. Biotechnol. 2005, vol. 16: 378-384.

(Continued)

*Primary Examiner* — Thaian N Ton
*Assistant Examiner* — David A Montanari
(74) *Attorney, Agent, or Firm* — The Intellectual Property Law Office of Verne A. Luckow, LLC

(57) ABSTRACT

The present invention relates to methods of facilitating the expression of recombinant polypeptides from cells, extracellular fluids, extracellular fibers, or any combination thereof, obtained from transgenic insect cells and larvae comprising a bacterial GlcNAc-6-P 2'-epimerase (GNPE), which is capable of converting N-acetyl-D-glucosamine-6-phosphate (GlcNAc-6-P) to N-acetyl-D-mannosamine-6-phosphate (ManNAc-6-P). The invention relates to methods to promote efficient glycoconjugate sialylation, by providing simpler ways to produce large intracellular pools of sialic acid precursors. The invention is also directed to nucleic acids, vectors, and cells comprising nucleic acids encoding polypeptides involved in the synthesis of sialic acid precursors, and cells in combination with nucleic acids encoding glycosyltransferases, including sialyltransferases, to facilitate the production of humanized recombinant glycoproteins. The engineered cells can be used to produce glycosylated proteins lepidopteran insects and cultured cell lines derived from *Spodoptera frugiperda, Trichoplusia ni*, and silkworms, such as *Bombyx mori*, particularly those that can be infected by baculovirus expression vectors.

33 Claims, 22 Drawing Sheets

(56) References Cited

OTHER PUBLICATIONS

Devos et al. Practical limits of function prediction. Proteins: Structure, Function, and Genetics. 2000, vol. 41: 98-107.
Durfee et al.. The complete genome sequence of Escherichia coli DH10B: insights into the biology of a laboratory workhorse. J Bacteriol., 2008, vol. 190(7): 2597-2606.
Kimchi-Sarfaty et al., A "Silent" polymorphism in the MDR1 gene changes substrate specificity. Science, 2007, vol. 315: 525-528.
Kisselev L., Polypeptide release factors in prokaryotes and eukaryotes: same function, different structure. Structure, 2002, vol. 10: 8-9.
Nackley et al., Human Catechol-O-Methyltransferase haplotypes modulate protein expression by altering mRNA secondary structure. Science, 2006, vol. 314: 1930-1933.
Sauna et al., Silent polymorphisms speak: How they affect pharmacogenomics and the treatment of cancer. Cancer Res., 2007, vol. 67(20): 9609-9612.
Seffernick et al., Melamine deaminase and Atrazine chlorohydrolase: 98 percent identical but functionally different. J Bacteriol., 2001, vol. 183(8): 2405-2410.
Sen et al., Developments in directed evolution from protein sequence. Appl. Biochem. Biotechnol. 2007, vol. 143: 212-223.
Whisstock et al., Prediction of protein function from protein sequence. Q. Rev. Biophysics., 2003, vol. 36(3): 307-340.
Whishart et al., A single mutation converts a novel phosphotyrosine binding domain into a dual-specificity phosphatase. J. Biol. Chem. 1995, vol. 270(45): 26782-26785.
Witkowski et al., Conversion of b-ketoacyl synthase to a Malonyl Decarboxylase by replacement of the active cysteine with glutamine. Biochemistry, 1999, vol. 38: 11643-11650.
Kalivoda, KA, Steenbergen, SM, Vimr, ER, Plumbridge, J (2003) Regulations of Sialic Acid Catabolism by the DNA Binding Protein NanR in Escherichia coli. J. Bacteriol. 185(16): 4806-4815.
Ghosh, S. et al., The sialic acids V. N-Acyl-D-glucosamine 2-epimerase Journal of Bacterial Chemistry, Apr. 1965, vol. 240, No. 4, pp. 1531-1536. See p. 1531, col. 1, paragraph 1.
Swartley, J. S. et a!. , 'Identification of a genetic locus involved in the biosynthesis of N-Acetyl-D-Mannosamine, a precursor of the (a2->8)-Linked polysialic acid capsule of serogroup B Neisseria meningitidis', Journal of Bacteriology, Mar. 1994, vol. 176, No. 5, pp. 1530-1534. See p. 1532, col. 2, paragraph 3; p. 1533, col. 1, paragraph 2.
Rodriguez-Aparicio, L. B. et al., 'Determination of different amino sugar 2'-epimerase activities by coupling to N-acetylneuraminate synthesis', Biochimica et Biophysica Acta, Aug. 5, 1999, vol. 1428, No. 2-3, pp. 305-313. See abstract; p. 311, paragraphs 1 and 2.
Ferrero, M. A. eta!., 'Purification and characterization of GlcNAc-6-P 2-epimerase from Escherichia coli K92', Acta Biochimica Polonica, Jun. 2007, vol. 54, No. 2, pp. 387-399. See abstract.
Lee, Yen-Chung et al., 'Production of N-acetyl-D-neuraminic acid by recombinant whole cells expressing Anabaena sp. CH1 N-acetyl-D-glucosa• mine 2-epimerase and Escherichia coli N-acetyl-D-neuraminic acid lyase', Journal of Biotechnology, May 2007, vol. 129, No. 3, pp. 453-460. See the whole document.
Zhang, Yinan et al., 'An efficient method for N-acetyl-D-neuraminic acid production using coupled bacterial cells with a safe temperature-induced system', Appl. Microbial. Biotechnol., Mar. 2010, vol. 86, No. 2, pp. 481-489. See the whole document.
Kiser, Kevin B. et al., 'Staphylococcus aureus cap5P encodes a UDP-NAcetyl• glucosamine 2-epimerase with functional redundancy', Journal of Bacteriology, Aug. 1999, vol. 181, No. 16, pp. 4818-4824. See the whole document.
Xu, Xiaoman et al., 'Production of N-Acetyl-D-Neuraminic acid by use of an efficient spore surface display system', Applied and Environmental Microbiology, May 2011, vol. 77, No. 10, pp. 3197-3201. See the whole document.
Luchansky, Sara J. et al., 'GlcNAc 2-epimerase can serve a catabolic role in sialic acid metabolism', The Journal of Biological Chemistry, Mar. 7, 2003, vol. 278, No. 10, pp. 8035-8042. See the whole document.
PCT International Search Report for International Application No. PCT/US2012/048564, International Filing Date Jul. 27, 2012.
Aumiller, J.J., Mabashi-Asazuma, H., Hillar, A., Shi, X., Jarvis, D. L., 2012. A new glycoengineered insect cell line with an inducibly mammalianized protein N-glycosylation pathway. Glycobiology. 22, 417-428.
Aumiller, J.J., Hollister, J.R., and Jarvis, D.L. (2003) A transgenic lepidopteran insect cell line engineered to produce CMP-sialic acid and sialoglycoproteins. Glycobiology, 13: 497-507.
Blattner FR, Plunkett G III, Bloch CA, Perna NT, Burland V, Riley M, Collado-Vides J, Glasner JD, Rode CK, Mayhew GF, Gregor J, Davis NW, Kirkpatrick HA, Goeden MA, Rose DJ, Mau B, Shao Y (1997). The complete genome sequence of Escherichia coli K-12. Science, 277: 1453-1474.
Bork, K., Reutter, W., Gerardy-Schahn, R., Horstkorte, R., 2005. The intracellular concentration of sialic acid regulates the polysialylation of the neural cell adhesion molecule. FEBS Lett. 579, 5079-5083.
Bork, K., Reutter, W., Weidemann, W., Horstkorte, R., 2007. Enhanced sialylation of EPO by overexpression of UDP-GlcNAc 2-epimerase/ManAc kinase containing a sialuria mutation in CHO cells. FEBS Lett. 581, 4195-4198.
Castilho, A., Strasser, R., Stadlmann, J., Grass, J., Jez, J. Gattinger, P., Kunert, R., Quendler, H., Pabst, M., Leonard, R, Altmann, F. and H. Steinkellner (2010) In planta protein sialylation through overexpression of the respective mammalian pathway. J Biol Chem, 285: 15923-15930.
Chang, K. H., J. M. Yang, et al. (2005) Enhanced activity of recombinant beta-secretase from Drosophila melanogaster S2 cells transformed with cDNAs encoding human beta1,4-galactosyltransferase and Gal beta1,4-GlcNAc alpha2,6-sialyltransferase. J Biotechnol, 116(4): 359-367.
Chung, C. H., Mirakhur, B., Chan, E., Le, Q.-T., Berlin, J., Morse, M., Murphy, B. A., Satinover, S. M., Hosen, J., Mauro, D., Slebos, R. J., Zhou, Q., Gold, D., Hatley, T., Hicklin, D. J., Platts-Mills, T. A. E., 2008. Cetuximab-induced anaphylaxis and IgE specific for galactose-α-1,3-galactose. New England Journal of Medicine. 358, 1109-1117.
Fierfort and Samain, (2008) Genetic Engineering of Escherichia coli for the economical production of sialylated oligosaccharides. J Biotechnol, 134:261-265.
Geisler, C., Jarvis, D. L., 2009. Insect cell glycosylation patterns in the context of biopharmaceuticals. In: Walsh, G. (Ed.), Post-translational modifications in the context of biopharmaceuticals. Wiley-VCH, Weinheim, pp. 165-191.
Geisler, C., Jarvis, D. L., 2011. Letter to the Glyco-Forum: Effective glycoanalysis with Maackia amurensis lectins requires a clear understanding of their binding specificities. Glycobiology. 21, 988-993.
Ghaderi, D., Taylor, R. E., Padler-Karavani, V., Diaz, S., Varki, A., 2010. Implications of the presence of N-glycolylneuraminic acid in recombinant therapeutic glycoproteins. Nat Biotech. 28, 863-867.
Ghosh, S. and S. Roseman (1965) The Sialic Acids IV. N-acyl-D-glucosamine 6-phosphate 2-epimerase. J Biol Chem, 240(4): 1525-1530.
Gritz and Davis (1983) Plasmid-encoded hygromycin B resistance: the sequence of hygromycin B phosphotransferase gene and its expression in Escherichia coli and Saccharomyces cerevisiae. Gene, 25 (2-3):179-188.
Hamilton, S. R., Davidson, R. C., Sethuraman, N., Nett, J. H., Jiang, Y., Rios, S., Bobrowicz, P., Stadheim, T. A., Li, H., Choi, B. K., Hopkins, D., Wischnewski, H., Roser, J., Mitchell, T., Strawbridge, R. R., Hoopes, J., Wildt, S., Gerngross, T. U., (2006) Humanization of yeast to produce complex terminally sialylated glycoproteins. Science, 313(5792): 1441-1443.
Harrison, R. L., Jarvis, D. L., 2006. Protein N-glycosylation in the baculovirus-insect cell expression system and engineering of insect cells to produce "mammalianized" recombinant glycoproteins. Adv Virus Res. 68, 159-191.
Harrison, R. L., Jarvis, D. L., 2007a. Transforming lepidopteran insect cells for continuous recombinant protein expression. Methods in Molecular Biology. 388, 299-316.

(56) References Cited

OTHER PUBLICATIONS

Harrison, R. L., Jarvis, D. L., 2007b. Transforming lepidopteran insect cells for improved protein processing. Methods Mol. Biol. 388, 341-356.
Hill, D. R., Aumiller, J. J., Shi, X., Jarvis, D. L., (2006) Isolation and analysis of a baculovirus vector that supports recombinant glycoprotein sialylation by SfSWT-1 cells cultured in serum-free medium. Biotechnol Bioeng, 95(1): 37-47.
Hinderlich, S., M. Berger, et al. (2001) Biosynthesis of N-acetylneuraminic acid in cells lacking UDP-N-acetylglucosamine 2-epimerase/N-acetylmannosamine kinase. Biol Chem, 382(2): 291-297.
Hinderlich, S., Stäsche, R., Zeitler, R., Reutter, W., 1997. A bifunctional enzyme catalyzes the first two steps in N-acetylneuraminic acid biosynthesis of rat liver—Purification and characterization of UDP-N-acetylglucosamine 2-epimerase/N-acetylmannosamine kinase. Journal of Biological Chemistry. 272, 24313-24318.
Hollister, J. and D. L. Jarvis (2001) Engineering lepidopteran insect cells for sialoglycoprotein production by genetic transformation with mammalian beta 1,4-galactosyltransferase and alpha 2,6-sialyltransferase genes. Glycobiology, 11: 1-9.
Hollister, J. R., Grabenhorst, E., Nimtz, M., Conradt, H., Jarvis, D. L., (2002) Engineering the protein N-glycosylation pathway in insect cells for production of biantennary, complex N-glycans. Biochemistry, 41: 15093-15104.
Hollister, J.R., Shaper, J.H., and Jarvis, D.L. (1998) Stable expression of mammalian B1,4 galactosyltransferase extends the N-glycosylation pathway in insect cells. Glycobiology, 8:473-480.
Hooker, A. D., Green, N. H., Baines, A. J., Bull, A. T., Jenkins, N., Strange, P. G., James, D. C., 1999. Constraints on the transport and glycosylation of recombinant IFN-.gamma. in Chinese hamster ovary and insect cells. Biotechnol Bioeng. 63, 559-572.
Ishida, N, Ito, M, Yoshioka, S, Sun-Wada, G-H and Kawakita, M (1998) Functional expression of human Golgi CMP-sialic acid transporter in the Golgi complex of a transporter-deficient Chinese hamster ovary cell mutant. J Biochem, 124(1): 171-178.
Jarvis, D. L., 2009. Baculovirus—insect cell expression systems. In: Richard, R. B., Murray, P. D. (Eds.), Methods in Enzymology, vol. 463. Academic Press, pp. 191-222.
Jarvis, D. L., C. Weinkauf, et al. (1996) Immediate-early baculovirus vectors for foreign gene expression in transformed or infected insect cells. Protein Expr Purif, 8(2): 191-203.
Jarvis, D. L., Finn, E. E., 1996. Modifying the insect cell N-glycosylation pathway with immediate early baculovirus expression vectors. Nature Biotechnology. 14, 1288-1292.
Jarvis, D. L., Fleming, J. A., Kovacs, G. R., Summers, M. D., Guarino, L. A., 1990. Use of early baculovirus promoters for continuous expression and efficient processing of foreign gene products in stably transformed lepidopteran cells. Nature Biotechnology. 8, 950-955.
Jarvis, D. L., Howe, D., Aumiller, J. J., 2001. Novel baculovirus expression vectors that provide sialylation of recombinant glycoproteins in lepidopteran insect cells. Journal of Virology. 75, 6223-6227.
Jin Q, Yuan Z, Xu J, Wang Y, Shen Y, Lu W, Wang J, Liu H, Yang J, Yang F, Zhang X, Zhang J, Yang G, Wu H, Qu D, Dong J, Sun L, Xue Y, Zhao A, Gao Y, Zhu J, Kan B, Ding K, Chen S, Cheng H, Yao Z, He B, Chen R, Ma D, Qiang B, Wen Y, Hou Y, Yu J (2002) Genome sequence of Shigella flexneri 2a: insights into pathogenicity through comparison with genomes of Escherichia coli K12 and O157. Nucleic Acids Res, 30: 4432-4441.
Jones, M. B., Teng, H., Rhee, J. K., Lahar, N., Baskaran, G., Yarema, K. J., 2004. Characterization of the cellular uptake and metabolic conversion of acetylated Nacetylmannosamine (Man-NAc) analogues to sialic acids. Biotechnology and Bioengineering. 85, 394-405.
Lawrence, S. M., K. A. Huddleston, et al. (2000) Cloning and expression of the human N-acetylneuraminic acid phosphate synthase gene with 2-keto-3-deoxy-D-glycero-D-galacto-nononic acid biosynthetic ability. J Biol Chem, 275(23): 17869-77.

Leary, J. J., Brigati, D. J., Ward, D. C., 1983. Rapid and sensitive colorimetric method for visualizing biotin-labeled DNA probes hybridized to DNA or RNA immobilized on nitrocellulose: Bio-blots. Proc Natl Acad Sci U S A. 80, 4045-4049.
Marchal, I., Jarvis, D. L., Cacan, R., Verbert, A., 2001. Glycoproteins from insect cells: sialylated or not? Biol. Chem. 382, 151-159.
März, L., Altmann, F., Staudacher, E., Kubelka, V., 1995. Protein glycosylation in insects. In: Montreuil, J., Vliegenthart, J. F. G., Schachter, H. (Eds.), Glycoproteins, vol. 29a. Elsevier, Amsterdam, pp. 543-563.
Morell, A. G., G. Gregoriadis, et al. (1971) The role of sialic acid in determining the survival of glycoproteins in the circulation. J Biol Chem, 246(5): 1461-1467.
Münster, A. K., M. Eckhardt, et al. (1998) Mammalian cytidine 5'-monophosphate N-acetylneuraminic acid synthetase: a nuclear protein with evolutionarily conserved structural motifs. Proc Natl Acad Sci U S A, 95(16): 9140-9145.
Nakata, D., B. E. Close, et al. (2000) Molecular cloning and expression of the mouse N-acetylneuraminic acid 9-phosphate synthase which does not have deaminoneuraminic acid (KDN) 9-phosphate synthase activity. Biochem Biophys Res Commun, 273(2): 642-648.
Ngantung, F. A. Miller, P. G., Brushett, F. R., Tang, G. L., Wang, D. I., (2006) RNA interference of sialidase improves glycoprotein sialic acid content consistency. Biotechnol Bioeng, 95(1): 106-19.
O'Reilly, D. R., Miller, L. K., and Luckow, V. A. (1992) Baculovirus expression vectors. W.H. Freeman and Company, New York.
Perna NT, Plunkett G III, Burland V, Mau B, Glasner JD, Rose DJ, Mayhew GF, Evans PS, Gregor J, Kirkpatrick HA, Posfai G, Hackett J, Klink S, Boutin A, Shao Y, Miller L, Grotbeck EJ, Davis NW, Lim A, Dimalanta ET, Potamousis KD, Apodaca J, Anantharaman TS, Lin J, Yen G, Schwartz DC, Welch RA, Blattner FR (2001) Genome sequence of enterohaemorrhagic Escherichia coli O157:H7. Nature, 409: 529-533.
Plumbridge, J. and E. Vimr (1999) Convergent pathways for utilization of the amino sugars N-acetylglucosamine, N-acetylmannosamine, and N-acetylneuraminic acid by Escherichia coli. J Bacteriol, 181(1): 47-54.
Riley M, Abe T, Arnaud MB, Berlyn MK, Blattner FR, Chaudhuri RR, Glasner JD, Horiuchi T, Keseler IM, Kosuge T, Mori H, Perna NT, Plunkett G, Rudd KE, Serres MH, Thomas GH, Thomson NR, Wishart D, Wanner BL (2006) Escherichia coli K-12: a cooperatively developed annotation snapshot-2005. Nucleic Acids Res, 34: 1-9.
Ringenberg, M. A., Steenbergen, S. M., Vimr, E. R., (2003) The first committed step in the biosynthesis of sialic acid by Escherichia coli K1 does not involve a phosphorylated N-acetylmannosamine intermediate. Mol Microbiol, 50(3): 961-75.
Russo, RN, Shaper, NL, and Shaper, JH (1990) Bovine beta 1->-4-galactosyltransferase: two sets of mRNA transcripts encode two forms of the protein with different amino-terminal domains. In vitro translation experiments demonstrate that both the short and the long forms of the enzyme are type II membrane-bound glycoproteins. J Biol Chem, 265: 3324-3331.
Sambrook, J., Fritsch, E. F., Maniatis, T., 1989. Molecular cloning: a laboratory manual (2nd edition). Cold Spring Harbor Laboratory Press, Cold Spring Harbor, NY.
Sasai, K., Ikeda, Y., Fujii, T., Tsuda, T., Taniguchi, N., (2002) UDP-GlcNAc concentration is an important factor in the biosynthesis of beta1,6-branched oligosaccharides: regulation based on the kinetic properties of N-acetylglucosaminyltransferase V. Glycobiology, 12(2): 119-127.
Sasaki, K., E. Watanabe, et al. (1993). Expression cloning of a novel Gal B(1-3/1-4) GlcNAc a2,3-sialyltransferase using lectin resistance selection. J Biol Chem, 268(30): 22782-22787.
IDS Ref 87: Schnoes AM, Brown SD, Dodeveski, Babbitt PC (2009) Annotation Error in Public Databases: Misannotation of Molecular Function in Enzyme Superfamilies. PLoS Comput Biol 5(12): e1000605. doi: 10.1371/journal.pcbi.1000605.

(56) References Cited

OTHER PUBLICATIONS

IDS Ref 88: Zhang et al. An efficient method for N-acetyl-D-neuraminic acid production using coupled bacterial cells with a safe temperature-induced system. Appl Microbiol Blotechnol., 2010, vol. 86: 481-489.
Schachter, H. (2000) The joys of HexNAc. The synthesis and function of N- and O-glycan branches. Glycoconj J, 17(7-9): 465-83.
Seo, N. S., Hollister, J. R., Jarvis, D. L., 2001. Mammalian glycosyltransferase expression allows sialoglycoprotein production by baculovirus-infected insect cells. Protein Expression and Purification. 22, 234-241.
Seppala, R., Lento, V.-P., Gahl, W. A., 1999. Mutations in the human UDP-Nacetylglucosamine 2-epimerase gene define the disease sialuria and the allosteric site of the enzyme. The American Journal of Human Genetics. 64, 1563-1569.
Shaper, N. L., J. H. Shaper, et al. (1986) Bovine galactosyltransferase: identification of a clone by direct immunological screening of a cDNA expression library. Proc Natl Acad Sci U S A, 83(6): 1573-1577.
Shi, X., Jarvis, D. L., 2007. Protein N-glycosylation in the baculovirus-insect cell system. Curr Drug Targets. 8, 1116-1125.
Son, Y. D., Jeong, Y. T., Park, S. Y., Kim, J. H., 2011. Enhanced sialylation of recombinant human erythropoietin in Chinese hamster ovary cells by combinatorial engineering of selected genes. Glycobiology. 21, 1019-1028.
Son, Y-D, Jeong, YT Park, S-Y and Kim, JH, 2011. Enhanced sialylation of recombinant human erythropoietin in Chinese hamster ovary cells by combinatorial engineering of selected genes. Glycobiology 21(8) 1019-1028.
Stäsche, R., Hinderlich, S., Weise, C., Effertz, K., Lucka, L., Moormann, P., Reutter, W., 1997. A bifunctional enzyme catalyzes the first two steps in N-acetylneuraminic acid biosynthesis of rat liver. Molecular cloning and functional expression of UDP-N-acetyl-glucosamine 2-epimerase/N-acetylmannosamine kinase. J Biol Chem. 272, 24319-24324.
Summers, M. D., Smith, G. E., A manual of methods for baculovirus vectors and insect cell culture procedures. Texas Agricultural Experiment Station Bulletin. Texas Agricultural Experiment Station, College Station, TX, 1987.
Tan, J., A. F. D'Agostaro, et al. (1995) The human UDP-N-acetylglucosamine: a-6-D-mannoside-B-1,2-N-acetylglucosaminyltransferase II gene (MGAT2). Cloning of genomic DNA, localization to chromosome 14q21, expression in insect cells and purification of the recombinant protein. Eur J Biochem, 231(2): 317-328.
Tao, F., Zhang, Y., Ma, C., Xu, P., 2010. Biotechnological production and applications of N-acetyl-D-neuraminic acid: current state and perspectives. Appl. Microbiol. Biotechnol. 87, 1281-1289.
Thomason LC, Court DL, Datta AR, Khanna R, Rosner JL (2004) Identification of Escherichia coli K12 ybhE gene as pgl, encoding 6-phosphogluconolactonase. J Bacteriol, 186: 8248-8253.

Tomiya, N., Ailor, E., Lawrence, S. M., Betenbaugh, M. J., Lee, Y. C., 2001. Determination of nucleotides and sugar nucleotides involved in protein glycosylation by high-performance anion-exchange chromatography: sugar nucleotide contents in cultured insect cells and mammalian cells. Analytical Biochemistry. 293, 129-137.
Toth, A. M., Geisler, C., Aumiller, J. J., Jarvis, D. L., 2011. Factors affecting recombinant Western equine encephalitis virus glycoprotein production in the baculovirus system. Protein Expr. Purif. 80, 274-282.
Vaughn, J. L., Goodwin, R. H., Tompkins, G. J., McCawley, P., (1977) The establishment of two cell lines from the insect Spodoptera frugiperda (Lepidoptera; Noctuidae). In Vitro, 13(4): 213-217.
Vimr, E. R., Kalivoda, K. A., Deszo, E. L., Steenbergen, S. M., 2004. Diversity of microbial sialic acid metabolism. Microbiol. Mol. Biol. Rev. 68, 132-153.
Viswanathan, K., Narang, S., Hinderlich, S., Lee, Y. C., Betenbaugh, M. J., 2005. Engineering intracellular CMP-sialic acid metabolism into insect cells and methods to enhance its generation. Biochemistry. 44, 7526-7534.
Viswanathan, K., Lawrence, S., Hinderlich, S., Yarema, K. J., Lee, Y. C., Betenbaugh, M. J., (2003) Engineering sialic acid synthetic ability into insect cells: identifying metabolic bottlenecks and devising strategies to overcome them. Biochemistry, 42(51): 15215-15225.
Walsh, G., 2010. Biopharmaceutical benchmarks 2010. Nat Biotech. 28, 917-924.
Walters, DM, Stirewalt, VL, Melville, SB (1999) Cloning, sequence, and transcriptional regulation of the operon encoding a putative N-acetylmannosamine-6-phosphate epimerase (nanE) and sialic acid lyase (nanA) in Clostridium perfringens. J Bacteriol, 181: 4526-4532.
Warren, L., 1959. The thiobarbituric acid assay of sialic acids. J. Biol. Chem. 234, 1971-1975.
Weinstein et al., (1987) Primary structure of beta-galactoside alpha 2,6-sialyltransferase. Conversion of membrane-bound enzyme to soluble forms by cleavage of the NH2-terminal signal anchor. J Biol Chem, 262(36): 17735-17743.
Wen, D. X., E. C. Svensson, et al. (1992) Tissue-specific alternative splicing of the B-galactoside a2,6-sialyltransferase gene. J Biol Chem, 267(4): 2512-2518.
Wickham, T. J., Davis, T., Granados, R. R., Shuler, M. L., Wood, H. A., 1992. Screening of insect cell lines for the production of recombinant proteins and infectious virus in the baculovirus expression system. Biotechnol Prog. 8, 391-396.
Yang F, Yang J, Zhang X, Chen L, Jiang Y, Yan Y, Tang X, Wang J, Xiong Z, Dong J, Xue Y, Zhu Y, Xu X, Sun L, Chen S, Nie H, Peng J, Xu J, Wang Y, Yuan Z, Wen Y, Yao Z, Shen Y, Qiang B, Hou Y, Yu J, Jin Q (2005) Genome dynamics and diversity of Shigella species, the etiologic agents of bacillary dysentery. Nucleic Acids Res, 33: 6445-6458.

\* cited by examiner

Mammalianizing insect N-glycan processing,
Part II: Sialic Acid Biosynthesis and Utilization General Scheme Using Bacterial and Mammalian Genes Encoding Sialic Acid Pathway Enzymes to Facilitate Production of Sialylated Glycoconjugates in Insect Cells

Using a Bacterial Epimerase to Promote Sialylation of Glycoconjugates (Continued)

Using Two Enzymes to Promote Sialylation of Glycocongjugates

GlcNAc → ManNAc [3.1]
[RBP (epimerase activity)]

ManNAc →(↓ + ATP, − ADP ↑)→ ManNAc-6-P [3.2]
[ManNAc Kinase]

GNPE-modified SfSWT-20 and SfSWT-21 Cells Produce Higher Levels of Sialic Acid When Grown in Serum-Free Media Supplemented With GlcNAc

Key Pathways in the Synthesis of CMP-N-acetylneuraminate (CMP-Sialic Acid)

TRANSGENIC INSECT CELLS COMPRISING A BACTERIAL GLCNAC-6-P 2'-EPIMERASE

CROSS REFERENCE TO RELATED APPLICATIONS

The application claims priority under 35 U.S.C. §119(e) to U.S. Provisional Patent Application No. 61/513,254, filed on Jul. 29, 2011, and U.S. Ser. No. 13/559,912, filed on Jul. 27, 2012, the disclosures of which are incorporated herein by reference.

STATEMENT REGARDING FEDERALLY-SPONSORED RESEARCH OR DEVELOPMENT

This invention was made with U.S. Government Support under grant R01GM49734 awarded by the National Institute of General Medical Sciences and U54AI-065357 awarded by the National Institute of Allergy and Infectious Diseases. The U.S. Government has certain rights in the invention.

INCORPORATION-BY-REFERENCE OF A SEQUENCE LISTING

The sequence listing contained in the file "127184_0008_U2_ST25.txt", created on 2013 Mar. 14, modified on 2013 Mar. 14, file size 7,461 bytes, is incorporated by reference in its entirety herein.

FIELD OF THE INVENTION

The present invention relates to new methods to promote sialylation of glycoconjugates, including recombinant glycoproteins, in glycoconjugate production systems. In particular, the invention relates to methods to promote efficient glycoconjugate sialylation in recombinant expression systems, by providing simpler, more economical, and more effective ways to produce large intracellular pools of sialic acid precursors. The invention is directed to nucleic acids, vectors, and cells harboring vectors comprising nucleic acids encoding enzymes involved in the synthesis of sialic acid precursors, and cells harboring these nucleic acids in combination with nucleic acids encoding one or more glycosyltransferases, including sialyltransferases, to facilitate the production of humanized recombinant glycoproteins in bacterial, fungal, plant, and animal cell expression systems. The engineered cells can be used to facilitate the heterologous production of glycosylated proteins in virally-infected, transiently-transformed, or stably-transformed host cells, including lepidopteran insects and cultured cell lines derived from *Spodoptera frugiperda*, *Trichoplusia ni*, and *Bombyx mori*, among others, that can be infected by baculovirus expression vectors.

BACKGROUND OF THE INVENTION

Sialylation is a biosynthetic process that involves the addition of sialic acid residues, N- or O-substituted derivatives of neuraminic acid, to the carbohydrate chains, or glycans, of glycoconjugates. Glycoconjugates are molecules that consist of a carbohydrate moiety covalently linked to another chemical moiety, such as a protein, peptide, or lipid, to form conjugates typically classified as glycoproteins, glycopeptides, peptidoglycans, glycolipids, or lipopolysaccharides. Glycoconjugates are used in many biomedical applications, and sialylation is often required for their activity and optimal use. Many therapeutic glycoproteins need to be sialylated, for example, because the sialic acid moieties prevent rapid clearance of a glycoconjugate from the patient's circulation (Morell et al., 1971; Ngantung et al. 2006). Oligosaccharide side-chains, or glycans, are also known to mediate a variety of other glycoprotein functions, including folding, trafficking, stability, and enzyme activity (Harrison and Jarvis, 2006).

Higher eukaryotic production systems, such as mammalian cells, have all of the biosynthetic components required for sialylation, which can be used to produce sialylated glycoconjugates. Lower eukaryotic systems, such as yeast, plant, and insect systems, can also be used to produce recombinant glycoconjugates, often at a lower cost. Lower eukaryotic systems cannot sialylate newly-synthesized glycoconjugates, however, because they lack one or more components of the biosynthetic systems or complexes required for sialylation. These complexes includes many enzymes, such as glycosyltransferases that produce the glycans used as acceptor substrates, sialyltransferases that transfer sialic acid residues from CMP-sialic acids to the acceptor substrates, and enzymes responsible for the production of CMP-sialic acids, which are the donor substrates for glycoconjugate sialylation.

A variety of studies have shown that the inability of yeast, plant, and insect systems to sialylate newly-synthesized glycoconjugates can be addressed by genetic engineering. Each of these host cell systems can be engineered to introduce genes from other organisms that encode the components needed to sialylate newly-synthesized glycoconjugates (Hollister and Jarvis 2001; Hollister et al., 2002; Aumiller et al., 2003; Chang et al., 2005; Hamilton et al., 2006; and Castilho et al., 2010). All of the glycoengineering approaches designed to promote glycoconjugate sialylation so far have also required supplementation of the cellular growth medium with chemicals, such as a sialic acid precursor. The most commonly used precursor has been N-acetylmannosamine (ManNAc), which is converted to ManNAc-6-phosphate (ManNAc-6-P) by intracellular kinases. The resulting ManNAc-6-P can be converted to free sialic acids, which can then be converted to CMP-sialic acids, which are the donor substrates directly required for glycoconjugate sialylation. Media supplementation has its disadvantages, however, as (1) ManNAc is expensive; (2) its addition to the cellular growth medium is inconvenient and increases the risk of cell culture contamination, and (3) the ManNAc supplementation strategy does not necessarily raise the intracellular CMP-sialic acid concentrations to levels that are sufficient to support efficient glycoconjugate sialylation. Earlier studies, for example, have shown that the conversion of ManNAc to ManNAc-6-P by intracellular kinases is a key bottleneck in the efforts to promote sialic acid biosynthesis in lower eukaryotes (Viswanathan et al., 2003).

One popular expression system that is currently limited by the inability to produce sialylated glycoproteins efficiently is the baculovirus-insect cell system, although it has been used to produce a wide variety of other recombinant proteins for biomedical and research applications (Jarvis, 2009; Kost et al., 2005; O'Reilly et al., 1992). All of the established insect cell lines and insects used as hosts for baculovirus-mediated foreign gene expression have less extensive glycoprotein glycan processing capabilities than higher eukaryotes (Geisler and Jarvis, 2009; Harrison and Jarvis, 2006; Jarvis, 2009; Shi and Jarvis, 2007). Recombinant forms of mammalian glycoproteins produced using the baculovirus-insect cell system, therefore, can have functional deficiencies due to the inability of the system to process glycans in a manner similar to that observed in mammalian cells.

The apparent absence of sialic acid metabolism in insect systems was first recognized in 1963 (Warren, 1963), and the notion that insects lack biochemical processes involved in sialic acid synthesis, CMP-sialic acid synthesis and synthesis of sialylated glycoconjugates has been supported by many other studies published over the past 50 years (Marchal et al., 2001; Shi and Jarvis, 2007). A variety of studies have shown that sialic acid synthase, CMP-sialic acid synthetase, and sialyltransferase activities, as well as CMP-sialic acids, are undetectable in lepidopteran insect cell lines, which are commonly used as hosts for baculovirus expression vectors (Aumiller et al., 2003; Hill et al., 2006; Hollister and Jarvis, 2001; Jarvis et al, 2001; Seo et al., 2001; Shi et al., 2007; Tomiya et al., 2001). It is also understood that the lepidopteran insect cell lines and insects used as hosts for baculovirus-mediated foreign gene expression fail to produce recombinant glycoproteins with terminally-sialylated glycans (Geisler and Jarvis, 2009).

Genetic engineering methods now known as "glyco-engineering" have been applied to the baculovirus-insect cell system in recent years to overcome these problems. This approach has involved introducing mammalian genes encoding enzymes involved in glycan processing, sialic acid synthesis, CMP-sialic acid synthesis and glycoconjugate sialylation into insect cell lines or insects in order to improve their endogenous glycoprotein processing capabilities. Glyco-engineering has been accomplished by genetically transforming established insect cell lines (Aumiller et al., 2003; Breitbach and Jarvis, 2001; Hollister and Jarvis, 2001; Hollister et al., 2002; Hollister et al., 1998) or by genetically engineering baculovirus vectors (Hill et al., 2006; Jarvis and Finn, 1996; Jarvis et al., 2001; Lawrence et al., 2001; Seo et al., 2001; Tomiya et al., 2003; Viswanathan et al., 2003). The genetic transformation approach has resulted in transgenic insect cell lines or insects that encode and constitutively express a set of mammalian genes that enable insect cells to produce sialylated glycoproteins. The vector engineering approach has resulted in new baculovirus vectors that not only introduce the gene encoding the recombinant glycoprotein of interest into susceptible cells, but also introduce a set of mammalian genes that enable insect cells to produce sialylated glycoproteins.

Current glyco-engineering methods still pose significant limitations in the ability of insect and other lower eukaryotic systems to produce sialylated glycoconjugates. Specifically, current glyco-engineering methods are limited in the production and processing of sialic acid precursors that are required to produce sialylated glycoconjugates (Viswanathan et al., 2003). New methods which offer cheaper, simpler, and more effective ways to engineer insect and other eukaryotic cells to produce sialylated glycoconjugates are therefore needed. One promising approach would be to engineer these lower eukaryotic systems to produce large, intracellular pools of CMP-sialic acids which are required for efficient sialylation of glycoconjugates, in a variety of eukaryotic expression systems, including fungal, plant, mammalian, and insect cell-based systems.

FIG. 1 sets forth an illustration showing the metabolism of sialic acid in vertebrates. Key differences in the N-glycan processing capabilities of insect and mammalian cells are illustrated in FIG. 2. Terminal glycosyltransferases, such as N-acetylglucosaminyltransferases, galactosyltransferases, and sialyltransferases, are often absent or present only at insufficient functional levels in insect systems. Differences in their protein glycosylation pathways also reflect the inability of insect cell lines and insects to synthesize and transport sialic acids and CMP-sialic acids, which are needed as donor substrates for N- and O-glycan sialylation by sialyltransferases. These differences provided the rationale for using mammalian genes encoding glycosyltransferases and other enzymes involved in sialic acid and CMP-sialic acid biosynthesis as the targets for earlier glyco-engineering efforts as shown in FIGS. 3 and 4.

The methods described herein greatly enhance the ability of genetically-modified host cell systems to facilitate the production of sialylated glycoproteins, by eliminating the need to supplement the cell culture media with expensive metabolic precursors, such as N-acetylmannosamine, needed to promote the efficient sialylation of recombinant proteins. In this study, genetically-modified insect cells were made which produce sufficient amounts of the required precursor. The cells were engineered to contain a variety of nucleic acids encoding polypeptides derived from mammalian sources needed to promote the sialylation of recombinant glycoproteins, plus a nucleic acid encoding E. coli N-acetylglucosamine-6-phosphate 2'-epimerase (GNPE), which normally functions in bacterial sialic acid degradation. Under normal conditions, these cells have the product, but not the substrate for this enzyme. Modified cells that comprise a nucleic acid encoding a GNPE that is expressed at a sufficient level could drive the reaction in reverse, initiating sialic acid biosynthesis in the absence of media supplementation. The modified insect cells efficiently produced sialic acid, CMP-sialic acid, and sialylated recombinant N-glycoproteins even in growth media without N-acetylmannosamine. This approach is not limited to insect cells, can be adapted to a variety of other eukaryotic host cell systems. The general scheme is illustrated in FIG. 5.

BRIEF SUMMARY OF THE INVENTION

The present invention relates to methods of engineering metabolic pathways in bacterial, fungal, plant, and animal cell-based systems used to facilitate the production of recombinant glycoconjugates having sialylated glycans similar to those observed in mammalian cells. The methods are particularly directed to nucleic acids encoding polypeptides involved in the sialylation of glycoconjugates, vectors comprising the nucleic acids, and cells harboring the vectors that express these enzymes above endogenous levels, particularly enzymes involved in the production of metabolic precursors of CMP-sialic acid, such as CMP-N-acetylneuraminic acid, that are used as donors of sialic acid in the production of sialylated glycoconjugates.

One aspect of the invention is directed to a cell which is modified to comprise and express at least one nucleic acid encoding a polypeptide, GlcNAc-6-P 2'-epimerase (GNPE), which is capable of directly converting N-acetyl-D-glucosamine-6-phosphate (GlcNAc-6-P) to N-acetyl-D-mannosamine-6-phosphate (ManNAc-6-P), wherein each nucleic acid is operably-linked to a promoter functional in said cell.

Another aspect of the invention relates to a method for converting N-acetyl-D-glucosamine-6-phosphate (GlcNAc-6-P) to N-acetyl-D-mannosamine-6-phosphate (ManNAc-6-P) in a cell, said method comprising the steps of: (a) introducing into said cell at least one nucleic acid encoding a polypeptide capable of converting N-acetyl-D-glucosamine-6-phosphate (GlcNAc-6-P) to N-acetyl-D-mannosamine-6-phosphate (ManNAc-6-P), wherein each nucleic acid is operably linked to a promoter functional in said cell; and (b) expressing at least one nucleic acid encoding a polypeptide capable of converting N-acetyl-D-glucosamine-6-phosphate (GlcNAc-6-P) to N-acetyl-D-mannosamine-6-phosphate (ManNAc-6-P).

One aspect is a method for converting N-acetyl-D-glucosamine-6-phosphate (GlcNAc-6-P) to CMP-N-acetylneuraminate (CMP-Neu5Ac) in a cell, said method comprising the steps of: (a) introducing into said cell, in any order: (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetyl-neuraminate-9-P to N-acetylneuraminate; (iv) at least one nucleic acid encoding a polypeptide capable of converting N-acetylneuraminate to CMP-N-acetylneuraminate; wherein each of said nucleic acids are operably-linked to a promoter which is functional in said cell; and (b) expressing each of the introduced nucleic acids such that the level of CMP-N-acetylneuraminate in said cell is enhanced above the endogenous level of CMP-N-acetylneuraminate in a parent cell lacking one or more of said nucleic acids.

One aspect is a method for preparing a cell which is modified to comprise nucleic acid encoding one or more polypeptides capable of converting N-acetyl-D-glucosamine-6-phosphate (GlcNAc-6-P) to CMP-N-acetylneuraminate (CMP-Neu5Ac) in a cell, said method comprising the steps of (a) introducing into said cell, in any order: (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetyl-neuraminate-9-P to N-acetylneuraminate; (iv) at least one nucleic acid encoding a polypeptide capable of converting N-acetylneuraminate to CMP-N-acetylneuraminate; wherein each of said nucleic acids are operably-linked to a promoter which is functional in said cell.

One aspect is a method of producing a sialylated glycoprotein in a modified cell comprising the steps of: (a) introducing an expression vector comprising a nucleic acid encoding a recombinant protein into a modified cell, wherein said cell comprises (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetyl-neuraminate-9-P to N-acetylneuraminate; (iv) at least one nucleic acid encoding a polypeptide capable of converting N-acetylneuraminate to CMP-N-acetylneuraminate; wherein each nucleic acid is operably linked to a promoter functional in said cell; (b) expressing the nucleic acid encoding said recombinant protein; and (c) isolating the sialylated glycoprotein from the modified cells or from cell culture medium obtained from the modified cells.

One aspect is a method for producing a transgenic insect larva comprising in at least some of its somatic or germ cells at least one nucleic acid encoding a polypeptide capable of converting N-acetyl-D-glucosamine-6-phosphate (GlcNAc-6-P) to N-acetyl-D-mannosamine-6-phosphate (ManNAc-6-P) comprising the steps of: (a) introducing a nucleic acid encoding GNPE into a larval cell, wherein said nucleic acid is operably-linked to a promoter functional in said cell, and (b) growing the larva under conditions wherein said GNPE nucleic acid is expressed, and GNPE activity is above endogenous levels of activity in a larva lacking said nucleic acid.

A better understanding of the invention will be obtained from the following detailed descriptions and accompanying drawings, which set forth illustrative embodiments that are indicative of the various ways in which the principals of the invention may be employed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 13 sets forth α2-6 linked sialoglycoconjugates on the cell surface of insect cells expressing the *Escherichia coli* GNPE as well as other enzymes required for sialic acid biosynthesis and utilization. Panels 13A, 13C, 13E: Phase contrast images of Sf9, SfSWT-20 and SfSWT-21 cells, respectively. Panels 13B, 13D, 13F: Red fluorescence imaging of SfSWT-20 and SfSWT-21 cells, respectively, stained with SNA-biotin and Texas Red-Streptavidin.

FIG. 14 sets forth α2-3 linked sialoglycoconjugates on the cell surface of insect cells expressing the *Escherichia coli* GNPE as well as other enzymes required for sialic acid biosynthesis and utilization. Panels 14A, 14C, 14E: Phase contrast images of Sf9, SfSWT-20 and SfSWT-21 cells, respectively. Panels 14B, 14D, 14F: Red fluorescence imaging of SfSWT-20 and SfSWT-21 cells, respectively, stained with MAL-biotin and Texas Red-Streptavidin.

FIG. 15 sets forth key pathways in the synthesis of CMP-N-acetylneuraminate (CMP-sialic acid), showing the structures of key intermediates.

FIG. 16 sets forth key pathways in the synthesis of CMP-N-acetylneuraminate (CMP-Sialic Acid), without showing the structures of key intermediates.

FIG. 17 sets forth key pathways in the synthesis of sialylated glycoconjugates from CMP-Neu5Ac and CMP-Neu5Gc, without showing the structures of key intermediates.

FIG. 18 sets forth data demonstrating that bacterial GNPE increases sialic acid and CMP-sialic acid content of insect cells cultured in the absence of ManNAc: (A) Total sialic acid content of expresSF+, SfSWT-19, and SfSWT-21 cells cultured in PSFM medium with or without Ac4ManNAc. (B) CMP-sialic acid content of expresSF+, SfSWT-19, and SfSWT-21 cells cultured in PSFM medium with or without Ac4ManNAc.

FIG. 19 sets forth data demonstrating that bacterial GNPE increases sialylation of endogenous insect cell surface glycoconjugates without ManNAc supplementation: ConA staining reveals mannose-containing glycoconjugates on the surfaces of expresSF+, SfSWT-19, and SfSWT-21 cells cultured in PSFM medium without (A) or with (C) Ac4ManNAc. SNA staining reveals sialylated glycoconjugates on the surfaces of expresSF+, SfSWT-19, and SfSWT-21 cells cultured in PSFM medium without (B) or with (D) Ac4ManNAc.

FIG. 20 sets forth data demonstrating that insect cells expressing bacterial GNPE sialylate mIgG2a-Fc without ManNAc supplementation: (A) CBB staining, (B) immunoblotting, (C) ConA lectin blotting, and (D) SNA lectin blotting of recombinant mIgG2a-Fc produced by expresSF+, SfSWT-19, and SfSWT-21 cells cultured in PSFM medium with or without Ac4ManNAc. Some samples of the protein produced under each condition were treated with sialidase or PNGase-F, as indicated by the labels in the Figure and as described in Materials and methods.

FIG. 21 sets forth data demonstrating that insect cells expressing bacterial GNPE sialylate hEPO without ManNAc supplementation: (A) CBB staining, (B) immunoblotting, (C) ConA lectin blotting, and (D) SNA lectin blotting of recombinant mIgG2a-Fc produced by expresSF+, SfSWT-19, and SfSWT-21 cells cultured in PSFM medium with or without Ac4ManNAc. Some samples of the protein produced under each condition were treated with sialidase or PNGase-F, as indicated by the labels in the Figure and as described in Materials and methods.

FIG. 22 sets forth sialic acid biosynthetic and degradative pathways in different host systems. (A) GNE initiates sialic acid metabolism in mammals. (B) GNPE functions in sialic acid degradation in bacteria. (C) Hybrid bacterial/mammalian sialic acid pathway in glycoengineered insect cells.

The following is a list of terms and their definitions used throughout the specification and the claims:

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as an insect larva or a transgenic mammal.

The term "glycoconjugate" refers to complex molecules containing glycosidic linkages, such as glycolipids, glycopeptides, oligosaccharides, or glycosaminoglycans. Generally, in the context of expression systems, where a gene encoding a heterologous protein is expressed under the control of a promoter operable in a host cell, which may be in a cultured cell, in a tissue sample, or in a transgenic organism, glycoconjugate typically refers to a glycoprotein, where a mono- or oligo-saccharide is conjugated to a protein, most commonly through N- or O-linked bonds to amino acid residues.

The term "Sialic acid" refers to N- or O-substituted derivatives of neuraminic acid, a monosaccharide with a nine-carbon backbone, as shown in the panels below: (a) Neuraminic acid, the core structure of all sialic acids. Structural modifications can be made at C4, C7, C8, C9, and at the amine group of C5; (b) Structure of N-acetylneuraminic acid (Neu5Ac); (c) Structure of N-glycolylneuraminic acid (Neu5Gc); and (d) Structure of N-acetyl-9-O-acetylneuraminic acid (Neu5,9Ac2).

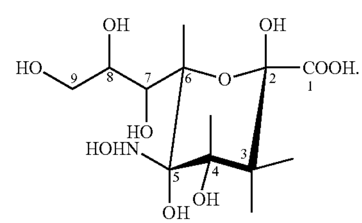

a 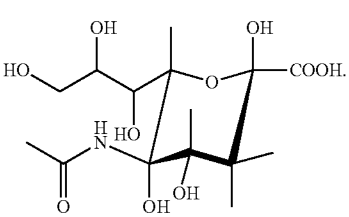 b 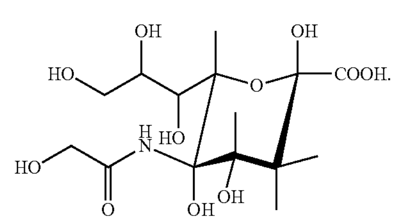 c

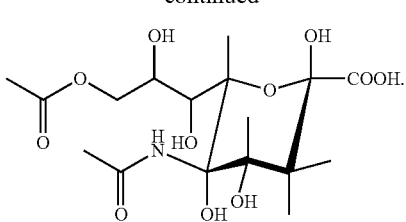

Figure 1:
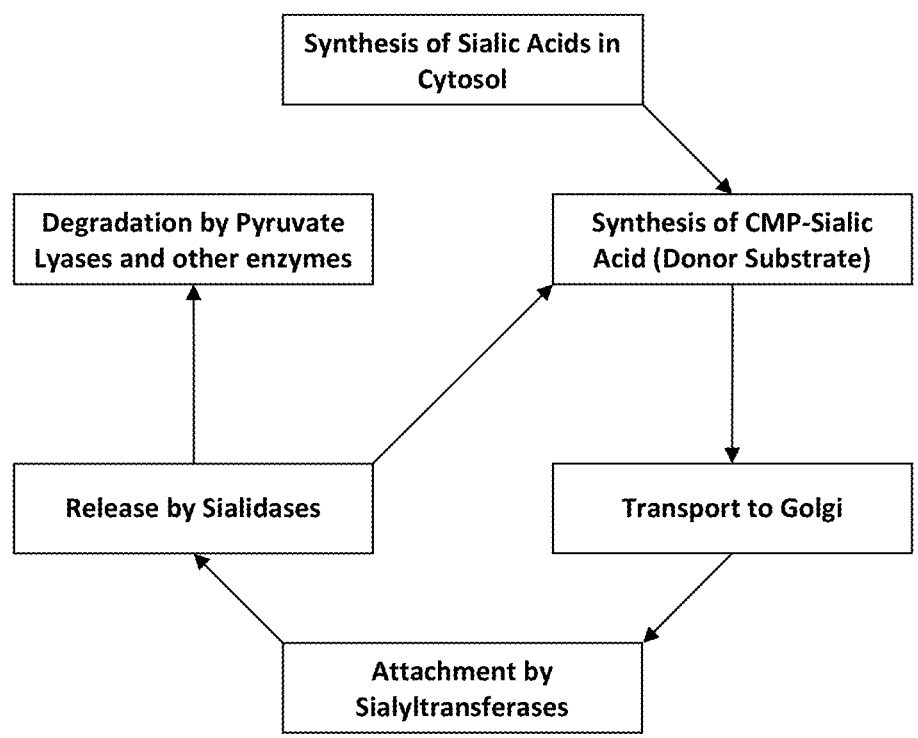
FIG. 1 sets forth an illustration showing the metabolism of sialic acid in vertebrates.
Figure 2:
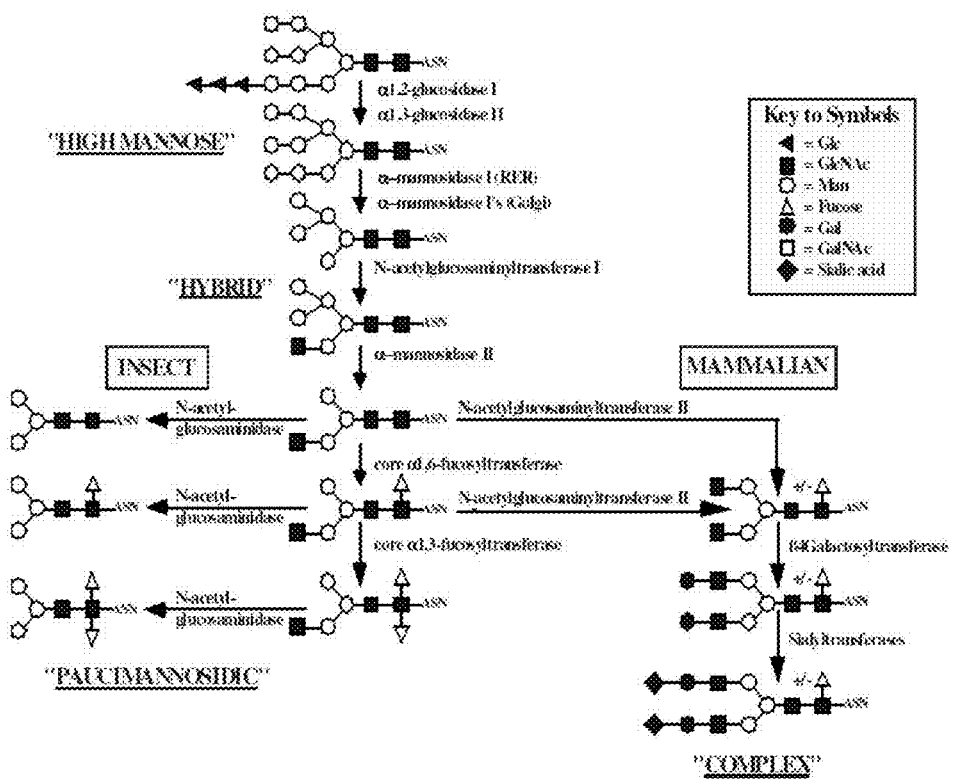
FIG. 2 sets forth an illustration showing key differences in the N-glycan processing capabilities of insect and mammalian cells.
Figure 3:
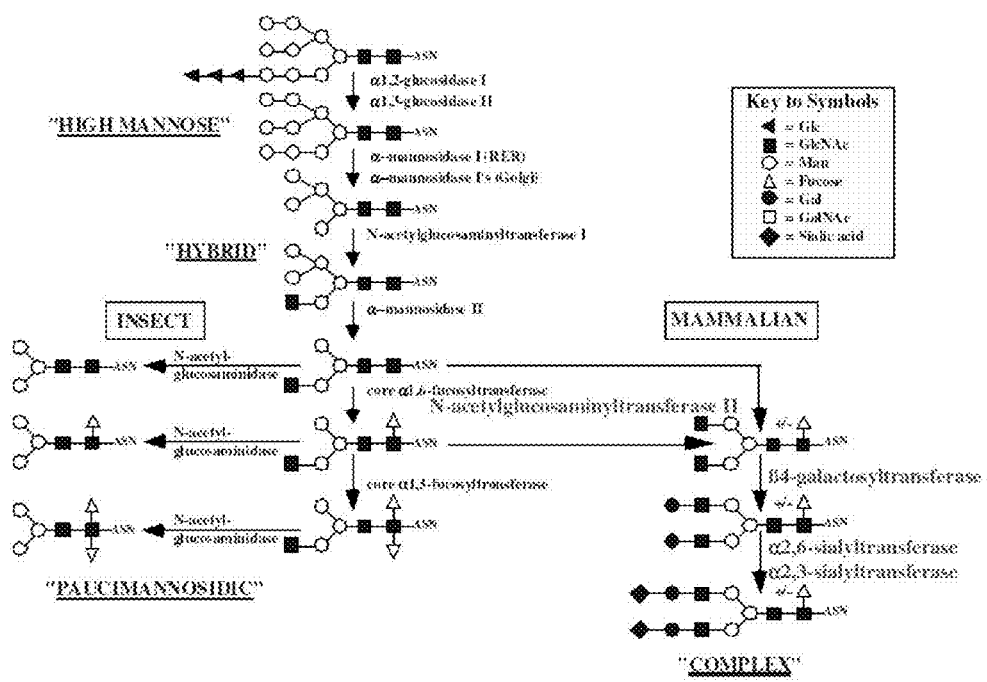
FIG. 3 sets forth an illustration showing that terminal glycosyltransferases, such as N-acetylglucosaminyltransferases, galactosyltransferases, and sialyltransferases, among many others, are often absent or present only at low functional levels in insect systems. Differences in their protein glycosylation pathways also reflect the inability of insect cell lines and insects to synthesize and transport sialic acids and CMP-sialic acids, which are needed as donor substrates for N- and O-glycan sialylation by sialyltransferases.
Figure 4:
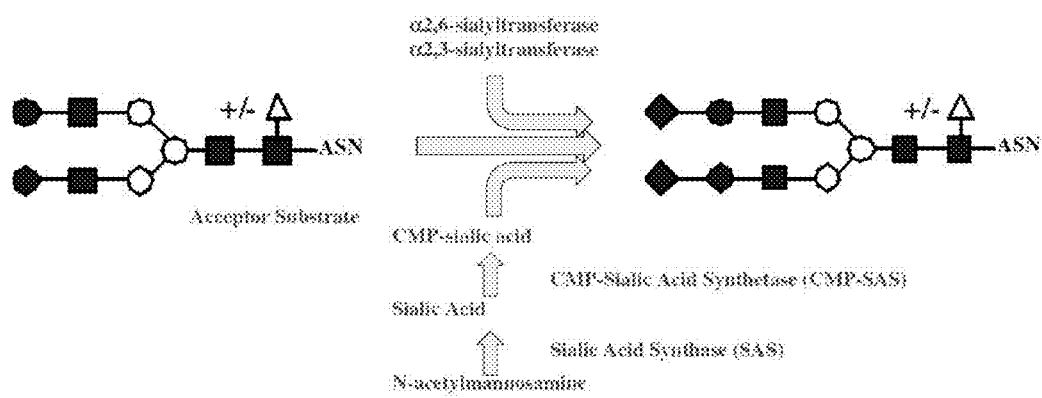
FIG. 4 sets forth an illustration showing enzymes involved in sialic acid and CMP-sialic acid biosynthesis as the targets for earlier glyco-engineering efforts.

The two most common sialic acid derivatives are N-Acetylneuraminic acid (Neu5Ac) and 2-Keto-3-deoxynonic acid (KDN). Neu5Ac has an amino-acetyl group at C5, which is absent in KDN.

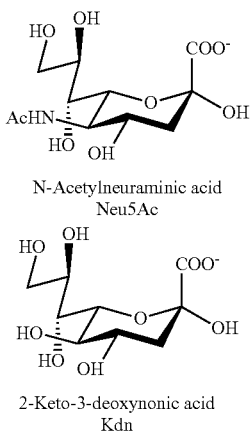

N-Acetylneuraminic acid
Neu5Ac

2-Keto-3-deoxynonic acid
Kdn

The terms "GlcNAc" and "NAG" mean N-acetylglucosamine (N-acetyl-D-glucosamine), a monosaccharide derivative of glucose, and an amide consisting of acetylated glucosamine.

The terms "ManNAc" and "NAM" mean N-acetylmannosamine (N-acetyl-D-mannosamine), a monosaccharide derivative of mannose, and an amide consisting of acetylated mannosamine. GlcNAc and ManNAc are epimers, differing only in the configuration of the OH group at the carbon 2 position.

The term "UDP-N-acetylglucosamine-2-epimerase" with respect to eukaryotic UDP-N-acetylglucosamine-2-epimerase/N-acetylmannosamine-6-kinase means enzymes that produce N-acetylmannosamine from UDP-N-acetylglucosamine, exemplified by the epimerase domain of human UDP-N-acetylglucosamine-2-epimerase/N-acetylmannosamine-6-kinase (GNE gene) (DNA: NM_005476 bases 216 to 2384; Protein: NP_005467.1).

The term "UDP-N-acetylglucosamine-2-epimerase" with respect to prokaryotic UDP-N-acetylglucosamine-2-epimerase, means enzymes that produce N-acetylmannosamine from UDP-N-acetylglucosamine, exemplified by E. coli str. K-12 substr. MG1655 UDP-N-acetylglucosamine-2-epimerase (NeuC gene) (DNA: M84026.1; Protein: AAA24211.1).

The term "N-acetylglucosamine-2-epimerase" with respect to eukaryotic N-acetylglucosamine-2-epimerase, means enzymes that produce N-acetylmannosamine from N-acetylglucosamine, exemplified by Sus scrofa (pig) N-acetylglucosamine-2-epimerase (RENBP gene) (DNA: NM_213900 bases 68 to 1276; Protein: P17560.2).

The term "N-acetylglucosamine-2-epimerase" with respect to prokaryotic N-acetylglucosamine-2-epimerase, means enzymes that produce N-acetylmannosamine from N-acetylglucosamine, exemplified by Synechocystis sp. PCC 6803 N-acetylglucosamine-2-epimerase (Slr1975 gene) (DNA: NC_000911.1 bases 1793852 to 1795027; Protein: NP_441530.1).

The term "N-acetylglucosamine-6-kinase" with respect to eukaryotic N-acetylglucosamine-6-kinases, means enzymes which produce N-acetylglucosamine-6-phosphate from N-acetylglucosamine and ATP, exemplified by human N-acetylglucosamine-6-kinase (NagK gene) (DNA: NM_017567 bases 269 to 1441; Protein: Q9UJ70.4).

The term "N-acetylglucosamine-6-kinase" with respect to prokaryotic N-acetylglucosamine-6-kinases, means enzymes which produce N-acetylglucosamine-6-phosphate from N-acetylglucosamine and ATP, exemplified by E. coli str. K-12 substr. MG1655 N-acetylglucosamine-6-kinase (NagK gene) (DNA: NC_000913.2 bases 1177816 to 1178727; Protein: NP_415637.1).

The term "N-acetylmannosamine-6-Kinase" with respect to eukaryotic UDP-N-acetylglucosamine-2-epimerase/N-acetylmannosamine-6-kinase means enzymes which produce N-acetylmannosamine-6-P from N-acetylmannosamine and ATP, exemplified by the kinase domain of human UDP-N-acetylglucosamine-2-epimerase/N-acetylmannosamine-6-kinase (GNE gene) (DNA: NM_001128227 bases 113 to 2374; Protein: NP_001121699.1).

The term "N-acetylmannosamine-6-Kinase" with respect to prokaryotic N-acetylmannosamine-6-Kinase means enzymes which produce N-acetylmannosamine-6-P from N-acetylmannosamine and ATP, exemplified by E. coli str. K-12 substr. MG1655 N-acetylmannosamine-6-Kinase (NanK gene) (DNA: NC_000913.2 bases 3367497 to 3368372; Protein: NP_417689.4).

The term "Sialic acid synthase" or SAS, with respect to eukaryotic sialic acid synthase means enzymes which produce phosphorylated sialic acids (e.g., N-acetylneuraminic acid-9-phosphate) by condensation of phosphoenolpyruvate and N-acetylmannosamine-6-phosphate, exemplified by mouse sialic acid synthase (Nans gene) (DNA: NM_053179.3 bases 31 to 1110; Protein: NP_444409.1).

The term "Sialic acid synthase" with respect to prokaryotic sialic acid synthase means enzymes which produce free sialic acids (e.g. N-acetylneuraminic acid) by condensation of phosphoenolpyruvate and N-acetylmannosamine, exemplified by Escherichia coli strain RS218 sialic acid synthase (NeuB gene) (DNA: ECU05248 bases 723 to 1763; Protein: AAC43302.1).

The term "sialic acid-9-phosphate phosphatases" with respect to eukaryotic sialic acid-9-phosphate phosphatases, means enzymes which produce free sialic acids from phosphorylated sialic acids, exemplified by mouse sialic acid-9-phosphate phosphatase (NanP gene) (DNA: BC083086 bases 54 to 800; Protein: AAH83086).

The term "CMP-Sialic acid synthetase" or CSAS, with respect to eukaryotic CMP-sialic acid synthetases means enzymes which produce CMP-sialic acids from free sialic acids and CTP, exemplified by Mouse CMP-sialic acid synthetase (CMAS gene) (DNA: NM_009908.2 bases 88 to 1386; Protein: NP_034038.2).

The term "CMP-Sialic acid synthetase" or CSAS, with respect to prokaryotic CMP-sialic acid synthetases means enzymes which produce CMP-sialic acids from free sialic acids and CTP, exemplified by *E. coli* 0145 CMP-sialic acid synthetase (NeuA gene) (DNA: J05023.1 bases 24 to 1283; Protein: AAA24210.1).

The term "CMP-sialic acid transporter" or CSAT with respect to eukaryotic CMP-sialic acid transporters means transporters which facilitate the transport of CMP-sialic acids from the cytoplasm to the lumen of the Golgi apparatus, exemplified by the mouse CMP-sialic acid transporter (CST gene) (DNA: NM_011895.3 bases 180 to 1190; Protein: NP_036025.2).

The term "glycosyltransferase" is a generic term that refers to enzymes classified as EC 2.4 in the EC number classification scheme, which catalyze the transfer of a monosaccharide unit from an activated nucleotide sugar (also known as the "glycosyl donor") to a glycosyl acceptor molecule, usually an alcohol. For many glycosyltransferases, the product is a carbohydrate, glycoside, oligosaccharide, or a polysaccharide. Glycosyl transfer can also occur to inorganic phosphate or water, to amino acid residues such as tyrosine, serine, or threonine in proteins to produce O-linked glycoproteins, or to asparagine to produce N-linked glycoproteins. Mannosyl moieties can be transferred to tryptophan to generate C-mannosyl tryptophan. Lipids can be used as an acceptor, forming glycolipids, and lipid-linked sugar phosphate donors, such as dolichol phosphates can also be produced. One type of eukaryotic glycosyltransferases useful in the methods of the invention is bovine β1,4 galactosyltransferase (GalT1 gene) (DNA: NM_177512 bases 1 to 1209; Protein: NP_803478.1).

The term "Sialyltransferase" refers to enzymes classified as EC 2.4.29, as glycosyltransferase family 29 in the EC number classification scheme, that transfer sialic acid from the activated nucleotide sugar CMP-sialic acid to oligosaccharide acceptors. Individual sialyltransferases have particular oligosaccharide acceptor substrate specificities. Sialyltransferases add sialic acid to the terminal portions of glycolipids (gangliosides) or to the N- or O-linked sugar chains of glycoproteins. Sialyltransferase (EC 2.4.99), beta-galactoside alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetyl-neuraminide alpha-2,8-sialyltransferase (EC 2.4.99.8); lactosylceramide alpha-2,3-sialyltransferase (EC 2.4.99.9) use a nucleotide monophosphosugar as the donor (CMP-sialic acid), instead of a nucleotide diphosphosugar. One type of sialyltransferase useful in the methods of the invention is Rat alpha2,6 sialyltransferase, encoded by the ST6Gal1 gene (DNA: NM_001113344.1 bases 182 to 1393; Protein: NP_001106815.1). Another enzyme that is useful in the methods of the invention is human alpha2,3 sialyltransferase, encoded by the ST3Gal4 gene (DNA: NM_006278.1 bases 163 to 1152; Protein: NP_006269.1).

The term "glycosylhydrolase" is a generic term that refers to a widespread group of enzymes that hydrolyze the glycosidic bond between two or more carbohydrates, or between a carbohydrate and a non-carbohydrate moiety classified as EC 3.2.1, in the EC number classification scheme. One type of glycosylhydrolase useful in the methods of the invention is human Golgi mannosidase II (ManIIA1 gene) (DNA: NM_002372.2 bases 1 to 3435; Protein: NP_002363.2).

The term "isolated" when used with respect to a polynucleotide (e.g., single- or double-stranded RNA or DNA), an enzyme, or more generally a protein, means a polynucleotide, an enzyme, or a protein that is substantially free from the cellular components that are associated with the polynucleotide, enzyme, or protein as it is found in nature. In this context, "substantially free from cellular components" means that the polynucleotide, enzyme, or protein is purified to a level of greater than 80% (such as greater than 90%, greater than 95%, or greater than 99%).

The term "transposon" refers to mobile genetic elements capable of transposition between the genetic material in a cell (e.g., from one chromosomal location to one or more other locations in the chromosome, from a virus or a plasmid to the chromosome, from the chromosome to a virus or a plasmid, and from a plasmid or virus to a different plasmid or virus). A non-limiting list of transposons that may be used with the invention described herein, includes piggyBac, Sleeping Beauty (SB), Tn7, Tn5, Tn916, Tcl/mariner, Minos and S elements, Quetzal elements, Txr elements, maT, most, Himarl, Hermes, Tol2 element, Pokey, P-element, and Tc3.

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; ug, μg=micro gram(s); ul, μl=micro liter(s); uM, μM=micromolar.

Specific abbreviations and their corresponding meanings include: Ac4ManNAc=peracetylated N-acetyl-D-mannosamine; AcNPV=*Autographa californica* nuclear polyhedrosis virus; ATP=Adenosine triphosphate; BmNPV=*Bombyx mori* nuclear polyhedrosis virus; CBB=Coomassie Brilliant Blue; CHO=Chinese hamster ovary; CMAS=CMP-sialic acid synthetase; CMP=cytidine monophosphate; CMP-Sia=CMP-sialic acid; ConA=Concanavalin A; CSAS=CMP-sialic acid synthetase; CSAT=CMP-sialic acid transporter; CTP=cytidine triphosphate; EST=expressed sequence tag; FITC=fluorescein isothiocyanate; GH=glycosylhydrolases; GLC-MS=Gas-liquid chromatography-mass spectrometry; GlcNAc=N-acetyl-D-glucosamine; GlcNAc-6-P=N-acetyl-D-glucosamine-6-Phosphate; GNE=UDP-N-acetyl-D-glucosamine 2'-epimerase/N-acetylmannosamine kinase; GNPE=N-acetyl-D-glucosamine-6-phosphate 2'-epimerase; GT=glycosyltransferases; hCSAT=human CSAT; hEPO=human erythropoietin; HPLC=high-performance liquid chromatography; hUGlcNAcT=human UDP-N-acetylglucosamine transporter; hUGT=human UDP-Galactose transporter; ManNAc=N-acetyl-D-mannosamine; ManNAc-6-P=N-acetyl-D-mannosamine-6-phosphate; NANP=sialic acid-9-phosphate phosphatase; Neu5Ac=N-acetylneuraminic acid; NPV=Nuclear polyhedrosis virus; NST=Nucleotide sugar transporter; ORF=open reading frame; PCR=polymerase chain reaction; PEP=phosphoenolpyruvate; PNGase-F=*Flavobacterium meningosepticum* peptide:N-glycanase F; PSFM=Protein Sciences Fortified Medium; RT=reverse transcriptase; SAS=Sialic acid synthase; SDS-PAGE=sodium dodecyl sulfate-polyacrylamide gel electrophoresis; Sf21=*Spodoptera frugiperda* (IPLB Sf21) cells/cell line; Sf9=*Spodoptera frugiperda* (Sf9) cells/cell line; SNA=*Sambucus nigra* agglutinin; ST=sialyltransferase; Tni, *T. ni*=*Trichoplusia ni*; Tni368=*Trichoplusia ni* (Tni368) cells/cell line; UDP-Gal=UDP-galactose; UDP-GalNAc=UDP-N-acetylgalactosamine; UDP-GlcNAc=UDP-N-acetylglucosamine; UGlcNAcT=UDP-N-acetylglucosamine transporter; UGT=UDP-Galactose transporter.

DETAILED DESCRIPTION OF THE INVENTION

The present invention relates to methods of engineering metabolic pathways in bacterial, fungal, plant, and animal cell-based systems used to facilitate the production of glycoconjugates comprising sialic acid. The methods are particularly directed to cloned genes, vectors comprising the cloned genes, and cells harboring the vectors that express enzymes above endogenous levels involved in the production of metabolic precursors of CMP-sialic acid, exemplified by CMP-N-acetylneuraminic acid, that are used as sialic donors acid in the production of sialylated glycoconjugates, such as sialylated glycoproteins.

A key limitation of existing methods used in engineering lower eukaryotic cells to produce sialylated glycoconjugates is that the suboptimal availability of metabolic precursors required for the production of CMP-sialic acid, such as ManNAc-6-P, is limiting the production of sialylated glycoconjugates.

One way to promote glycoconjugate sialylation in lower eukaryotic cells is to cultivate the cells in growth medium supplemented with a sialic acid precursor such as ManNAc. However, ManNAc is expensive, and adding it to the growth medium is inconvenient, increases the risk of culture contamination, and often ManNAc supplementation leads to intracellular CMP-sialic acid levels that are insufficient for efficient glycoconjugate sialylation. Intracellular kinases are required to convert ManNAc to ManNAc-6-P in this approach, which is often a bottleneck in efforts to promote sialic acid biosynthesis in lower eukaryotes (Viswanathan et al., 2003).

Figure 9:
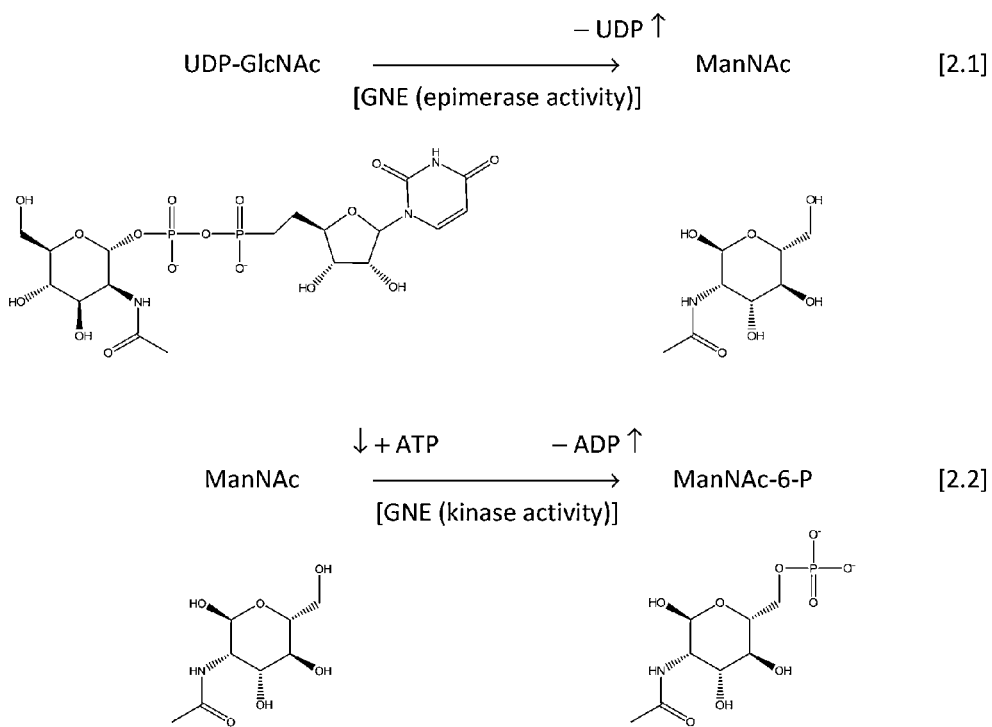
FIG. 9 sets forth a series of three reactions (2.1-2.3) illustrating use of a bifunctional GNE to promote glycoconjugate sialylation.

Another way to promote glycoconjugate sialylation in lower eukaryotic cells is by expressing a gene that encodes a bifunctional enzyme called UDP-GlcNAc 2-epimerase/ManNAc kinase (GNE) in this cell type. This enzyme can convert UDP-N-acetyl-D-glucosamine (UDP-GlcNAc) to ManNAc-6-P in two distinct enzymatic steps (FIG. 9, reactions 2.1 and 2.2). This approach is not desirable, however, as it depletes intracellular pools of UDP-GlcNAc, which is a key compound that can be limiting the production of glycoconjugate intermediates if present in suboptimal levels (Sasai et al., 2002). Sialoglycoconjugate biosynthesis also often depends upon the availability of UDP-GlcNAc for the production of acceptor substrates (Schachter, 2000).

Figure 10:
FIG. 10 sets forth a series of two reaction schemes (3.1-3.2) illustrating use of two enzymes (a renin-binding protein, RBP, having epimerase activity, and ManNAc kinase) to promote glycoconjugate sialylation.
Figure 10:
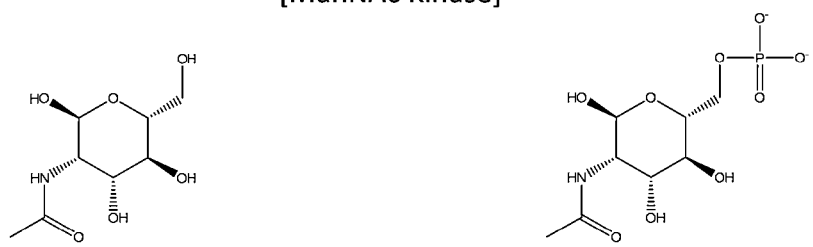

A third way to promote glycoconjugate sialylation in lower eukaryotic cells is by expressing two genes that encode two separate enzymes that lead to the production of ManNAc-6-P in lower eukaryotic cells. The first enzyme is renin binding protein (RBP/RenBP), which has a GlcNAc 2-epimerase activity that can convert GlcNAc to ManNAc (FIG. 10, reaction 3.1). The second enzyme is ManNAc kinase, which phosphorylates ManNAc to produce ManNAc-6-P (FIG. 10, reaction 3.2). Ensuring that both of these genes are expressed at sufficient levels to carry out the desired reactions at sufficient high levels is often a challenge.

The approach described below addresses many of these limitations by providing a cheaper, simpler, and more effective way to engineer cells to produce large, intracellular pools of CMP-sialic acids required for efficient glycoconjugate sialylation, in a variety of expression systems, including bacterial, fungal, plant, and insect cell-based systems.

After considering the metabolic pathways involved in the biosynthesis of sialylated glycoconjugates, we recognized that intracellular pools of ManNAc-6-P may be limiting in many of the current systems for the generation of sialylated glycoconjugates, and that overcoming this limitation is key to efficient sialylation in these systems. To generate large intracellular pools of CMP-sialic acid precursors, we genetically engineered lower eukaryotic cells to produce ManNAc-6-P, eliminating the need to supplement the cellular growth medium with a sialic acid precursor such as ManNAc, and bypassing the bottleneck posed by the requirement for its conversion to ManNAc-6-P by intracellular kinases. To the best of our knowledge, this approach has not been reported anywhere.

Figure 5:
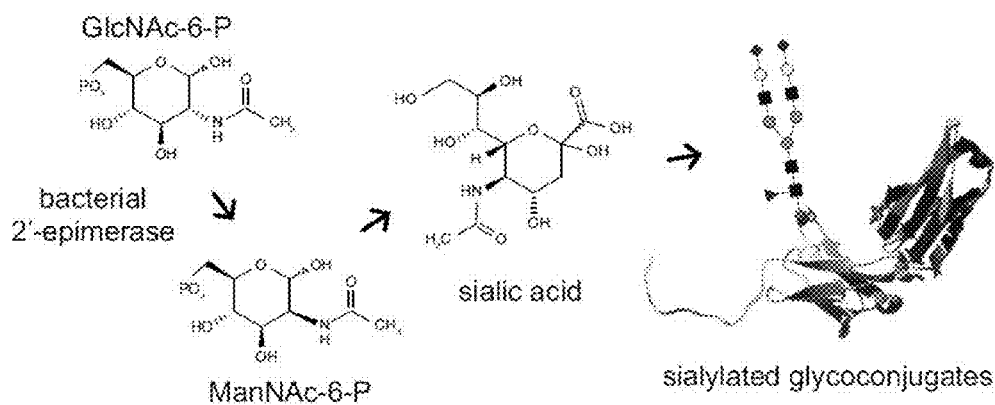
FIG. 5 sets forth a general scheme for using bacterial and mammalian genes encoding sialic acid pathway enzymes to facilitate the production of sialylated glycoconjugates in insect cells.

Our new approach relies on use of a bacterial enzyme called N-acetyl-D-glucosamine-6-phosphate 2'-epimerase (GNPE). In bacteria, this enzyme normally catalyzes conversion of ManNAc-6-P to GlcNAc-6-P, which is a step in sialic acid degradation. Lower eukaryotic cells engineered to contain a gene encoding and expressing GNPE, we reasoned, would exclusively carry out the reverse reaction, conversion of GlcNAc-6-P to ManNAc-6-P, when intracellular levels of GlcNAc-6P are high and ManNAc-6-P are low or non-existent. GNPE could be used then to initiate a sialic acid biosynthetic pathway by converting the abundant pools of GlcNAc-6-P in lower eukaryotic cells to ManNAc-6-P in a single step (FIG. 5, reaction 1.1).

Figure 7:
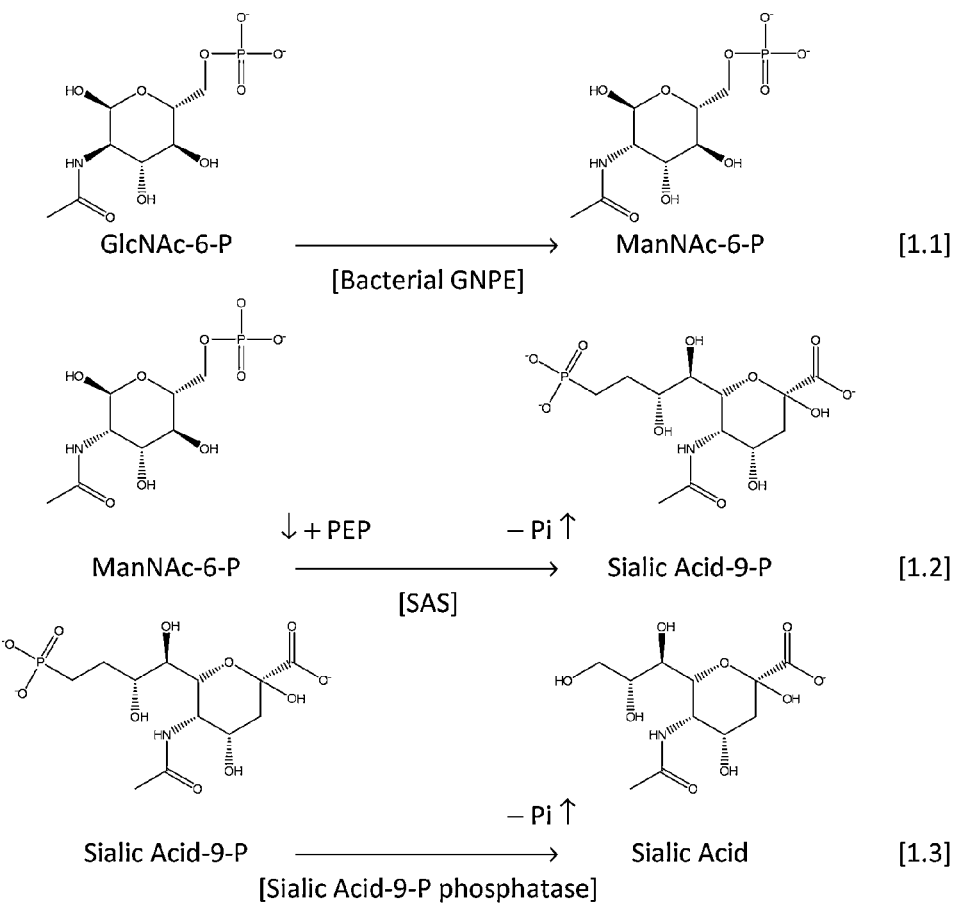
FIGS. 7 and 8 set forth a series of five reaction schemes (1.1-1.5) illustrating use of a bacterial epimerase to promote glycoconjugate sialylation.
Figure 8:
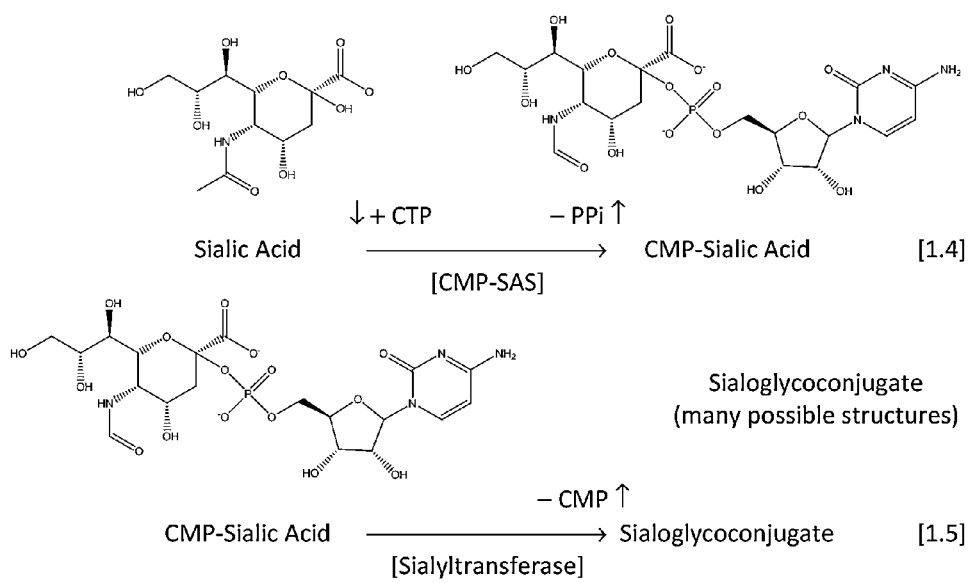

This new approach offers several advantages over the media supplementation approach described above, because GNPE converts pre-existing pools of GlcNAc-6-P to ManNAc-6-P, simultaneously eliminating the need for ManNAc supplementation, and bypassing the bottleneck posed by the inefficient conversion of ManNAc to ManNAc-6P by intracellular kinases. The resulting ManNAc-6-P can then be used by endogenous and/or heterologous eukaryotic sialic acid synthases (SAS; FIG. 7, reaction 1.2), sialic acid-9-phosphatases (FIG. 7, reaction 1.3), and CMP-sialic acid synthetases (CSAS; FIG. 8, reaction 1.4) in the same cells to produce large, intracellular pools of CMP-sialic acid, which would promote efficient sialylation of newly-synthesized glycoconjugates (FIG. 8, reaction 1.5). This approach is an improvement over the GNE overexpression approach because GNPE uses GlcNAc-6-P, rather than UDP-GlcNAc as a substrate. It is also an improvement over the RBP/ManNAc kinase co-expression approach, which requires co-expression of two enzymes, as it requires the expression of only a single enzyme that directly and efficiently converts GlcNAc-6-P to ManNAc-6-P in a single step.

The new approach also offers several economic advantages over the older methods described above. Insect cell culture medium, for example, is typically supplemented with 10 millimolar ManNAc to facilitate sialylation of recombinant proteins. The cost of this compound varies, but can be purchased in bulk for about USD $6.50 per gram. State-of-the-art bioreactors used to culture insect cells are available in sizes as large as 600 Liters, with larger sizes on the horizon. At this scale, a single batch of insect cell culture medium supplemented with ManNAc would cost over USD $8,600. Eliminating this cost, and the risk of contamination introduced by supplementation, are highly desirable in large-scale production facilities which may be subject to inspection by a variety of regulatory agencies. The cost savings would also apply to other expression systems as well, which would allow our new approach to be extended to bacterial, fungal, algal, plant, and vertebrate systems, including mammalian cells, where efficient glycoconjugation is desired and production in larger bioreactors or fermenters is feasible.

A variety of patent documents disclose the methods described above to generate ManNAc-6-P in cells to facilitate synthesis of sialic acid precursors used in the production of complex glycoconjugates. None of them, however, disclose or suggest the use of GNPE, as described herein, to facilitate the production of ManNAc-6-P from GlcNAc-6-P, as a key intermediate in the production of glycoconjugates, such as complex glycoproteins.

U.S. Pat. No. 7,781,647 and related applications by H. A. C. Bakker and H. J. Bosch, for example, disclose plants comprising a gene which encodes and stably expresses a mammalian β1,4-galactosyltransferase and a gene which encodes and stably expresses a rat β1,3-glucuronyltransferase, to produce an antibody or functional fragment thereof comprising a complex N-linked glycan.

U.S. Pat. No. 7,863,020 and related applications by S. R. Hamilton, disclose *Pichia pastoris* host cells which are engineered to produce recombinant proteins with complex glycoforms, wherein the host cells comprise one or more genes encoding a bifunctional UDP-N-acetylglucosamine-2-epimerase/N-acetylmannosamine kinase, an N-acetylneuraminate-9-phosphate synthase, and a CMP-sialic acid synthase; a gene encoding a CMP-sialic acid transporter; and a hybrid gene encoding a 2,6-sialyltransferase.

U.S. Pat. No. 6,949,372 and U.S. Pat. No. 7,776,565 by Betenbaugh et al., disclose the coupled use of human SAS and human or bacterial CSAS to facilitate the production of recombinant proteins having complex glycoforms in a variety of cell types.

US 2007/0067855 by Jarvis et al., and US 2010/0186099, by Fraser and Jarvis, disclose transgenic insects comprising at least one nucleic acid integrated into the cellular genome encoding two or more enzymes capable of facilitating N-glycosylation of a heterologous protein with a mammalianized (e.g., humanized) glycosylation pattern.

US 2008/0145899 by Johnson et al., disclose production of oligosaccharides by a microorganism grown in a culture media comprising a glucose moiety, such as N-acetylglucosamine, wherein the microorganism comprises an enzymatic system for synthesizing sialic acid from N-acetylglucosamine, such as a UDP-GlcNAc epimerase and a sialic acid synthase.

US 2011/0014661 by Samain, discloses methods of producing sialylated oligosaccharides in bacteria. This application, however, incorrectly describes the product of the *Campylobacter jejuni* neuC gene as a GlcNAc-6-P 2'-epimerase, compared to an earlier publication (Fierfort and Samain, J. Biotechnology 134:261-265 2008), which described the gene as clearly encoding a UDP-GlcNAc 2 epimerase (eukaryotic GNE), which has a completely different substrate specificity profile than the GlcNAc-6-P 2'-epimerase described herein.

One aspect of the invention is directed to a cell which is modified to comprise and express at least one nucleic acid encoding a polypeptide, GlcNAc-6-P 2'-epimerase (GNPE), which is capable of directly converting N-acetyl-D-glucosamine-6-phosphate (GlcNAc-6-P) to N-acetyl-D-mannosamine-6-phosphate (ManNAc-6-P), wherein each nucleic acid is operably-linked to a promoter functional in said cell. Another aspect of the invention relates to a modified cell, wherein said polypeptide is expressed, and the level of activity for a polypeptide capable converting GlcNAc-6-P to ManNAc-6-P in said cell is enhanced above the endogenous level of said activity in a parent cell lacking an introduced nucleic acid encoding said polypeptide.

The nucleic acid encoding GNPE may be transiently- or stably-expressed in the modified cells of the invention. In one aspect, at least one nucleic acid encoding GNPE is transiently-expressed. In another aspect, at least one nucleic acid encoding GNPE is stably-expressed in the modified cells.

The location of the nucleic acid encoding GNPE is not critical, as it may be located on an expression vector comprising a nucleic acid encoding the nucleic acid, such as a plasmid, or it may reside on other types of expression vectors, such as recombinant viruses, or on transposons that facilitate integration of the nucleic acid into the genetic material present in the cell. In one aspect of the invention, at least one nucleic acid encoding GNPE is stably-integrated into the genome of said modified cell.

In another aspect of the invention, the cell which is modified to contain at least one nucleic acid encoding GNPE is further modified to comprise and express at least one nucleic acid encoding a polypeptide selected from the group consisting of (a) sialic acid-9-phosphate synthase (SAS) [Neu5Ac-9P synthetase, NANS], which is capable of converting ManNAc-6-P to N-acetylneuraminate-9-P (Neu5Ac-9P); (b) sialic acid-9-P phosphatase [Neu5Ac-9P phosphatase, NANP], which is capable of converting N-acetylneuraminate-9-P (Neu5Ac-9P) to N-acetylneuraminate (Neu5Ac); (c) cytidine 5'-monophosphate sialic acid synthetase (CSAS), which is capable of converting N-acetylneuraminate (Neu5Ac) to CMP-N-acetylneuraminate (CMP-Neu5Ac); (d) Golgi cytidine 5'-monophosphate sialic acid transporter (CSAT), which is capable of transporting CMP-N-acetylneuraminate (CMP-Neu5Ac) from the cytoplasm to the Golgi; (e) glycosyltransferase (GT), classified in enzyme class EC 2.4; (f) glycosylhydrolase (GH), classified in enzyme class EC 3.2.1; wherein each nucleic acid encoding a selected polypeptide is operably linked to a promoter functional in said cell; wherein at least one of said polypeptides is expressed, and the level of activity for at least one of said polypeptides in said cell is enhanced above the endogenous level of said activity in a parent cell lacking an introduced nucleic acid encoding at least one of said polypeptides.

In a related aspect, the glycosyltransferase is capable of transferring a monosaccharide moiety from an activated nucleotide sugar donor to a glycoconjugate. In another aspect, the glycosyltransferase is selected from the group consisting of N-acetylglucosaminyltransferase, galactosyltransferase, and N-acetylgalactosaminyltransferase.

In a related aspect, the glycosyltransferase is a sialyltransferase belonging to enzyme class EC 2.4.29. In another aspect, the sialyltransferase is capable of transferring a sialic acid from the activated nucleotide sugar donor CMP-sialic acid to a glycoconjugate. In still another aspect, the sialyltransferase is selected from the group consisting of α2,3 sialyltransferase, α2,6 sialyltransferase, and α2,8 sialyltransferase.

In a related aspect, the glycosylhydrolase is capable of hydrolyzing the glycosidic linkage of a glycoconjugate. In another aspect, the glycosylhydrolase is capable of hydrolyzing the glycosidic linkage of a glycoconjugate comprising the sialic acid moiety Neu5Ac. In still another aspect, the glycosylhydrolase is selected from the group consisting of glucosidase and mannosidase. In still another aspect, the mannosidase is human Golgi mannosidase II.

In one aspect, the GNPE-modified cell is modified to further comprise and express at least two nucleic acids encoding different polypeptides selected from the group consisting of SAS, NANP, CSAS, CSAT, ST, GT, and GH. In an alternate aspect, none of the nucleic acids encoding different polypeptides selected from the group consisting of GNPE, SAS, NANP, CSAS, CSAT, ST, GT, and GH, are stably-integrated into the genome of the doubly-modified cell. In a different aspect, at least one of the nucleic acids encoding different polypeptides selected from the group consisting of GNPE, SAS, NANP, CSAS, CSAT, ST, GT, and GH, is stably-integrated into the genome of said cell. In still another aspect, all of the nucleic acids encoding different polypeptides selected from the group consisting of GNPE, SAS, NANP, CSAS, CSAT, ST, GT, and GH, are stably-integrated into the genome of said cell.

In one aspect, the GNPE-modified cell belongs to a domain selected from the group consisting of Bacteria and Eukaryota. In another aspect, the domain is Eukaryota and the kingdom is selected from the group consisting of Animals, Fungi and Plants. In another aspect, the kingdom is animal, and the animal cell may be a mammalian cell or an insect cell.

The source of the GNPE nucleic acid can vary. In one aspect, the modified cell contains a nucleic acid encoding a polypeptide capable of converting GlcNAc-6-P to ManNAc-6-P which is derived from a source selected from the domain consisting of Bacteria. In another aspect, the nucleic acid is derived from a bacterial source, selected from a genus consisting of *Escherichia, Shigella, Enterobacter* and *Salmonella*. In still another aspect, the nucleic acid is derived from *Escherichia coli*.

In many cases, it is desirable to create modified cells, where the GNPE nucleic acid is derived from a source that is Bacteria, and the domain of the cell is Eukaryota. In other aspects of the invention, the cell is a plant cell, fungal cell, or an animal cell. The animal cell may be a mammalian cell or an insect cell.

Another aspect includes a GNPE-modified cell, wherein the polypeptide capable of converting GlcNAc-6-P to ManNAc-6-P is: (a) a polypeptide represented by SEQ ID NO: 6; (b) a variant polypeptide thereof that contains conservative amino acid substitutions in which GNPE structure and function are conserved; or (c) a truncated or fusion polypeptide thereof in which GNPE function is conserved. In one aspect, the modified cell is a plant, fungal, or an animal cell. In another aspect, the cell is an animal cell, which may be an insect cell. In another aspect, the insect cell is a lepidopteran insect cell. In still another aspect, the lepidopteran insect cells are from a genus selected from the group consisting of *Lymantria, Helicoverpa, Heliothis, Mamestra, Malocosoma, Leucania, Trichoplusia, Anticarsia, Spodoptera, Manduca, Choristoneura, Bombyx,* or *Estigmene*.

In another aspect, the insect cell is a dipteran cell. In still another aspect, the dipteran cell is a *Drosophila* cell.

In another aspect, the animal cell is a mammalian cell. In still another aspect, the mammalian cell is selected from the group consisting of CHO cells, HEK cells, MDCK cells, Vero cells, HeLa cells, SP2/0 cells, Jurkat cells, NS0 cells, Per.C6 cells, 3T3 cells, BHK cells, or COS cells.

In another aspect, the GNPE-modified cell is a fungal cell. In one aspect, the fungal cell is in a genus selected from the group consisting of *Pichia, Saccharomyces, Hansenula, Kluyveromyces, Candida, Aspergillus, Trichoderma, Chrysosporium, Fusarium,* and *Neurospora*. In still another aspect, the fungal cell is in a genus and species selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Saccharomyces cerevisiae, Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa*.

In another aspect, the GNPE-modified cell forms part of an insect organism. In still another aspect, the insect organism is a lepidopteran insect larva from a genus selected from the group consisting of *Lymantria, Helicoverpa, Heliothis, Mamestra, Malocosoma, Leucania, Trichoplusia, Anticarsia, Spodoptera, Manduca, Choristoneura, Bombyx,* or *Estigmene*.

Related aspects include a GNPE-modified cell, wherein the polypeptide capable of converting GlcNAc-6-P to ManNAc-6-P is: (a) a polypeptide represented by SEQ ID NO: 6; (b) a variant polypeptide thereof that contains conservative amino acid substitutions in which GNPE structure and function are conserved; or (c) a truncated or fusion polypeptide thereof in which GNPE function is conserved.

In one aspect, the GNPE-modified cell has at least one nucleic acid encoding GNPE on an expression vector comprising said nucleic acid. There are many types of expression vectors, which are typically derived from replicons that function in one or more cell types. In one aspect, the expression vector is a plasmid, and in another aspect, the expression vector is a virus. An expression vector may comprise a mobile genetic segment called a transposon, which contains the genetic elements responsible for expression of the desired nucleic acid product or products, plus regulatory elements that encode or facilitate the transposition of the transposon to genetic material to other locations within the cell, such as from plasmid or virus to the chromosome, from plasmid to virus or virus to plasmid, or from chromosome to plasmid or virus. In one aspect, the transposon is selected from the group consisting of piggyBac, Sleeping Beauty (SB), Tn7, Tn5, Tn916, Tcl/mariner, Minos and S elements, Quetzal elements, Txr elements, maT, most, Himarl, Hermes, Tol2 element, Pokey, P-element, and Tc3.

In another aspect, the expression vector is a shuttle vector, which is capable of replication and/or expression in two or more distinct cell types. In one aspect, the shuttle vector is capable of replication in bacterial and in eukaryotic host cells. In another aspect, the expression vector is capable of replication in one distinct cell type, but can express different nucleic acids under the control of distinct promoters in different cell types. BacMam vectors, for example, which are derived from baculoviruses such as the widely-used *Autographa californica* nuclear polyhedrosis virus (AcNPV), can replicate and express many nucleic acids in insect cells, but cannot replicate in mammalian cells, although they can express specific nucleic acids in mammalian cells when the specific nucleic acid of interest is regulated by a promoter that is operable in mammalian cells.

Another aspect of the invention relates to a method for converting N-acetyl-D-glucosamine-6-phosphate (GlcNAc-6-P) to N-acetyl-D-mannosamine-6-phosphate (ManNAc-6-P) in a cell, said method comprising the steps of: (a) introducing into said cell at least one nucleic acid encoding a polypeptide capable of converting N-acetyl-D-glucosamine-6-phosphate (GlcNAc-6-P) to N-acetyl-D-mannosamine-6-phosphate (ManNAc-6-P), wherein each nucleic acid is operably linked to a promoter functional in said cell; and (b) expressing at least one nucleic acid encoding a polypeptide capable of converting N-acetyl-D-glucosamine-6-phosphate (GlcNAc-6-P) to N-acetyl-D-mannosamine-6-phosphate (ManNAc-6-P). Related aspects include a method wherein at least one of said polypeptides is expressed, and the level of activity for conversion of GlcNAc-6-P to ManNAc-6-P in said cell is enhanced above the endogenous level of said activity in a parent cell lacking an introduced nucleic acid encoding at least one of said polypeptides.

One aspect of the invention is a method for converting N-acetyl-D-glucosamine-6-phosphate (GlcNAc-6-P) to CMP-N-acetylneuraminate (CMP-Neu5Ac) in a cell, said method comprising the steps of (a) introducing into said cell, in any order: (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetyl-neuraminate-9-P to N-acetylneuraminate; (iv) at least one nucleic acid encoding a polypeptide capable of converting N-acetylneuraminate to CMP-N-acetylneuraminate; wherein each of said nucleic acids are operably-linked to a promoter which is functional in said cell; and (b) expressing each of the introduced nucleic acids such that the level of CMP-N-acetylneuraminate in said cell is enhanced above the endogenous level of CMP-N-acetylneuraminate in a parent cell lacking one or more of said nucleic acids.

One aspect of the invention is a method for preparing a cell which is modified to comprise and express nucleic acids encoding one or more polypeptides capable of converting N-acetyl-D-glucosamine-6-phosphate (GlcNAc-6-P) to CMP-N-acetylneuraminate (CMP-Neu5Ac) in a cell, said method comprising the steps of (a) introducing into said cell, in any order: (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetyl-neuraminate-9-P to N-acetylneuraminate; (iv) at least one nucleic acid encoding a polypeptide capable of converting N-acetylneuraminate to CMP-N-acetylneuraminate; wherein each of said nucleic acids are operably-linked to a promoter which is functional in said cell. Another aspect is a method wherein the method of introducing at least one of said nucleic acids into said cell is selected from the group consisting of transformation, transfection, or infection.

One aspect of the invention is a method of producing a sialylated glycoprotein in a modified cell comprising the steps of: (a) introducing an expression vector comprising a nucleic acid encoding a recombinant protein into a modified cell, wherein said cell comprises (i) at least one nucleic acid encoding a polypeptide capable of converting N-acetyl-D-glucosamine-6-phosphate (GlcNAc-6-P) to N-acetyl-D-mannosamine-6-phosphate (ManNAc-6-P); and zero or more of the following: (ii) at least one nucleic acid encoding a polypeptide capable of converting ManNAc-6-P to N-acetylneuraminate-9-P; (iii) at least one nucleic acid encoding a polypeptide capable of converting N-acetylneuraminate-9-P to N-acetylneuraminate; (iv) at least one nucleic acid encoding a polypeptide capable of converting N-acetylneuraminate to CMP-N-acetylneuraminate; wherein each nucleic acid is operably linked to a promoter functional in said cell; (b) expressing the nucleic acid encoding said recombinant protein; and (c) isolating the sialylated glycoprotein from the modified cells or from cell culture medium obtained from the modified cells. Another aspect is a method wherein said cell further comprises one or more of the following: (v) at least one nucleic acid encoding a Golgi cytidine 5'-monophosphate sialic acid transporter (CSAT), which is capable of transporting CMP-N-acetylneuraminate (CMP-Neu5Ac) from the cytoplasm to the Golgi; (vi) at least one nucleic acid encoding a glycosyltransferase (GT), classified in enzyme class EC 2.4, that transfers sugars to a glycoconjugate; (vii) at least one nucleic acid encoding a glycosylhydrolase (GH), classified in enzyme class EC 3.2.1, that hydrolyzes sugars from a glycoconjugate; wherein each nucleic acid is operably linked to a promoter functional in said cell. Still another aspect is a method wherein said glycosyltransferase is selected from the group consisting of N-acetylglucosaminyltransferase, galactosyltransferase, and N-acetylgalactosaminyltransferase. Still another aspect is a method wherein said glycosyltransferase is a sialyltransferase belonging to enzyme class EC 2.4.29. Still another aspect is a method wherein said sialyltransferase is selected from the group consisting of α2,3 sialyltransferase, α2,6 sialyltransferase, and α2,8 sialyltransferase. Another aspect is a method wherein said glycosylhydrolase is selected from the group consisting of glucosidase and mannosidase.

A variety of methods can be used to introduce nucleic acids comprising nucleic acids or regulatory elements into cells. These include chemical modification of cells with reagents, such as liposomes, or inorganic salts, such as calcium phosphate, which facilitate permeabilization of the cells or coat the nucleic acids with partially-charged molecules that facilitate the transfer of the coated material by endogenous membrane transport systems. Physical systems, such as bombardment of cells with nucleic acids attached to solid or metal particles, such as gold, can also be used. In other cases, the nucleic acids comprising the nucleic acids of interest are in viral particles that are taken up by the cell by natural viral uncoating/cellular transport systems. In one aspect of the invention, the method of introducing at least one of said nucleic acids into said cell is selected from the group consisting of transformation, transfection, and infection.

In some host cell systems, it is desirable to include additional nucleic acids to enhance the ability of modified cells to produce a sialylated glycoconjugate. Endogenous or native nucleic acids encoding polypeptides with various functions in sugar processing, such as nucleotide sugar transporters, glycosyltransferases, sialyltransferases, and glycosylhydrolases, may be absent or function at insufficient levels during periods when a desirable heterologous protein is expressed, resulting in the production of suboptimal glycoforms of the desirable protein, such as non-glycosylated protein, partially-glycosylated protein, and proteins with incompletely processed glycans. Including one or more additional nucleic acids, that encode for example nucleotide sugar transporters such as the CMP-sialic acid transporter (CSAT), glycosyltransferases (GT) such as N-acetyl-, galactosyl-, and N-acetylgalactosaminyl-transferases, sialyltransferases (ST) such as α2,3-, α2,6-, and α2,8-sialyltransferases, and glycosylhydrolases (GH) such as mannosidases and glucosidases, in the engineered host cells may be used to overcome these deficiencies. Those skilled in the art of cell engineering will recognize that specific host cells may need some, but not all, of the nucleic acid products listed above to efficiently produce sialylated glycoconjugates in the modified cells, while other cell types may require all of the listed nucleic acid products to work effectively in a glycoconjugate production system. In many cases, the biochemical nature of the glycoconjugate being expressed dictates the requirement for specific host cell functions. In some cases, it may be appropriate to reduce the expression of specific host nucleic acids that are involved in metabolic pathways that result in undesirable forms of the sialylated glycoconjugate. Those nucleic acids could be inactivated by deletion, targeted insertions, or substitutions with segments of DNA encoding polypeptides having a lower activity or a different cellular function. It may also be desirable to modify the level of expression of a particular nucleic acid by using a promoter that results in higher or lower levels of expression than is achieved by using the HR5 enhancer-IE1 promoter combination described herein, or to substitute a promoter that can be modulated under various cellular or media conditions so that production of the most desirable glycoconjugate is optimized.

One aspect of the invention is a method for producing a transgenic insect larva comprising in at least some of its somatic or germ cells at least one nucleic acid encoding a polypeptide capable of converting N-acetyl-D-glucosamine-6-phosphate (GlcNAc-6-P) to N-acetyl-D-mannosamine-6-phosphate (ManNAc-6-P) comprising the steps of: (a) introducing a nucleic acid encoding GNPE into a larval cell, wherein said nucleic acid is operably-linked to a promoter functional in said cell, and (b) growing the larva under conditions wherein said GNPE nucleic acid is expressed, and GNPE activity is above endogenous levels of activity in a larva lacking said nucleic acid. Another aspect is a method further comprising the step of introducing at least one of the following nucleic acids into a larval cell: (i) at least one nucleic acid encoding a polypeptide capable of converting ManNAc-6-P to N-acetylneuraminate-9-P; (ii) at least one nucleic acid encoding a polypeptide capable of converting N-acetyl-neuraminate-9-P to N-acetylneuraminate; (iii) at least one nucleic acid encoding a polypeptide capable of converting N-acetylneuraminate to CMP-N-acetylneuraminate; wherein each of said nucleic acids are operably-linked to a promoter which is functional in said cell. Still another aspect is a method further comprising the step of introducing at least one of the following nucleic acids into a larval cell: (iv) at least one nucleic acid encoding a Golgi cytidine 5'-monophosphate sialic acid transporter (CSAT), which is capable of transporting CMP-N-acetylneuraminate (CMP-Neu5Ac) from the cytoplasm to the Golgi; (v) at least one nucleic acid encoding a glycosyltransferase (GT), classified in enzyme class EC 2.4; (vi) at least one nucleic acid encoding a glycosylhydrolase (GH), classified in enzyme class EC 3.2.1; wherein each nucleic acid is operably linked to a promoter functional in said cell. Still another aspect is a method wherein at least one nucleic acid introduced into said larval cell is on an expression vector comprising said nucleic acid. Other aspects include variations wherein said expression vectors used in this method is a plasmid, a virus, or a comprises a transposon.

Another aspect of the invention includes a transgenic insect larva produced by the method and its variations described immediately above.

Another aspect includes a method of producing a sialylated glycoconjugate in any of the transgenic insect larva described immediately above comprising the steps of: (a) introducing an expression vector comprising a nucleic acid encoding a recombinant protein into the transgenic larva; (b) expressing the nucleic acid encoding said recombinant protein; and (c) isolating the sialylated glycoconjugate from the transgenic larva.

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

EXAMPLES

The foregoing discussion may be better understood in connection with the following representative examples which are presented for purposes of illustrating the principle methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods Sources of Materials

All parts are by weight (e.g., % w/w), and temperatures are in degrees centigrade (° C.), unless otherwise indicated. Table E-1 presents a summary of the PCR primers and nucleotide and amino acid sequences described in this application.

TABLE E-1

Table of Sequences

| Name | Description | Length | Type | SEQ ID NO: |
|---|---|---|---|---|
| NanE Forward primer 1 | GCG GCC GCA CCA TGT CGT TAC TTG CAC AAC | 30 | ssDNA | 1 |
| NanE Reverse primer 1 | ATG CGG CCG CTC ATA GCA CCG CCT TTT TC | 29 | ssDNA | 2 |
| NanE Forward primer 2 | GCG GCC GCA CCA TGT CGT T | 19 | ssDNA | 3 |
| NanE Reverse primer 2 | ATG CGG CCG CTC ATA GCA C | 19 | ssDNA | 4 |
| E. coli NanE gene encoding GlcNAc-6P 2' epimerase | 711 bp DNA fragment comprising the 690 bp open reading frame of the E. coli NanE gene with 5' and 3' flanking NotI restriction sites | 711 | DNA | 5 |
| E. coli Nane gene product, GlcNAc-6P 2' epimerase | 229 amino acid polypeptide encoded by E. coli NanE gene having GlcNAc-6P 2' epimerase activity | 229 | Protein | 6 |

Protocols for GNE Gene Isolation and GNPE Vector Construction

Genomic DNA isolated from E. coli K12 cells was used as the template in a polymerase chain reaction to amplify the E. coli NanE gene and add restriction sites. Approximately 1 ng of template DNA, 5 µl 10× Thermopol buffer (New England Biolabs, Ipswich, Mass.), 0.2 µl Taq DNA polymerase, 200 uM of each dNTP, and 50 pmol of NanE forward primer 1 (SEQ ID NO: 1) and NanE reverse primer 1 (SEQ ID NO: 2) in a 50 µl final volume reaction were cycled as follows: 20 s at 95° C., and five times the following three-step cycle: 15 s at 50° C., 45 s at 72° C., and 15 sec at 95° C. One pi of the NanE forward primer 2 (SEQ ID NO: 3) and NanE reverse primer 2 (SEQ ID NO: 4), both at a concentration of 50 uM, were then added to the reaction. The reaction was then cycled as follows: 20 s at 95° C., and thirty times the following three-step cycle: 15 s at 58° C., 45 s at 72° C., and 15 sec at 95° C. The reaction products were then separated by agarose gel electrophoresis, and a 711 bp PCR product was excised from the gel, and the DNA isolated using a commercial kit (Qiaquick, Qiagen, Valencia, Calif.). Two μl of the purified DNA was cloned into the pCR®2.1TOPO® vector (Invitrogen, Carlsbad, Calif.) according to the manufacturer's instructions. The reaction mixture was used to transform Top10 competent cells (Invitrogen, Carlsbad, Calif.) according to the manufacturer's instructions. A clone encoding the correct polypeptide was identified by DNA sequencing, and the NanE gene was excised using the restriction enzyme NotI (New England Biolabs) from the plasmid, and subcloned into the NotI site of the pIE1HR3 plasmid (Jarvis et al., 1996), which comprises the IE1 promoter with the HR5 enhancer to allow for expression of a downstream gene, using standard molecular biology techniques. A plasmid with the NanE gene in the correct orientation was identified using restriction analysis, and designated pIE1HR3-EcGNPE. Large-scale plasmid DNA was prepared using alkaline lysis, followed by cesium chloride density gradient centrifugation using standard molecular biology techniques.

TABLE E-2

Bacterial strains

| Designation | Relevant Genotype | Reference | Source |
|---|---|---|---|
| TOP10 | F-mcrA Δ(mrr-hsdRMS-mcrBC) Φ80lacZΔM15 ΔlacX74 recA1 araD139 Δ(araleu) 7697 galU galK rpsL (Str$^R$) endA1 nupG | | Invitrogen, Carlsbad, CA |

TABLE E-3

Plasmids

| Designation | Markers | Size (bp) | Description | Reference | Source |
|---|---|---|---|---|---|
| pCR ® 2.1TOPO ® | Amp$^R$, Kan$^R$ | 3,931 | Vector for cloning PCR products having single 3' A-overhangs | — | Invitrogen, Carlsbad, CA |
| pIE1HR3 | Amp$^R$ | 5021 | Insect expression vector, comprising the AcNPV IE1 promoter in conjunction with the AcNPV HR5 enhancer, that can be used to express various genes | Jarvis et al., 1996 | |
| pIE1HR3-EcGNPE | Amp$^R$ | 5709 | pIE1HR3, comprising amplified *E. coli* gene encoding GNPE | | This study |
| pIE1-Hygro | Amp$^R$ Hygro$^R$ | 6047 | Selectable marker conferring Hygromycin resistance to insect cells | Hollister and Jarvis, 2001 | |
| pIE1-SAS | Amp$^R$ | 6133 | Insect expression vector encoding mouse SAS | — | |
| pIE1-CSAS | Amp$^R$ | 6366 | Insect expression vector encoding mouse CSAS | — | |
| pIE1HR3-hCSAT | Amp$^R$ | 6009 | Insect expression vector encoding human CSAT | — | |
| pIE1GlcNAcTII | Amp$^R$ | 6458 | Insect expression vector encoding human N-acetylglucosaminyl-transferase 2 | Hollister et al., 2001 | |
| pIE1HRGalT | Amp$^R$ | 6521 | Insect expression vector encoding bovine β1,4 galactosyltransferase I | Hollister et al., 1997 | |
| pIE1HR4 Hs ST3GalIVb | Amp$^R$ | 6010 | Insect expression vector encoding human ST3GalIV sialyltransferase | — | |
| pIE1ST6 | Amp$^R$ | 6233 | Insect expression vector encoding rat ST6GalI sialyltransferase | Hollister and Jarvis, 2001 | |

TABLE E-4

Description and sources of cloned genes

| Designation | Full Name | Origin | GenBank Accession No. | Reference | Source |
|---|---|---|---|---|---|
| GNPE | GlcNAc-6-P 2'-epimerase | *Escherichia coli* K12 | NP_417690.1 | Ringenberg et al., 2003 | This study |
| Hyg | Hygromycin phosphotransferase | *Escherichia coli* | ADW79766.1 | Gritz and Davies, 1983 | — |
| SAS | Sialic scid-9-phosphate synthase | Mouse | NP_444409.1 | Nakata et al., 2000 | Obtained from IMAGE consortium/ Invitrogen |

TABLE E-4-continued

Description and sources of cloned genes

| Designation | Full Name | Origin | GenBank Accession No. | Reference | Source |
|---|---|---|---|---|---|
| CSAS | CMP-sialic acid synthetase | Mouse | NP_034038.2 | Münster et al., 1998 | Obtained from IMAGE consortium/Invitrogen |
| CSAT | CMP-sialic acid transporter | Human | NP_006407.1 | Ishida et al., 1998 | Obtained from Origene Inc. |
| GlcNAcTII | N-acetylglucosaminyl-transferase II | Human | NP_002399.1 | Tan et al., 1995 | Obtained from Harry Schachter |
| β1,4GalTI | β1,4 Galactosyltransferase I | Bovine | B4GT1_BOVIN | Russo et al., 1990 | Obtained from Joel Nancy Shaper |
| ST3GalIVb | α2,3 sialyltransferase | Human | SIA4C_HUMAN | Sasaki et al., 1993 | Obtained from Open Biosystems |
| ST6GalI | α2,6 sialyltransferase | Rat | SIAT1_RAT | Weinstein et al., 1987 | Obtained from James Paulson |

TABLE E-5

Features of Engineered Lepidopteran Insect Cell Lines

| Cell line | Description | Reference |
|---|---|---|
| Sf9 | Clonal cell line originally derived from *Spodoptera frugiperda* (fall armyworm) pupal ovary cells | Vaughn et al., 1977 |
| Sfβ4GalT | Sf9 cells comprising a gene encoding bovine β4GalT1 operably-linked to an AcNPV IE1 promoter (pIE1) | Hollister et al., 1998 |
| Sfβ4GalT/ST6 | Sf9 cells comprising genes encoding bovine β4GalT1 and rat ST6Gal1 operably-linked to pIE1 | Hollister and Jarvis, 2001 |
| SfSWT-1 | Sf9 cells comprising genes encoding human GlcNAcTI and GlcNAc-TII, bovine β4GalT1, rat ST6Gal1, and mouse ST3Gal4 operably-linked to pIE1 | Hollister et al., 2002 |
| SfSWT-3 | SfSWT-1 cells with additional genes encoding mouse SAS and mouse CSAS operably-linked to pIE1 | Aumiller et al., 2003 |
| SfSWT-20 | Sf9 cells comprising genes encoding *E. coli* GNPE, mouse SAS, mouse CSAS, human CSAT, human GlcNAc TII, bovine β4GalT1, and human ST3Gal IVb operably-linked to pIE1 | This study |
| SfSWT-21 | Sf9 cells comprising genes encoding *E. coli* GNPE, mouse SAS, mouse CSAS, human CSAT, human GlcNAc TII, bovine β4GalT1, and rat ST6Gal I operably-linked to pIE1 | This study |

TABLE E-6

Polypeptides that are similar to *E. coli* GNPE

| Source | Protein (Da) | % Identity | GenBank Accession Number | Reference |
|---|---|---|---|---|
| *Escherichia coli* str. K-12 substr. MG1655 | 24074 | 100 | NP_417690 | Ringenberg et al., 2003 |
| *Shigella dysenteriae* 1012 | 24060 | 99 | ZP_03066739.1 | — |
| *Shigella flexneri* 2a str. 2457T | 24088 | 99 | NP_838725.1 | — |
| *Shigella sonnei* Ss046 | 24102 | 99 | YP_312172.1 | — |
| *Escherichia albertii* TW07627 | 24094 | 98 | ZP_02900344.1 | — |
| *Citrobacter rodentium* ICC168 | 24153 | 86 | YP_003368005.1 | — |
| *Enterobacter aerogenes* KCTC 2190 | 24189 | 83 | YP_004590863.1 | — |
| *Salmonella enterica* subsp. *enterica* serovar Choleraesuis str. SC-B67 | 24016 | 81 | YP_218262.1 | — |
| *Enterobacter cancerogenus* ATCC 35316 | 25139 | 74 | ZP_05970527.1 | — |
| *Klebsiella pneumoniae* NTUH-K2044 | 24544 | 77 | YP_002921468.1 | — |
| *Klebsiella aerogenes* | 24618 | 77 | NANE_ENTAE | — |

TABLE E-6-continued

Polypeptides that are similar to *E. coli* GNPE

| Source | Protein (Da) | % Identity | GenBank Accession Number | Reference |
|---|---|---|---|---|
| *Edwardsiella tarda* EIB202 | 25126 | 74 | YP_003294579.1 | — |
| *Providencia rettgeri* DSM 1131 | 24966 | 66 | ZP_06125104.1 | — |
| *Proteus mirabilis* HI4320 | 25016 | 64 | YP_002152679.1 | — |
| *Haemophilus parainfluenzae* ATCC 33392 | 30179 | 64 | ZP_08148042.1 | — |
| *Mannheimia haemolytica* serotype A2 str. BOVINE | 24183 | 63 | ZP_05988342.1 | — |
| *Vibrio fischeri* ES114 | 26334 | 60 | YP_204049.1 | — |
| *Aggregatibacter aphrophilus* NJ8700 | 24912 | 63 | YP_003007045.1 | — |
| *Actinobacillus minor* 202 | 24778 | 62 | ZP_05629099.1 | — |
| *Pasteurella dagmatis* ATCC 43325 | 24607 | 63 | ZP_05919155.1 | — |
| *Haemophilus influenzae* NT127 | 24324 | 62 | ZP_05850153.1 | — |
| *Pasteurella multocida* subsp. *multocida* str. Pm70 | 24315 | 62 | NP_246650.1 | — |
| *Gallibacterium anatis* UMN179 | 24062 | 61 | YP_004421166.1 | — |
| *Photobacterium damselae* subsp. *damselae* CIP 102761 | 24747 | 60 | ZP_06155711.1 | — |
| *Vibrio cholerae* 623-39 | 25025 | 57 | ZP_01981255 | — |
| *Psychromonas* sp. CNPT3 | 24956 | 59 | ZP_01215428.1 | — |
| *Yersinia rohdei* ATCC 43380 | 26451 | 62 | ZP_04613515.1 | — |
| *Shewanella pealeana* ATCC 700345 | 26424 | 59 | YP_001501379.1 | — |
| *Brucella* sp. BO1 | 52435 | 54 | ZP_07478244.1 | — |
| *Mesorhizobium ciceri* biovar *biserrulae* WSM1271 | 52988 | 55 | YP_004141807.1 | — |
| *Oceanicola granulosus* HTCC2516 | 22854 | 57 | ZP_01156625.1 | — |
| *Deinococcus geothermalis* DSM 11300 | 23975 | 46 | YP_593903.1 | — |
| *Paenibacillus polymyxa* E681 | 25437 | 47 | YP_003868763.1 | — |
| *Bacillus coagulans* 36D1 | 23638 | 46 | ZP_04432016.1 | — |
| *Centipeda periodontii* DSM 2778 | 24312 | 44 | ZP_08500936.1 | — |
| *Propionibacterium acnes* HL037PA2 | 25483 | 43 | EFS73846.1 | — |
| *Clostridium perfringens* | 24168 | 42 | AF130859_1 | Walters et al., 1999 |
| *Clostridium difficile* NAP08 | 24679 | 40 | ZP_06892100.1 | — |
| *Listeria monocytogenes* str. 1/2a F6854 | 24707 | 42 | ZP_00234021.1 | — |
| *Streptococcus pneumoniae* CGSP14 | 25812 | 41 | YP_001835566.1 | — |
| *Staphylococcus pseudintermedius* ED99 | 24422 | 42 | ADX77449.1 | — |
| *Streptomyces ghanaensis* ATCC 14672 | 25998 | 39 | ZP_06575634.1 | — |

Generation of Cell Lines

SfSWT-20 and SfSWT-21 cell lines were produced by co-transfecting Sf9 insect cells (Vaughn et al., 1977) with eight immediate early expression plasmids (Jarvis et al., 1996), each encoding the genes listed in Table E-5, plus an immediate early expression plasmid pIE1-Hygro (Hollister and Jarvis, 2001), encoding a bacterial hygromycin phosphotransferase gene (5 µg of each plasmid). In the experiments described below, all of the plasmids were introduced into the cells at the same time. The order and number in which genes are introduced into the cells is not critical, nor is the method of introducing nucleic acids encoding the desired gene products into the cells. The genes can also be introduced one at time in serial fashion, or in groups of two or more to produce modified cells. Some of the genes may be stably integrated into the genome of the cell, while others may be transiently expressed, or expressed during the course of infection by a viral vector comprising the desired genes.

Approximately $4 \times 10^6$ Sf9 cells were seeded in a 25 cm² cell culture flask in 5 mL of TNMFH medium supplemented with 10% fetal calf serum (cTNMFH) and allowed to attach at 28° C. for 30 minutes. The cells were washed twice with Grace's medium supplemented with 10% fetal calf serum (cGrace's) and covered with 750 µL of cGrace's. The plasmids were mixed in a test tube, incubated at 65° C. for 10 minutes, and 750 µL of transfection buffer (25 mM Hepes, 140 mM NaCl, 125 mM CaCl2, pH 7.10) were added. The plasmid mixture was then added to the cells and the culture flask was incubated on a rocking platform for 2 hours at 28° C. The transfection mixture was removed, the cells were washed twice with cTNMFH, and 5 mL of cTNMFH was added. After two days of incubation at 28° C., the medium was removed and replaced by an equal volume of cTNMFH containing 0.4 µg/mL of hygromycin. After another day, the cells were transferred into a 75 cm2 flask and another 10 mL of medium containing hygromycin were added. Three days later, the cells were transferred to a 100-mL DeLong flask (Corning Glass Works, Corning, N.Y.) containing 25 mL of fresh cTNMFH and incubated at 28° C. at 125 rpm in a Model 4580 rotary platform shaker-incubator (Forma Scientific, Inc., Marietta, Ohio). The cells were subsequently subcultured twice weekly at a seeding density of $1.5 \times 106$ cells/mL in 50 mL of Protein Sciences Formulary Medium (PSFM; Protein Sciences Corporation, Meriden, Conn.) in 100-mL DeLong flasks.

Sialic Acid Assays

Samples of SfSWT-20 and SfSWT-21 cells were cultured in cTNMFH medium supplemented with 10 fetal bovine serum to a density of approximately $1 \times 10^6$ cells/ml in 100-ml DeLong flasks (Corning Glass Works, Corning, N.Y.) at 28° C. and 125 rpm in a model 4580 rotary platform shaker-incubator (Forma Scientific, Inc., Marietta, Ohio). A volume of cells containing $1.5 \times 10^6$ cells was transferred to microcentrifuge tubes in duplicates. Cells were pelleted by centrifugation at 500×G, the supernatant was aspirated, cells were resuspended in PBS (pH 7.4), pelleted again, and the supernatant was aspirated. 150 µL 1% SDS was added to the cells and the mixture was vortexed. The lysate was cleared by centrifugation at 13,000×G in a microcentrifuge for 15 minutes.

The lysate was assayed in triplicate for sialic acid by a modified thiobarbituric acid assay. Briefly, 100 μL of the lysate was transferred to a borosilicate glass tube, to which 55 μL of sodium periodate solution was added (0.2 M NaIO$_4$ in 57% concentrated phosphoric acid). Samples were collected by centrifugation for 30 seconds at 3000×G in a GPR centrifuge (Beckman, Palo Alto, Calif.) and briefly vortexed, followed by an incubation of 1 hour at room temperature. 550 μL of 10% sodium arsenite (10% sodium arsenite with 0.5M sodium sulfate in 0.1 M sulfuric acid) was added while vortexing. Samples were collected by centrifugation for 30 seconds at 3000×G in a GPR centrifuge, followed by an overnight incubation at 4° C. Next, 1650 μL of TBA reagent (0.5 M NaSO$_4$, 0.6% 2-thiobarbituric acid, pH 9) was added slowly while vortexing. Samples were incubated for 1 hour at room temperature, briefly vortexed and placed in a water bath at 80° C. for 1 hour. Tubes were cooled in a 25° C. water bath, after which 750 μL cyclohexanone was added, followed by vigorous vortexing. The phases were separated by centrifugation for 30 seconds at 3000×G in a GPR centrifuge. Absorbance of the organic phase was read at 549 nm, and readings were absorbance readings were converted to micromoles of sialic acid according to the formula (0.75×A)/57.

The lysates were assayed in duplicate for protein concentration (BCA Protein Assay Kit Pierce, Rockford, Ill.). Briefly, 10 μL of cell lysate was assayed with 200 μL working reagent. For protein concentration standards, 10 μL of standard solution was assayed with 200 μL working reagent. The assay samples were incubated along with standards at 55° C. until sufficient color had developed. 180 μL of the reactions were then transferred into a well of a 96 well plate. Readings were taken at 560 nm and converted to concentrations by comparison to known standards.

Impact of GlcNAc Supplementation on Cellular Sialic Acid Concentration

Approximately 3×10$^6$ cells were seeded per well in a 6 well plate (Corning Costar, N.Y., NYS) in 2 mls of PSFM medium (Protein Sciences Corporation, Meriden, Conn.) and allowed to attach at 28° C. for 1 hour. The medium was aspirated and replaced with 2 mls of PSFM medium or PSFM medium supplemented with 10 mM N-acetyl-D-glucosamine. Cells were subsequently incubated for 24 hours at 28° C. The medium was aspirated and cells were washed twice with 1 ml of HEPES buffered saline (10 mM HEPES, 150 mM pH 7.5, 1 mM CaCl$_2$, 1 mM MgCl$_2$, 1 mM MnCl$_2$, 0.08% NaN$_3$). 400 μL 1% SDS were added to the cells, and the lysate was collected in a 1.6 mL microcentrifuge tube and vortexed. The lysate was cleared by centrifugation at 13,000×G in a microcentrifuge for 15 minutes. The lysates were then assayed for sialic acid and protein concentration as described above.

Lectin Cell Surface Staining

Cells were grown in PSFM medium (Protein Sciences Corporation, Meriden, Conn.) (SfSWT-20 and -21) or ESF-921 (Expression Systems LLC, Woodland, Calif.) (Sf9) to a density of approximately 4×10$^6$ cells/ml. Cells were diluted in PSFM medium to 1.5×10$^6$ cells/ml, and 2 mls of cell suspension was seeded per well in a 6 well plate (Corning Costar, N.Y., NYS) and allowed to attach at 28° C. for 1 hour.

For MAL staining, the medium was aspirated and cells were subsequently washed twice with 1 ml of HEPES buffered saline (HBS, 10 mM HEPES, 150 mM pH 7.5, 0.08% NaN$_3$). Cells were then incubated at 4° C. for 5 minutes in 1000 μL of HBS. Subsequently, cells were incubated at 4° C. for 30 minutes in 750 μL of HBS with 5 μg/ml biotinylated MAL-I lectin (Vector laboratories, Burlingame, Calif.). The lectin solution was aspirated and cells were washed twice with 1 ml of HBS. Cells were then incubated at 4° C. for 5 minutes in 750 μL of HBS with 5 μg/ml streptavidin—Texas Red conjugate (Vector labs). The solution was aspirated and cells were washed twice with 1 ml of HBS, after which cells were imaged using an Olympus FSX-100 microscope. The settings were: 20× magnification, 1/100 sec exposure phase contrast, 1/5 sec exposure red fluorescence channel, level compensation identical for all red fluorescence pictures, neutral density filter off, transmission LED 50%.

For SNA staining, the medium was aspirated and cells were subsequently washed twice with 1 ml of HBS with cations (1 mM each of CaCl$_2$, MgCl$_2$, MnCl$_2$). Cells were then incubated at 4° C. for 5 minutes in 750 μL of HBS with cations and 5 μg/ml biotinylated SNA lectin (Vector labs). The solution was aspirated and cells were washed twice with 1 ml of HBS with cations. Cells were then incubated at 4° C. for 5 minutes in 750 μL of HBS with cations and 5 μg/ml streptavidin-Texas Red conjugate. The solution was aspirated and cells were washed twice with 1 ml of HBS with cations, after which cells were imaged using an Olympus FSX-100 microscope. The settings were: 20× magnification, 1/100 sec exposure phase contrast, 1/10 sec exposure red fluorescence channel, no level compensation, neutral density filter off, transmission LED 50%.

Example 1

Generation and Initial Characterization of Novel Insect Cell Lines Expressing GNPE and Other Genes for Sialic Acid Biosynthesis and Utilization As described above, the *E. coli* NanE gene encoding GNPE was amplified by PCR and cloned as a NotI fragment in to pCR® 2.1TOPO® where its orientation and sequence was confirmed. The NotI fragment was then inserted into pIE1HR3 to produce pIE1HR3-GNPE, where the GNPE gene is operably-linked to the IE1 promoter of the *Autographa californica* nuclear polyhedrosis virus.

To evaluate the impact of GNPE expression on glycoconjugate sialylation, insect cells were engineered to contain the GNPE gene and a repertoire of higher eukaryotic genes encoding enzymes involved in glycoconjugate sialylation, including SAS (Nakata et al., 2000), CSAS (Münster et al., 1998), CMP-sialic acid transporter (Ishida et al., 1998), N-acetylglucosaminyltransferase II (Tan et al., 1995), β1,4-galactosyltransferase (Shaper et al., 1986) and either α2,3 sialyltransferase (ST3GalIV, Sasaki et al., 1993, cell line designation: SfSWT-20) or α2,6 sialyltransferase (ST6GalI, Wen et al., 1992, cell line designation: SfSWT-21). The resulting cell lines allowed them to produce sialic acid without ManNAc supplementation, and to use the endogenously produced sialic acid, to sialylate newly-synthesized N-glycoproteins.

Figure 11:
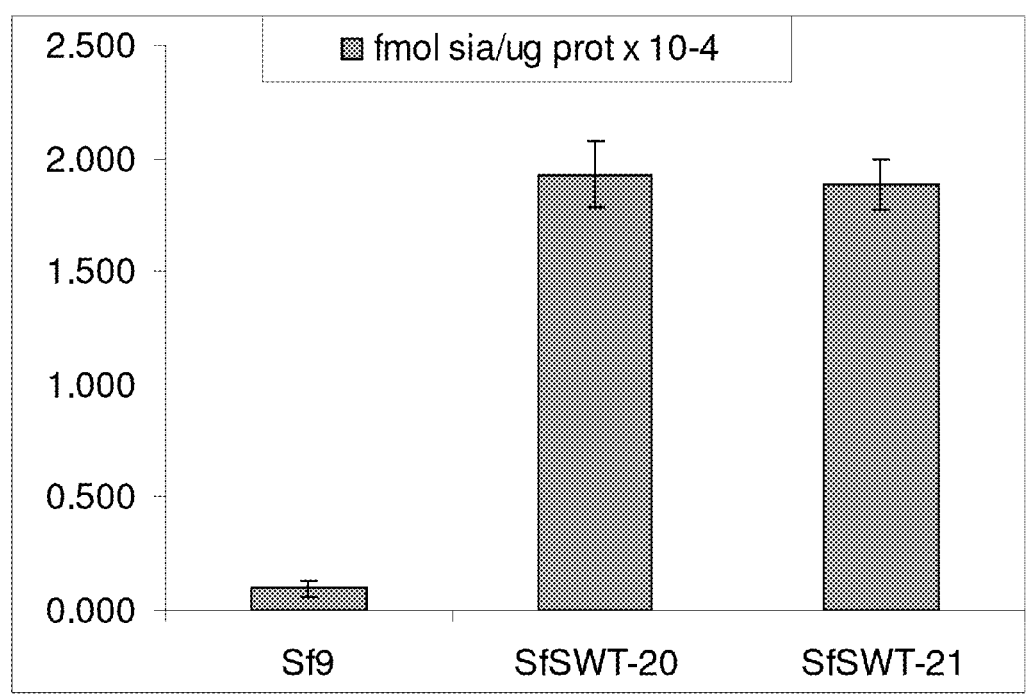
FIG. 11 sets forth sialic acid levels in SfSWT-20 and SfSWT-21 insect cells that are glycoengineered to express the *Escherichia coli* GNPE as well as suite of other glycosylation enzymes involved in sialoglycoprotein production.

FIG. 11 demonstrates that SfSWT-20 and SfSWT-21 cell lines are able to produce sialic acid when grown in serum-free medium without supplementation of ManNAc. Previous work has shown repeatedly that insect cells expressing a SAS fail to produce sialic acid, unless grown in culture medium supplemented with ManNAc (Lawrence et al., 2000; Aumiller et al., 2003; Viswanathan et al., 2003; Hill et al., 2006). Thus, expression of GNPE and SAS allows insect cells to produce sialic acid without ManNAc supplementation.

Figure 12:
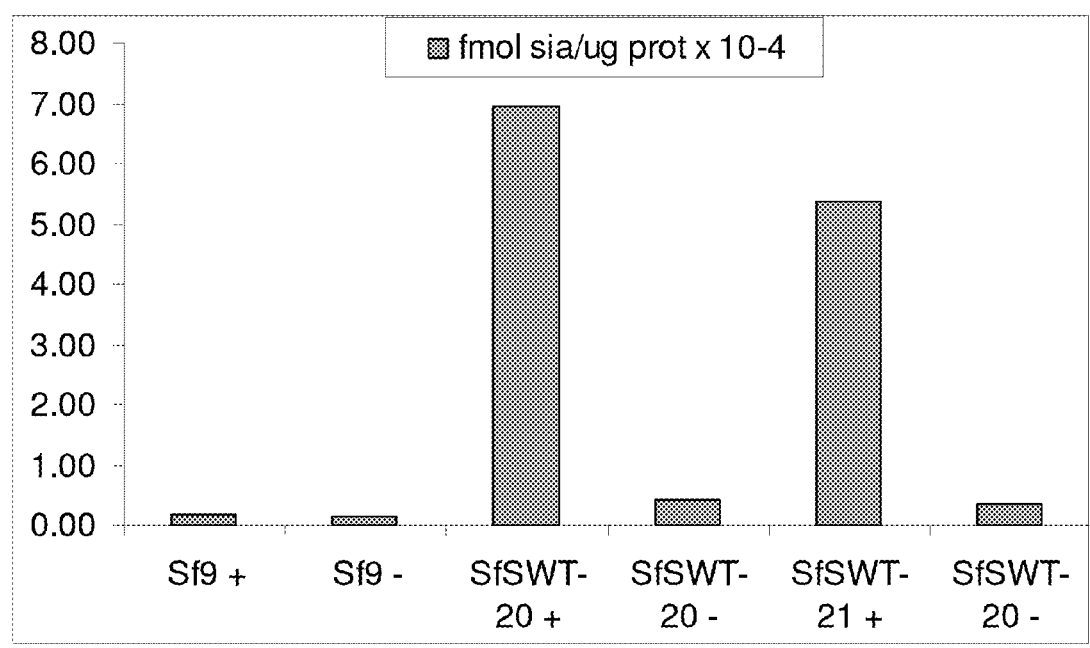
FIG. 12 sets forth sialic acid levels in SfSWT-20 and SfSWT-21 insect cells that are glycoengineered to express the *Escherichia coli* GNPE as well as suite of other glycosylation enzymes involved in sialoglycoprotein production.

FIG. 12 demonstrates that SfSWT-20 and SfSWT-21 cell lines are able to produce even higher levels of sialic acid when grown in serum-free medium with supplementation of GlcNAc. Sialic acid levels increased approximately 15- to 16-fold when SfSWT-20 and SfSWT-21 cells were fed 10 mM N-acetyl-D-glucosamine for 24 hours in the cell culture medium. These data show that insect cells expressing both GNPE and SAS can take up GlcNAc from the cell culture medium, and transform it into sialic acid. Thus, pools of sialic acid in cells expressing GNPE and SAS enzyme can be increased further by supplementing the cell culture media with GlcNAc, which is far cheaper that ManNAc.

Figure 13:
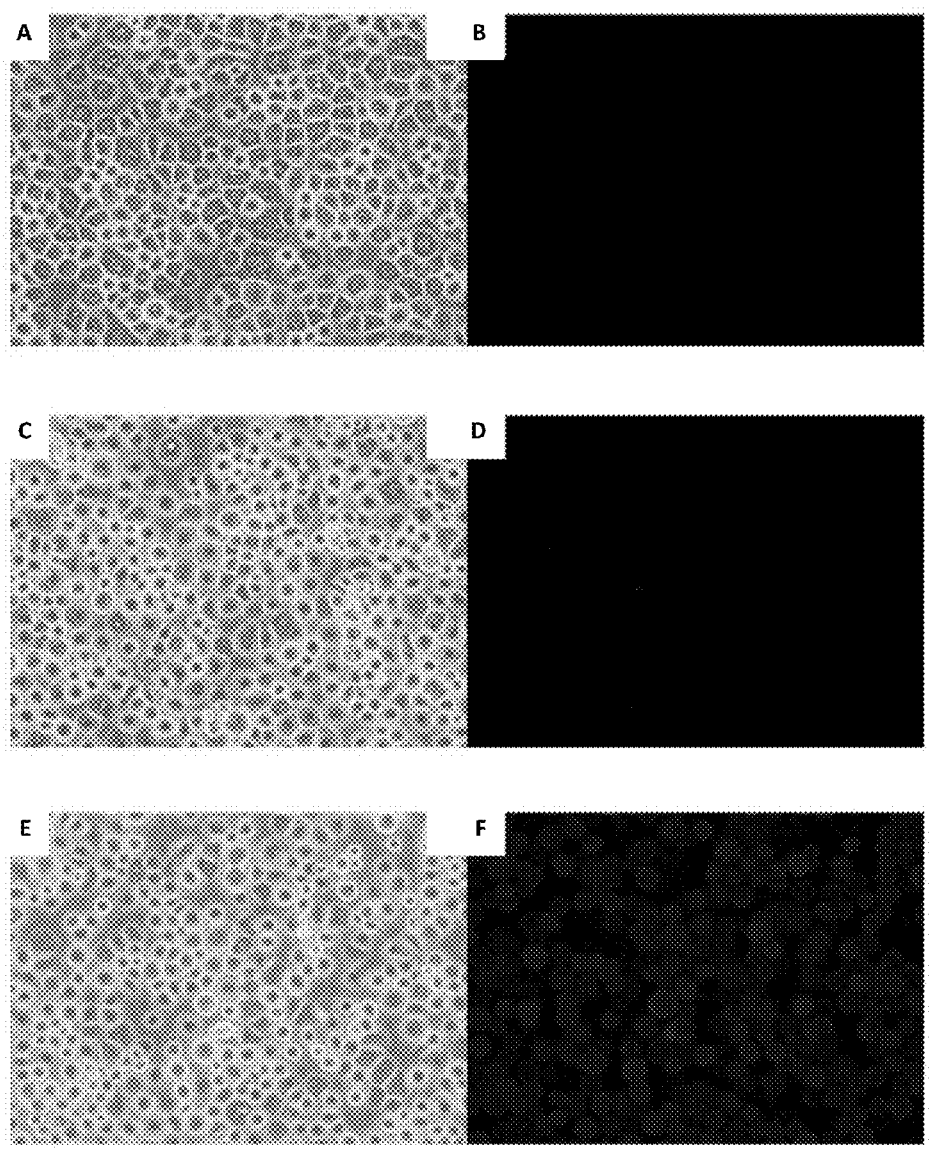
Figure 14:
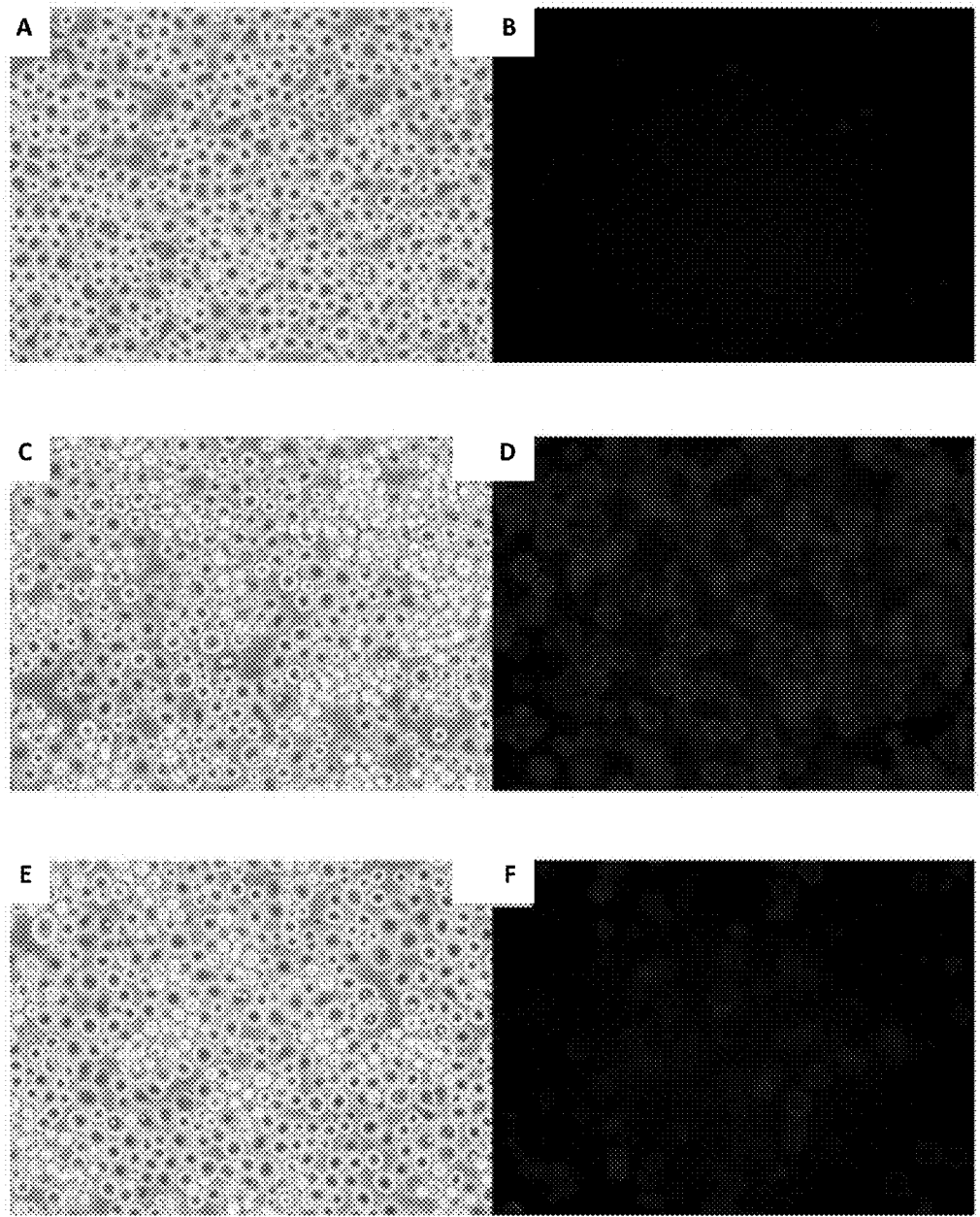

FIGS. 13 and 14 demonstrate that SfSWT-20 and SfSWT-21 cells can produce sialylated glycoconjugates on their cell surface without ManNAc supplementation. These data show that insect cells expressing a GNPE, a SAS, and other enzymes required to produce sialylated glycans can utilize the sialic acid precursor ManNAc-6-P produced by the GNPE enzyme to produce sialylglycoconjugates with α2,6 linked sialic acids (in cells expressing an α2,6-sialyltransferase) or α2,3 linked sialic acids (in cells expressing an α2,3-sialyltransferase).

Figure 15:
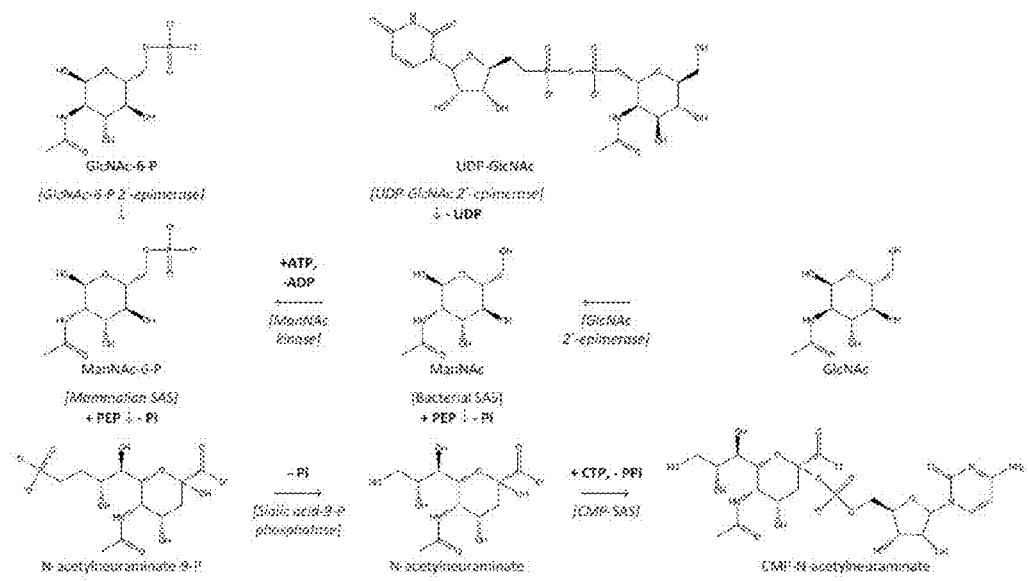

FIG. 15 sets forth key pathways in the synthesis of CMP-N-acetylneuraminate (CMP-sialic acid), showing the structures of key intermediates.

Figure 16:
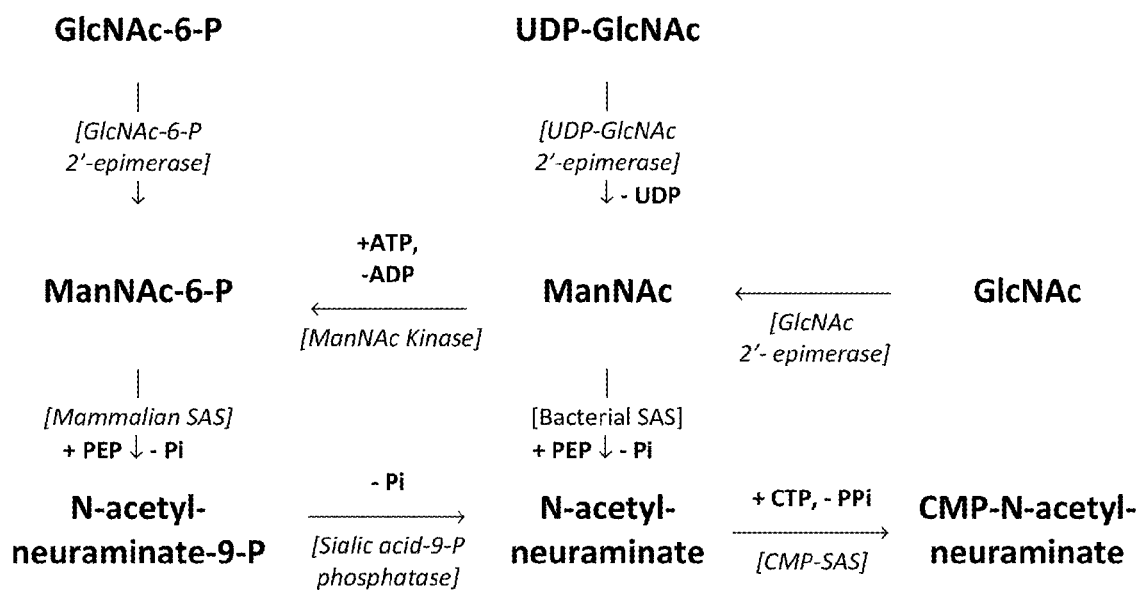

FIG. 16 sets forth key pathways in the synthesis of CMP-N-acetylneuraminate (CMP-Sialic Acid), without showing the structures of key intermediates.

Figure 17:
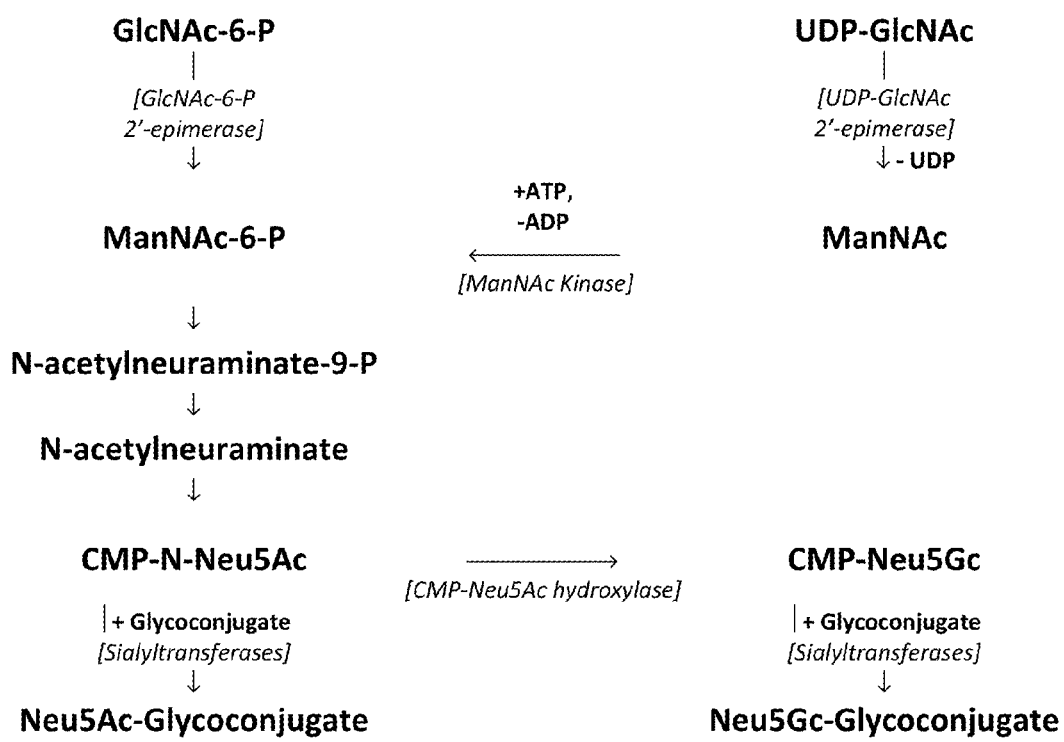

FIG. 17 sets forth key pathways in the synthesis of sialylated glycoconjugates from CMP-Neu5Ac and CMP-Neu5Gc, without showing the structures of key intermediates.

Example 2

Extending the Characterization of Insect Cell Lines Expressing GNPE and Other Genes for Sialic Acid Biosynthesis and Utilization General Materials and Methods Sources of Materials All parts are by weight (e.g., % w/w), and temperatures are in degrees centigrade (° C.), unless otherwise indicated.

Immediate Early Expression Plasmids

The transgenic insect cells described in this example were produced using several immediate early expression plasmids, which can be used to constitutively express foreign genes in uninfected insect cells under the transcriptional control of the baculovirus ie1 promoter and hr5 enhancer elements (Table E2-1; Jarvis et al., 1990, Jarvis et al., 1996. pIE1Hygro, pIE1GlcNAcTII, pIE1HRGalT, pIE1ST6, and pIE1-hCSAT are described in the references given in Table E2-1. pIE1MmSAS and pIE1MmCSAS are new immediate early expression plasmids encoding mouse SAS (GenBank Acc. No. BC003307) and CSAS (GenBank Acc. No. BE689556), respectively. Finally, pIE1EcGNPE is a new immediate early expression plasmid encoding E. coli K12 GNPE (GenBank Acc. No. AP012306.1 nucleotides 2838888-2838199). The structures of each of the plasmids used in this study were verified by restriction mapping and/or nucleotide sequencing and each was extracted from a culture of the relevant E. coli strain using the alkaline lysis method and purified by equilibrium ultracentrifugation in continuous CsCl-EtBr density gradients, as described previously (Sambrook et al., 1989).

TABLE E2-1

Genes used for insect cell glycoengineering in this study

| Plasmid | Enzyme | HGNC* Abbreviation | Species | Reference |
|---|---|---|---|---|
| pIE1HREcGNPE | GlcNAc-6-P 2'-epimerase | GNPE | E. coli | This study |
| pIE1HRMmSAS | Sialic acid-9-P synthase | SAS | Mouse | This study |
| None | Sialic acid-9-P phosphatase | NANP | Endogenous | Not applicable |
| pIE1HRMmCSAS | Sialic acid synthetase | CMAS | Mouse | This study |
| pIE1-hCSAT | Golgi CMP-sialic acid transporter | CMAT | Human | Mabashi-Asazuma et al, submitted |
| pIE1GlcNAcTII | N-acetylglucosaminyltransferase II | MGAT2 | Human | Hollister et al., 2002 |
| pIE1HRGalT | β1-4 galactosyltransferase | B4GALT1 | Bovine | Hollister et al., 1998 |
| pIE1ST6 | α2-6 sialyltransferase | ST6GAL1 | Rat | Hollister and Jarvis, 2001 |
| pIE1Hygro | Hygromycin phosphotransferase | Hygro | E. coli | Hollister and Jarvis, 2001 |

*Human Gene Nomenclature Committee (Seal et al., 2011)

Insect Cells, Cell Culture, and Viruses

ExpresSF+ (Protein Sciences Corporation, Meriden, Conn.) and SfSWT-19 and -21 (this study) cells were routinely maintained as shake flask cultures at 125 rpm and 28° C. in Protein Sciences Fortified Medium (PSFM; Protein Sciences Corporation) at densities ranging from 0.5 to 6.0 million cells/mL. For media supplementation experiments, PSFM was supplemented with 200 μM peracetylated ManNAc ($Ac_4$ManNAc) in lieu of ManNAc because the peracetylated form is more readily taken up by cells (Jones et al., 2004) and, therefore, can be used at much lower concentrations.

SfSWT-19 and SfWT-21 are transgenic variants of expresSF+ cells that were isolated in this study. Briefly, expresSF+ cells were transfected with immediate early expression plasmid DNA mixtures using a modified calcium phosphate method and selected in PSFM containing 1 mg/mL hygromycin, as described previously (Harrison and Jarvis, 2007a; Harrison and Jarvis, 2007b). The plasmid DNA mixtures used to produce SfSWT-19 and SfSWT-21 cells included 5 µg each of pIE1HRGlcNAcTII, pIE1HRGalT, pIE1HRST6, pIE1mSAS, pIE1mCSAS, pIE1-hCSAT, and pIE1Hygro. In addition, the mixture used to produce SfSWT-21 cells included 5 µg of pIE1EcGNPE.

cells were washed with lectin buffer (10 mM HEPES pH 7.5, containing 150 mM NaCl, 0.08% $NaN_3$, and 1 mM each of $CaCl_2$, $MgCl_2$, and $MnCl_2$), covered with the same buffer, and incubated for 10 min at 4° C. The buffer was then removed and the cells were incubated with fresh lectin buffer containing 10 µg/mL of FITC-conjugated Concanavalin A (ConA) or *Sambucus nigra* agglutinin (SNA) for 10 min at 4° C. Each of the FITC-conjugated lectins was purchased from Vector Laboratories (Burlingame, Calif.). After this incubation period, the lectins were removed and the cells were washed twice with fresh lectin buffer, covered with the same, and imaged using an Olympus FSX-100 microscope (Tokyo, Japan) with identical exposures for all samples.

TABLE E2-2

Features of Engineered Lepidopteran Insect Cell Lines

| Cell line | Description | Notes | Reference |
|---|---|---|---|
| SfSWT-19 | Sf9 cells comprising nucleic acids encoding mouse SAS, mouse CSAS, human CSAT, human GlcNAc TII, bovine β4GalT1, and human ST3Gal IVb all independently and operably-linked to pIE1 | Constructed from plasmids comprising nucleic acids encoding 6 transgenic glycosylation enzymes plus a hygromycin selectable marker | This study |
| SfSWT-21 | Sf9 cells comprising nucleic acids encoding *E. coli* GNPE, mouse SAS, mouse CSAS, human CSAT, human GlcNAc TII, bovine β4GalT1, and rat ST6Gal I all independently and operably-linked to pIE1 | Independently-constructed from the same plasmids as SfSWT-19, plus a plasmid comprising a nucleic acid encoding *E. coli* GNPE | This study |

Human erythropoietin (hEPO) and a murine IgG2a-Fc were used to assess the recombinant glycoprotein sialylation capabilities of the new transgenic insect cell lines isolated for this study. We used these molecules as models for this study because EPO and recombinant antibodies represent the lion's share of the recombinant glycoprotein biologics market (Walsh, 2010). AchEPO-His is a recombinant baculovirus encoding a C-terminally 6×-HIS-tagged version of hEPO, as described previously (H. Mabashi-Asazuma, X. Shi, C. Geisler, and D. L. Jarvis, submitted for publication). AcmIgG2a-Fc is a recombinant baculovirus encoding an N-terminally 8×-HIS-tagged version of the soluble domain of a mouse IgG2a-Fc fragment (GenBank Acc. No. S37483; amino acids 237-469). This recombinant baculovirus was produced using Gateway® technology with a pENTR™/D-TOPO® TA (Life Technologies Corporation, Grand Island, N.Y.) entry vector kindly provided by Dr. Henrik Olson (GlikNik, Baltimore, Md.) and a modified baculovirus destination vector, Ac6.9-GT, previously isolated in our lab (Toth et al., 2011). The spent LR reaction was used to transfect expresSF+ cells, as described above, the transfected cells were cultured in PSFM containing ganciclovir to select against the parental (Ac6.9-GT) virus, and then viral progeny were resolved by plaque assay, as described previously (Toth et al., 2011). A recombinant virus identified by its white plaque phenotype was amplified, characterized, and then a working virus stock was prepared, titered by plaque assay, and used for the remainder of this study, as described previously (Summers and Smith, 1987).

Cell Surface Staining

Insect cells were seeded into 6-well plates at a density of $1×10^6$ cells/well in PSFM with or without 200 µM peracetylated ManNAc ($Ac_4ManNAc$; New Zealand Pharmaceuticals). After 24 h at 28° C., the media were removed and the Recombinant Glycoprotein Expression and Purification Insect cells were seeded into 50 mL shake flask cultures at a density of $2×10^6$ cells/mL in PSFM medium and infected with AchEPO-His or AcmIgG2a-Fc at a multiplicity of infection of about 2 plaque-forming units/cell. After a 1 h adsorption period, the cells were pelleted by centrifugation at 200×g for 5 min, resuspended in PSFM supplemented with antibiotics (1.25 µg/mL amphotericin B and 25 µg/mL gentamicin) and with or without 200 µM $Ac_4ManNAc$, transferred to fresh shake flasks, and incubated for 48 h. The cultures were then harvested and cells and debris were removed by centrifugation at 1,000×g for 10 min at 4° C. The supernatants were harvested and budded virus particles were removed by ultracentrifugation at 100,000×g for 30 min at 4° C. mIgG2a-Fc supernatants were dialyzed in 12-14 kDa molecular weight cut off membranes (Spectrum Labs, Rancho-Dominguez, Calif.) against 0.05 M $Na_2HPO_4$ (pH 7.5) containing 0.5 M NaCl. hEPO-His supernatants were buffer-exchanged on a Sephadex G25 column equilibrated with 10 mM Tris (pH 7.5) containing 0.5 M NaCl. Subsequently, each protein was affinity-purified using ProBond nickel affinity resin (Life Technologies) according to the manufacturer's instructions and, after elution with 10 mM Tris (pH 7.5) containing 0.5 M NaCl and 0.5 M imidazole, each was desalted on Sephadex G25 columns equilibrated with 50 mM Tris (pH 7.5) containing 0.15 M NaCl. Finally, each protein was concentrated using an Amicon® Ultra-4 centrifugal filter with a 5 kDa molecular weight cutoff (EMD-Millipore; Merck, Darmstadt, Germany).

Sialic Acid and CMP-Sialic Acid Determinations

Sialic acid and CMP-sialic acid determinations were performed using AchEPO-His-infected cells in order to assess sialic acid metabolism and recombinant hEPO-HIS sialylation in parallel. Cell pellets were isolated from AchEPO-His-infected cell cultures as described in section 2.4, washed once with phosphate buffered saline (pH 7.4), and then SDS was added to a final concentration of 1% (w/v), the cell suspension was vortexed, and the DNA was sheared by repeatedly passaging the extracts through a 22 ga syringe. Triplicate 100 µL aliquots of these cell extracts were used to measure the total sialic acid and CMP-sialic acid content in a modified thiobarbituric acid assay. CMP-sialic acid content was measured independently using a separate set of triplicate 100 µL aliquots of the same extracts after treatment with 7.5 µL of 10% (w/v) $NaBH_4$ to destroy the free sialic acids. After adding 7.5 µL acetone and 55 µL of 0.2 M $NaIO_4$ in 57% concentrated $H_3PO_4$, the extracts were incubated for 1 h at room temperature, and then 0.55 mL of 0.1 M $H_2SO_4$ containing 10% (w/v) $NaAsO_2$ and 0.5 M $Na_2SO_4$ was added and the extracts were vortexed and incubated for another 10 min at room temperature. Finally, 1.65 mL of TBA reagent (0.5 M $Na_2SO_4$, 0.6% 2-thiobarbituric acid, pH 9) was added slowly with mixing and the extracts were incubated overnight at 4° C. The extracts were then transferred to an 80° C. water bath, incubated for 1 h, cooled in a 25° C. water bath, and then 0.75 mL of cyclohexanone was added, the extracts were vortexed vigorously, and the organic phase was used to measure absorbance at 549 and 532 nm. The number of picomoles of sialic acid or CMP-sialic acid in each sample was calculated by subtracting the absorbance contributed by the 2-deoxyribose chromophore using the formula $750\times(21\times A_{549}-7.6\times A_{532})$, as described previously (Warren, 1959). Triplicate samples of each lysate also were used to measure total protein concentrations in a commercial bicinchoninic acid assay with bovine serum albumin as the standard, according to the manufacturer's recommendations (Pierce, Rockford, Ill.). The final average sialic acid values obtained with the untreated extracts were presented as pmol sialic acid/µg total protein in FIG. 18A. The final average sialic acid values obtained with the $NaBH_4$-treated extracts were presented as pmol CMP-sialic acid/µg total protein in FIG. 18B.

Recombinant Glycoprotein Analyses

Protein concentrations were estimated by SDS-PAGE with Coomassie Brilliant Blue (CBB) staining by comparison to known amounts of bovine serum albumin (Sigma Aldrich, St. Louis, Mo.) run in adjacent lanes on the same gel. Replicate samples containing equal amounts of protein were then treated with buffer alone, *Flavobacterium meningosepticum* peptide:N-glycanase F (PNGase F; New England BioLabs, Ipswich, Mass.), or *Clostridium perfringens* neuraminidase (New England BioLabs), according to the manufacturer's instructions. Commercial human transferrin and bovine serum albumin (Sigma-Aldrich) were used as sialylated and non-glycosylated protein controls, respectively. After the appropriate treatment, each sample was resolved by SDS-PAGE with 12% (w/v) polyacrylamide gels, a gel containing one set of replicates was stained with CBB, and the other three were transferred to Immobilon-P PVDF membranes (Immobilon, Billerica, Mass.) for immunoblotting or lectin blotting assays, as described previously (Geisler and Jarvis, 2011). In the immunoblotting assays, mIgG2a-Fc was detected using alkaline phosphatase-conjugated goat anti-mouse IgG (Sigma) and hEPO was detected using rabbit anti-human EPO (U-CyTech, Utrecht, The Netherlands) and alkaline phosphatase-conjugated goat anti-rabbit IgG (Sigma). In the lectin blotting assays, mannose or sialic acid were detected using alkaline phosphatase-conjugated ConA or SNA, respectively, each of which was obtained from EY Laboratories (San Mateo, Calif.). Immunoblotting and lectin blotting signals were visualized using a standard alkaline phosphatase-based chromogenic detection method, as described previously (Leary et al., 1983).

Results

Glycoengineering the Baculovirus/Insect Cell System

Figure 6:
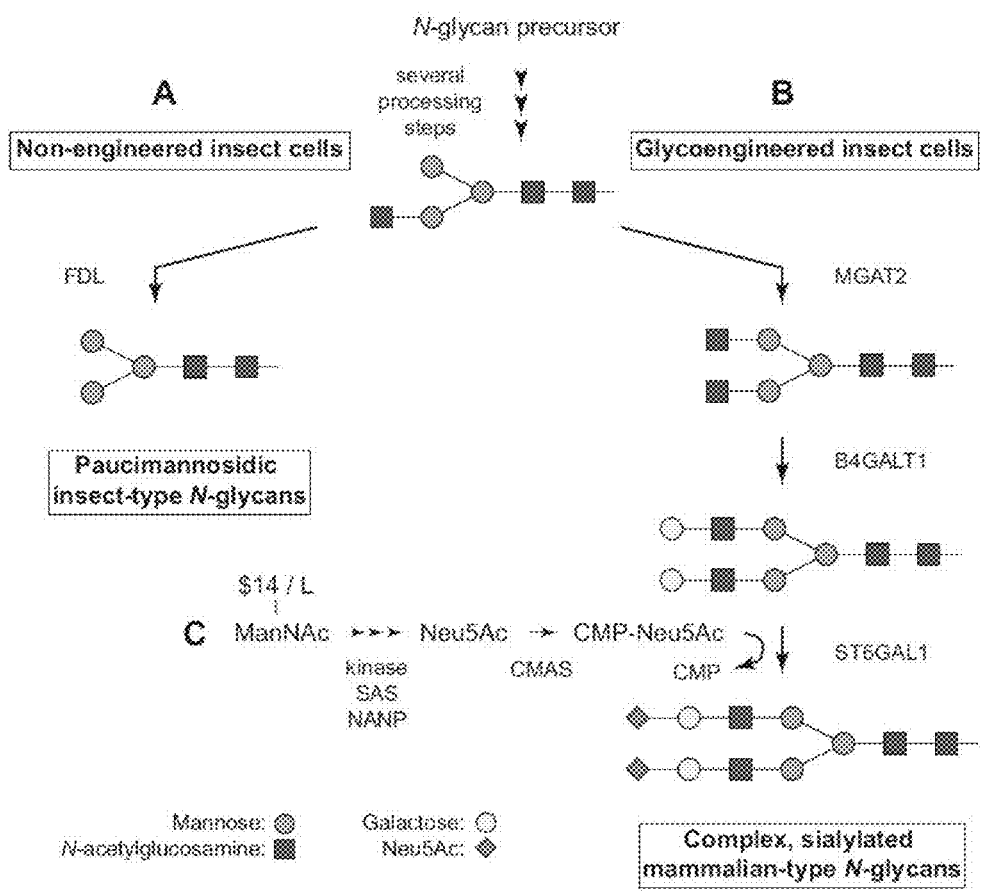
FIG. 6 sets forth recombinant protein glycosylation pathways in non-engineered and glycoengineered baculovirus/insect cell systems: (A) Non-glycoengineered baculovirus/insect cell systems can glycosylate newly synthesized proteins and process their N-glycans to produce trimmed, paucimannosidic structures. (B) Glycoengineered baculovirus/insect cell systems have extended N-glycan processing capabilities and can produce recombinant glycoproteins with complex, terminally sialylated N-glycans. (C) All glycoengineered baculovirus/insect cell systems described to date require media supplementation with ManNAc, an expensive sialic acid precursor, for efficient sialylation.

The most commonly used hosts for baculovirus-mediated recombinant glycoprotein production are established lepidopteran insect cell lines, such as IPLB-SF-21 (Sf21; Vaughn et al., 1977), Sf9 (Summers and Smith, 1987), expresSF+(Protein Sciences Corporation), and BTI Tn 5B1-4 (High Five™; Wickham et al., 1992). Each of these cell lines has metabolic pathways that support recombinant glycoprotein biosynthesis and processing. However, these insect cell pathways are simpler than the corresponding mammalian cell pathways and, as a result, none of these insect cell lines can produce recombinant glycoproteins with complex, terminally sialylated N-glycans (FIG. 6A). This problem has been addressed through glycoengineering efforts, in which mammalian genes have been incorporated into baculovirus expression vectors and/or lepidopteran insect cell lines (reviewed by Geisler and Jarvis, 2009; Harrison and Jarvis, 2006; Jarvis, 2009; Shi and Jarvis, 2007). These efforts have yielded modified baculovirus/insect cell systems with more extensive protein N-glycosylation pathways and the capacity to sialylate recombinant glycoproteins (FIG. 6B). However, as noted above, even the most extensively glycoengineered baculovirus/insect cell systems require supplementation with ManNAc for efficient sialylation (FIG. 6C), which increases media costs by at least 25%.

To determine if *E. coli* GNPE could be used to initiate sialic acid biosynthesis and overcome the ManNAc supplementation requirement, as hypothesized, we isolated a matched pair of transgenic expresSF+ cell derivatives designated SfSWT-19 and SfSWT-21. Each was genetically transformed in parallel with the suite of mammalian genes required to enable sialylated recombinant glycoprotein production in the presence of ManNAc, which included genes encoding N-acetylglucosaminyltransferase II, R4-galactosyltransferase I, α2,6-sialyltransferase I, SAS, CMAS, and a CMP-sialic acid transporter, together with a bacterial hygromycin phosphotransferase ($Hygro^R$) gene as the selectable marker, as described in Materials and methods. SfSWT-21, but not SfSWT-19 cells were additionally transformed with the *E. coli* GNPE gene. As detailed above, *E. coli* GNPE is normally involved in sialic acid degradation, but we hypothesized that this enzyme might drive the reverse reaction in insect cells, effectively converting pre-existing pools of GlcNAc-6-P to ManNAc-6-P, and initiating sialic acid biosynthesis in the absence of exogenous ManNAc.

After transfection and selection in growth media containing hygromycin B, we examined SfSWT-19 and -21 cells in preliminary cell surface SNA staining assays designed to detect the presence of sialylated glycoconjugates, as described in Materials and methods. The results showed that SNA intensely stained both SfSWT-19 and -21 cells that had been cultured in PSFM supplemented with $Ac_4ManNAc$ (data not shown). Despite being transformed with multiple unlinked markers, SNA stained virtually 100% of each cell type under these growth conditions, although there was variation in the staining intensities observed among individual cells (data not shown). Most importantly, SNA also intensely stained SfSWT-21 cells, which had been additionally transformed with the E. coli GNPE gene, when these cells were cultured in PSFM lacking Ac$_4$ManNAc. This preliminary result supported the hypothesis that E. coli GNPE could be used to circumvent the ManNAc supplementation requirement in glycoengineered expresSF+ cells and prompted us to examine the properties of SfSWT-19 and -21 cells in further detail.

Sialic Acid and CMP-Sialic Acid Production

Our first set of formalized experiments was designed to examine the ability of the transgenic insect cells to produce sialic acid and CMP-sialic acid when cultured in the presence or absence of ManNAc. These assays were performed using AchEPO-His-infected cells so that the results could be coupled with a subsequent assessment of recombinant hEPO sialylation. Hence, expresSF+, SfSWT-19, and SfSWT-21 cells were infected with AchEPO and cultured for 48 h in PSFM or PSFM supplemented with Ac$_4$ManNAc. The extracellular growth media were harvested and used to affinity-purify hEPO-His for lectin blotting assays (see below), and then the infected cell pellets were extracted and assayed for total sialic acid and CMP-sialic acid, as described in Materials and Methods.

Figure 18:
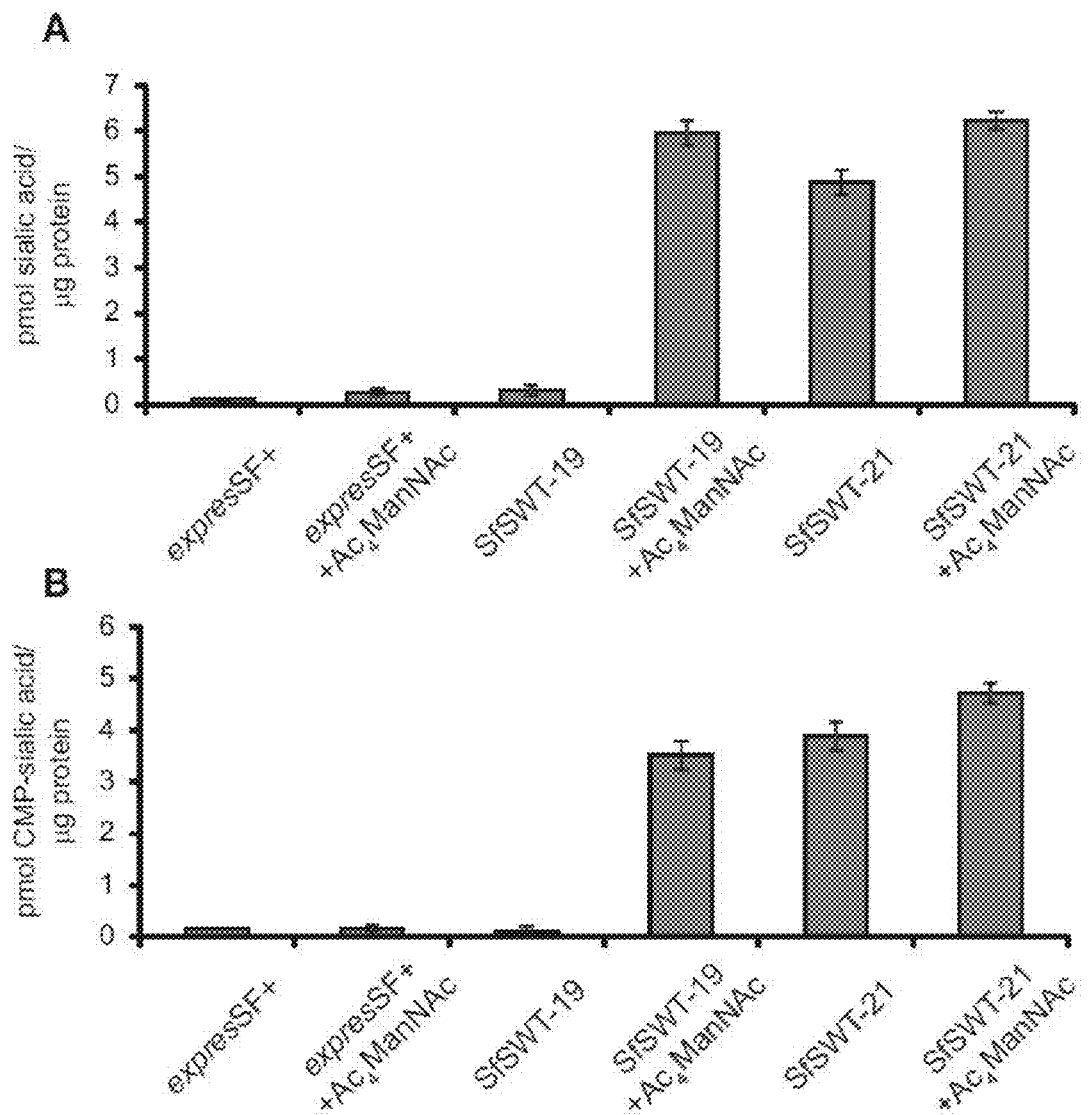

The results of these assays showed that expresSF+ cells cultured in the presence or absence of Ac$_4$ManNAc contained no detectable sialic acid (FIG. 18A). SfSWT-19 cells cultured in the absence of Ac$_4$ManNAc also contained no detectable sialic acid, but the same cells contained substantial amounts of sialic acid when cultured in the presence of Ac$_4$ManNAc. This was consistent with the fact that SfSWT-19 cells express mammalian SAS, which would convert ManNAc obtained from the growth medium to sialic acid. SfSWT-21 cells contained equally high amounts of sialic acid when cultured in the presence of Ac$_4$ManNAc, as expected. Strikingly, however, SfSWT-21 cells also contained high amounts of sialic acid when cultured in the absence of Ac$_4$ManNAc. Nearly identical results were obtained when CMP-sialic acid levels were measured in extracts of each cell type cultured in the presence or absence of ManNAc (FIG. 18B). In each case, the observed CMP-sialic acid content reflected the presence or absence of intracellular sialic acid (FIG. 18A) and the mammalian CMAS gene.

These results showed that E. coli GNPE can efficiently initiate sialic acid biosynthesis in insect cells cultured in medium lacking ManNAc and that ManNAc supplementation does not augment sialic acid or CMP-sialic acid levels in insect cells glycoengineered to express this enzyme. Thus, these results supported the hypothesis that the bacterial GNPE can be used to circumvent the ManNAc supplementation requirement for recombinant glycoprotein sialylation by glycoengineered insect cells.

Cell Surface Sialylation

Figure 19:
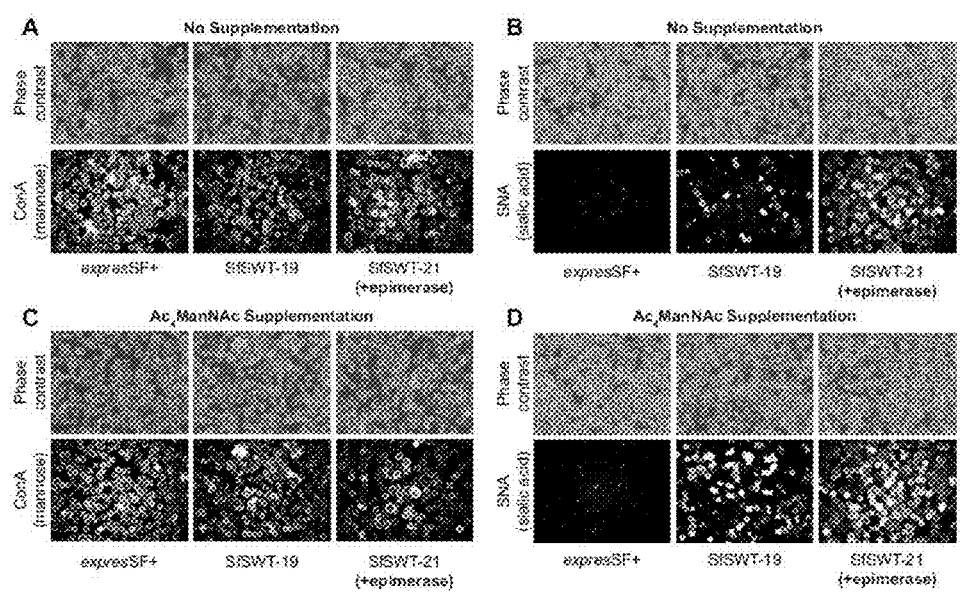

The next set of experiments was designed to determine if SfSWT-21 cells can sialylate endogenous glycoproteins in the absence of ManNAc supplementation. expresSF+, SfSWT-19, and SfSWT-21 cells were cultured for 24 h in PSFM with or without Ac$_4$ManNAc, and then cell surface staining assays were performed with ConA or SNA, as described in Materials and methods. ConA binds to mannose and, therefore, stains all cell surface N-glycoproteins irrespective of their N-glycan structures. SNA binds to terminal sialic acids and, therefore, stains only terminally sialylated cell surface glycoconjugates. The results of these assays showed that ConA intensely stained expresSF+, SfSWT-19, and SfSWT-21 cells cultured in PSFM with (FIG. 19C) or without Ac$_4$ManNAc (FIG. 19A), with no obvious differences in staining intensities among the different cell lines or culture conditions. This was consistent with the expectation that all three cell lines would display endogenous cell surface N-glycoproteins containing mannose under both culture conditions. SNA stained expresSF+ cells cultured under either condition at only very low, background levels (FIGS. 19B and 19D), which was expected because these cells cannot produce terminally sialylated glycoconjugates and were the negative controls for the SNA staining assays. In contrast, SNA intensely stained both SfSWT-19 and -21 cells cultured in PSFM supplemented with Ac$_4$ManNAc (FIG. 19D). This was expected because both had been glycoengineered with a suite of mammalian glycogenes known to support sialylate N-glycoprotein production in the presence of this sialic acid precursor. Most importantly, SNA stained SfSWT-21 cells cultured in PSFM with or without Ac$_4$ManNAc at about the same intensity, while this sialic acid-specific lectin stained SfSWT-19 cells grown in PSFM without Ac$_4$ManNAc at much lower levels (FIG. 19B).

These results indicated that E. coli GNPE can not only initiate sialic acid biosynthesis, but also can support glycoprotein sialylation in glycoengineered insect cells. Furthermore, the fact that there was no augmentation of cell surface sialylation with Ac$_4$ManNAc supplementation suggests that GNPE-mediated sialic acid production is not a bottleneck in glycoprotein sialylation by these cells. These results provided further support for the hypothesis that GNPE can circumvent the ManNAc supplementation requirement for recombinant glycoprotein sialylation by glycoengineered insect cells.

Recombinant Glucoprotein Sialylation

Finally, we directly examined the ability of E. coli GNPE to support recombinant glycoprotein sialylation by glycoengineered insect cells cultured without Ac$_4$ManNAc supplementation. expresSF+, SfSWT-19, and SfSWT-21 cells were infected with recombinant baculoviruses encoding HIS-tagged forms of mIgG2a-Fc or hEPO, the infected cells were cultured for 48 h in PSFM with or without Ac$_4$ManNAc, the recombinant glycoproteins were affinity purified, and their glycosylation patterns were compared in tightly controlled lectin blotting assays. One set of samples was stained with CBB to demonstrate that approximately equal amounts of purified protein had been loaded into each lane (FIGS. 20A and 21A). Another was used for immunoblotting with antibodies specific for mIgG or hEPO to verify their identities and document their banding patterns (FIGS. 20B and 21B). A third set was stained with ConA, the mannose-specific lectin, to identify the N-glycosylated forms of each purified recombinant protein (FIGS. 20C and 21C). Finally, a fourth set of samples was stained with SNA, the terminal sialic acid-specific lectin, to determine if the two different recombinant glycoproteins were sialylated when produced in the three different cell types under the two different growth conditions (FIGS. 20D and 21D).

The results of these experiments showed that expresSF+ cells failed to detectably sialylate either mIgG2a-Fc or hEPO when cultured in PSFM with or without Ac$_4$ManNAc. This was expected, as this parental cell line does not produce sialylated glycoproteins and was a negative control for the lectin blotting assays. SfSWT-19 cells also failed to detectably sialylate mIgG2a-Fc when cultured in PSFM. When cultured in PSFM supplemented with Ac$_4$ManNAc, SfSWT-19 cells sialylated this recombinant protein, albeit at low levels, as expected. SfSWT-21 cells cultured in PSFM with or without Ac$_4$ManNAc sialylated mIgG2a-Fc at a much higher level, with no augmentation in the presence of Ac$_4$ManNAc.

Unexpectedly, SfSWT-19 cells sialylated hEPO at low levels when cultured in PSFM without Ac$_4$ManNAc. The addition of Ac$_4$ManNAc strongly augmented hEPO sialylation by these cells. In fact, when cultured in PSFM containing Ac$_4$ManNAc, SfSWT-19 cells sialylated hEPO at about the same levels as SfSWT-21 cells grown in PSFM without Ac$_4$ManNAc. Again, the addition of Ac$_4$ManNAc did not augment recombinant protein sialylation by SfSWT-21 cells.

Figure 20:
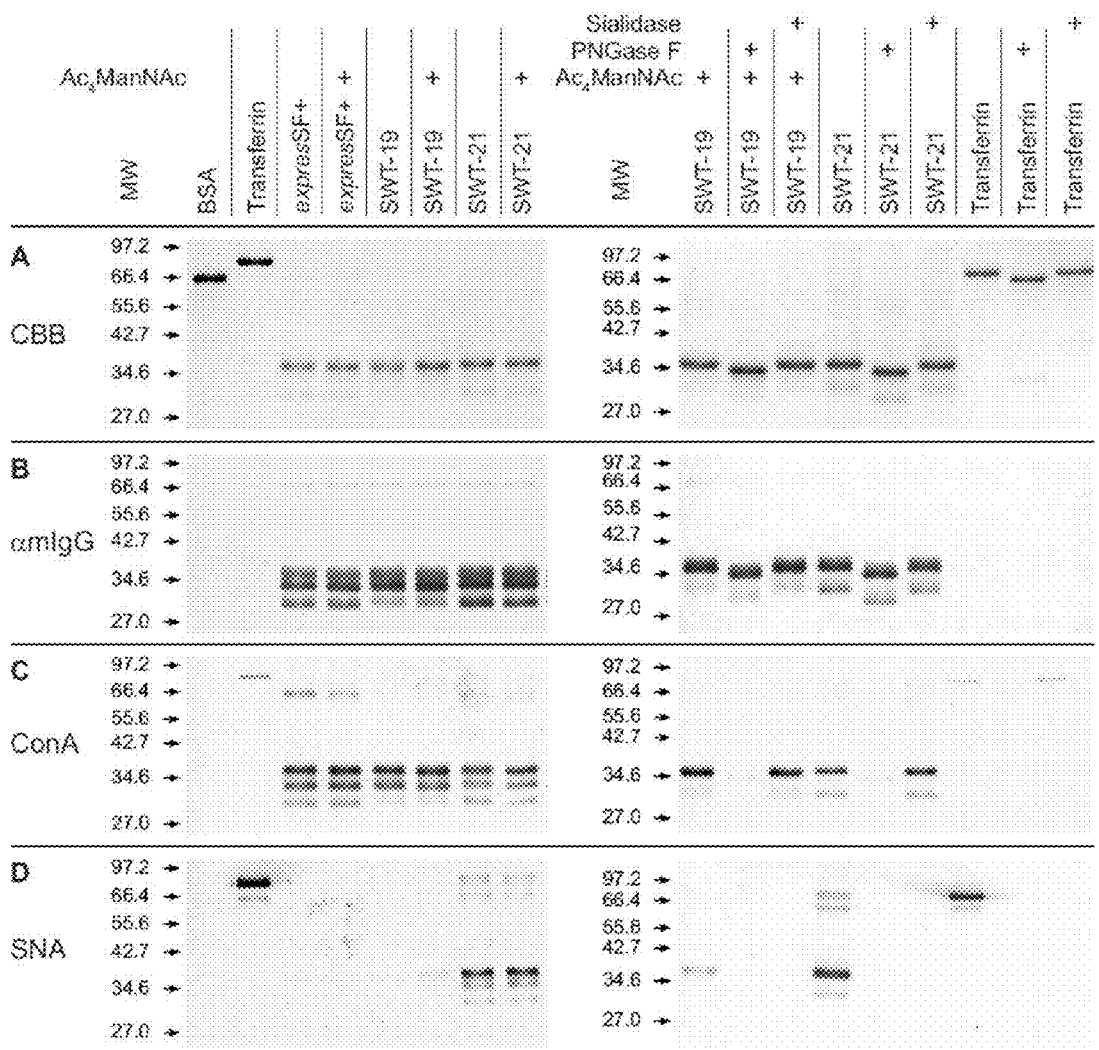
Figure 21:
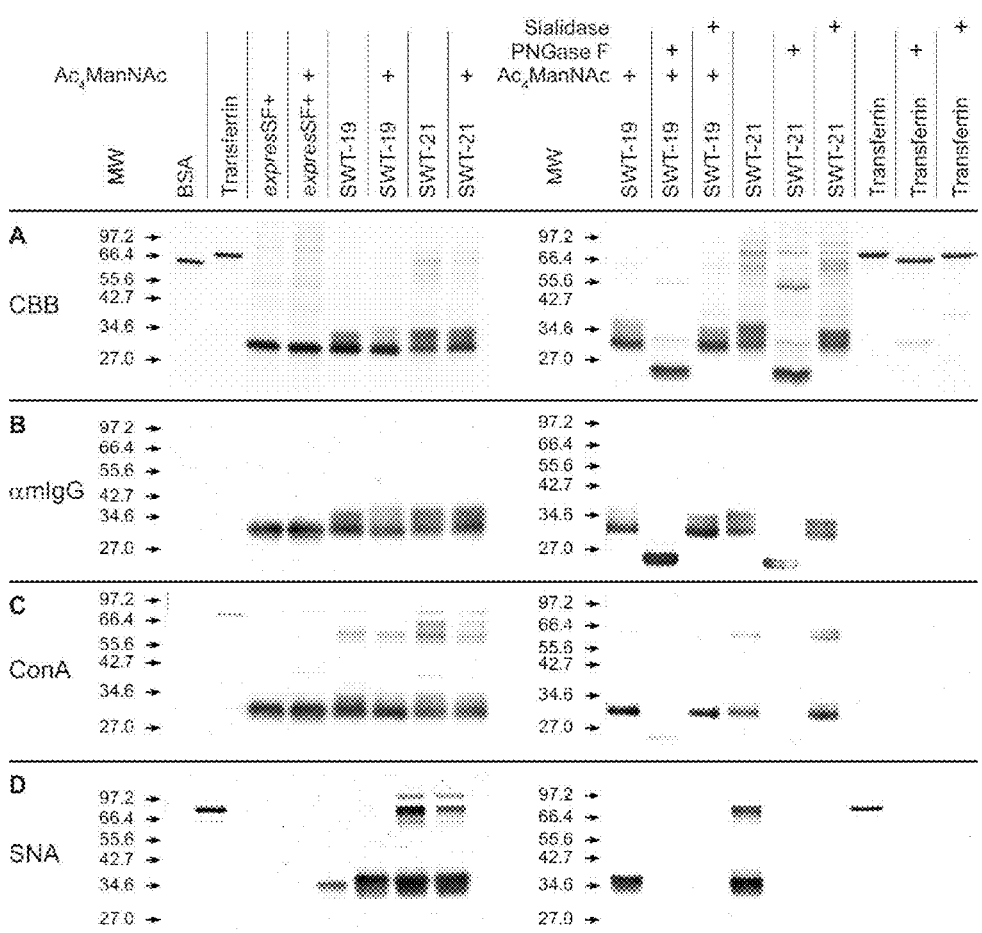

Importantly, the right hand panels of FIGS. 20 and 21 were dedicated to an extensive set of control reactions that clearly document the specificity of the lectin blotting assays. These panels show CBB staining, immunoblotting, and lectin blotting of samples of each protein after pretreatment with PNGase-F, which removes all N-linked glycans, or sialidase, which removes terminal sialic acids, as described in Materials and methods. The absence of ConA and SNA staining after PNGase treatment and the absence of SNA staining after sialidase treatment in each and every case demonstrates that the lectins bound specifically to N-glycans or terminal sialic acids, respectively, under the lectin blotting assay conditions used in this study.

These results directly demonstrated that E. coli GNPE can not only initiate sialic acid biosynthesis, but also can support recombinant glycoprotein sialylation in glycoengineered insect cells cultured in a growth medium lacking ManNAc. In addition, while Ac$_4$ManNAc supplementation augmented recombinant glycoprotein sialylation by glycoengineered insect cells lacking GNPE, it did not augment sialylation by glycoengineered insect cells expressing GNPE. Thus, all of the results obtained in this study showed that E. coli GNPE can be used to drive one step in a sialic acid degradation pathway in reverse, thereby initiating sialic acid biosynthesis and circumventing the requirement for ManNAc supplementation for recombinant glycoprotein sialylation by glycoengineered insect cells.

Discussion

Terminal sialic acids are required for the therapeutic efficacy of many recombinant glycoprotein biologics, such as erythropoietin and some antibodies (Ngantung et al., 2006). This requirement restricts the utility of the baculovirus/insect cell system as a glycoprotein biologics production platform, which does not support recombinant glycoprotein sialylation (reviewed by Geisler and Jarvis, 2009; Harrison and Jarvis, 2006; Jarvis, 2009; Marchal et al., 2001; Shi and Jarvis, 2007). The inability of the baculovirus/insect cell platform to support recombinant glycoprotein sialylation is due to the fact that lepidopteran insect cell lines lack functional levels of late acting glycosyltransferases, as well as the pathways needed for sialic acid biosynthesis and utilization (reviewed by Geisler and Jarvis, 2009; Harrison and Jarvis, 2006; Jarvis, 2009; Marchal et al., 2001; März et al., 1995; Shi and Jarvis, 2007). Previous studies have shown that these deficiencies can be corrected by metabolically engineering baculovirus vectors and/or their lepidopteran insect cell hosts with mammalian genes encoding these functions (reviewed by Geisler and Jarvis, 2009; Harrison and Jarvis, 2006; Jarvis, 2009; Shi and Jarvis, 2007). However, even the most extensively glycoengineered baculovirus/insect cell systems developed to date require media supplementation with the sialic acid precursor, ManNAc. This would increase production costs to non-competitive levels for scaled-up recombinant glycoprotein biologics manufacturing. Thus, it was necessary to further glycoengineer the baculovirus/insect cell system to enable sialic acid biosynthesis from endogenous cellular precursor pools and circumvent the ManNAc supplementation requirement.

Figure 22:
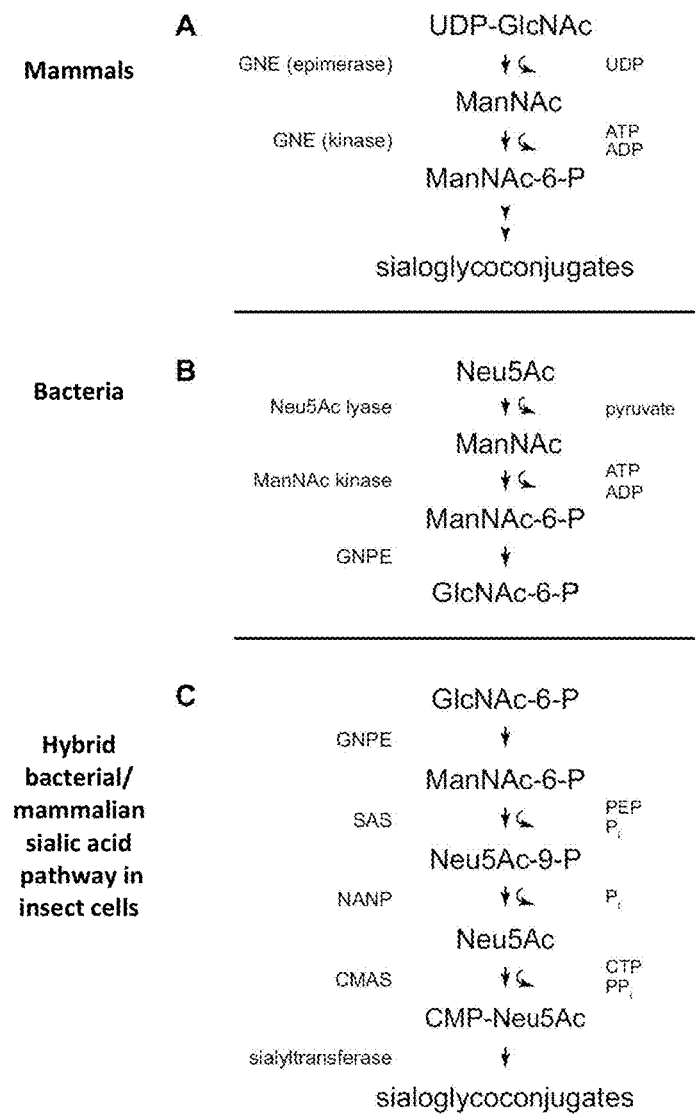

An obvious approach was to engineer insect cells to express GNE, which naturally initiates sialic acid biosynthesis in mammalian cells (Hinderlich et al., 1997; Stäsche et al., 1997; FIG. 22A). However, we believed this would be suboptimal for several reasons, one of which was that GNE overexpression might reduce intracellular UDP-GlcNAc pools and decrease the overall efficiency of N-glycan processing by limiting the activities of one or more N-acetylglucosaminyltransferases (Sasai et al., 2002). With this in mind, we examined other metabolic pathways to identify an enzyme that could be used to initiate sialic acid biosynthesis in insect cells, preferably one that could directly produce ManNAc-6-P, the substrate for SAS. Counterintuitively, this search led us to E. coli GNPE, which normally converts ManNAc-6-P to GlcNAc-6-P as part of a bacterial sialic acid degradation pathway (Plumbridge and Vimr, 1999; Ringenberg et al., 2003; Vimr et al., 2004, FIG. 22B). Realizing that insect cells have endogenous pools of GlcNAc-6-P, but no detectable ManNAc-6-P, we hypothesized that GNPE might be able to use the former metabolite to initiate sialic acid biosynthesis in insect cells. To test this hypothesis, we isolated two closely matched transgenic insect cell lines by transforming expresSF+ cells with a suite of mammalian genes known to support the production of sialic acid, CMP-sialic acid, and sialylated N-glycoproteins. One of these lines, designated SfSWT-21, was additionally transformed with the E. coli GNPE gene, while the other, designated SfSWT-19, was not.

SfSWT-21, but not SfSWT-19 cells were able to produce sialic acid and CMP-sialic acid, as well as sialylated endogenous cell surface glycoconjugates and recombinant mammalian glycoproteins, with no requirement for ManNAc supplementation. ManNAc supplementation did not augment the levels of glycoprotein sialylation and sialic acid and CMP-sialic acid levels in SfSWT-21 cells cultured without supplementation were comparable to those in insect cells infected with a recombinant baculovirus encoding GNE (Viswanathan et al., 2005). Thus, this study clearly demonstrated that GNPE can be used to initiate sialic acid biosynthesis and circumvent the requirement for ManNAc supplementation for recombinant glycoprotein sialylation in glycoengineered insect cells (FIG. 22C).

We emphasize that the utility of this E. coli enzyme for initiating sialic acid production is not limited to the baculovirus/insect cell system. GNPE could be used for this same purpose in many other recombinant glycoprotein production platforms that cannot produce sialic acid, such as yeast, plants, and other insect systems. In previous studies, GNE was used to initiate sialic acid biosynthesis in yeast, plant, and baculovirus/insect cell systems (Castilho et al., 2010; Hamilton et al., 2006; Viswanathan et al., 2003). However, using GNPE presents an alternative, potentially better approach because it would not consume UDP-GlcNAc, as discussed above. GNPE also could be used to enhance sialic acid levels in expression systems that can produce sialic acid, such as the widely used Chinese hamster ovary (CHO)

cell and other mammalian production platforms. Previous efforts to use GNE to increase sialic acid, CMP-sialic acid, and protein sialylation levels in CHO cells failed because GNE is feedback-inhibited by CMP-sialic acid (Bork et al., 2005). This problem was cleverly overcome by using a mutant GNE that is insensitive to feedback inhibition by CMP-sialic acid (Seppala et al., 1999) and CHO cells expressing this enzyme had higher levels of sialic acid, which enhanced recombinant glycoprotein sialylation (Bork et al., 2005; Bork et al., 2007; Son et al., 2011). Engineering CHO cells with E. coli GNPE would also avoid feedback inhibition by CMP-sialic acid and an additional advantage is that this enzyme would not consume UDP-GlcNAc and, therefore, would have no potentially adverse impact on recombinant glycoprotein processing by the N-acetylglucosaminyltransferases.

While sialic acid is clearly critical for the clinical efficacy of recombinant glycoprotein biologics, it also serves as an important precursor for the chemical synthesis of other drugs, such as zanamivir, which is a neuraminidase inhibitor used to treat influenza virus infections. Sialic acid is typically produced in bacteria by enzymes including sialic acid lyase or SAS, each of which use ManNAc as the substrate (reviewed by Tao et al., 2010). Insect or other cell types engineered to constitutively express E. coli GNPE, mammalian SAS, and N-acetylneuraminic acid phosphatase would present an attractive alternative production platform for industrial production of sialic acids.

In summary, we used E. coli GNPE to initiate sialic acid biosynthesis in the absence of an exogenous sialic acid precursor in the baculovirus/insect cell system. This innovative approach can be used to metabolically engineer a variety of systems to enable or enhance recombinant glycoprotein sialylation and it also could be used to create new systems for the production of sialic acid as a precursor for chemical synthesis.

While the preferred embodiments of the invention have been illustrated and described in detail, it will be appreciated by those skilled in the art that that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

REFERENCES

All references, patents, or applications cited herein are incorporated by reference in their entirety, as if written herein.

Patent Documents

1. U.S. Pat. No. 6,949,372, issued 2005 Sep. 27, by Betenbaugh, M J, Lawrence, S, Lee, Y C, Coleman, T A.
2. U.S. Pat. No. 7,776,565, issued 2010 Aug. 17, by Betenbaugh, M J, Lawrence, S, Lee, Y C, Coleman, T A.
3. U.S. Pat. No. 7,781,647, issued 2010 Aug. 24, by Bakker, H A C, and Ondersoek, S D L.
4. U.S. Pat. No. 7,863,020, issued 2011 Jan. 4, by Hamilton, S R.
5. U.S. Pat. Application Publication, 2007/0067855, published 2007 Mar. 22, by Jarvis, D L, Van Beek, N, Fraser, M.
6. U.S. Pat. Application Publication, 2008/0145899, published 2008 Jun. 19, by Johnson, K, Byrn, N J, DeFrees, S.
7. U.S. Pat. Application Publication, 2010/0186099, published 2010 Jul. 22, by Fraser, M J and Jarvis, D L.
8. U.S. Pat. Application Publication, 2011/0014661, published 2011 Jan. 20, by Samain.

Journal Articles

1. Aumiller, J. J., Mabashi-Asazuma, H., Hillar, A., Shi, X., Jarvis, D. L., 2012. A new glycoengineered insect cell line with an inducibly mammalianized protein N-glycosylation pathway. Glycobiology. 22, 417-428.
2. Aumiller, J. J., Hollister, J. R., and Jarvis, D. L. (2003) A transgenic lepidopteran insect cell line engineered to produce CMP-sialic acid and sialoglycoproteins. Glycobiology, 13: 497-507.
3. Blattner F R, Plunkett G III, Bloch C A, Perna N T, Burland V, Riley M, Collado-Vides J, Glasner J D, Rode C K, Mayhew G F, Gregor J, Davis N W, Kirkpatrick H A, Goeden M A, Rose D J, Mau B, Shao Y (1997). The complete genome sequence of Escherichia coli K-12. Science, 277: 1453-1474.
4. Bork, K., Reutter, W., Gerardy-Schahn, R., Horstkorte, R., 2005. The intracellular concentration of sialic acid regulates the polysialylation of the neural cell adhesion molecule. FEBS Lett. 579, 5079-5083.
5. Bork, K., Reutter, W., Weidemann, W., Horstkorte, R., 2007. Enhanced sialylation of EPO by overexpression of UDP-GlcNAc 2-epimerase/ManAc kinase containing a sialuria mutation in CHO cells. FEBS Lett. 581, 4195-4198.
6. Castilho, A., Strasser, R., Stadlmann, J., Grass, J., Jez, J. Gattinger, P., Kunert, R., Quendler, H., Pabst, M., Leonard, R, Altmann, F. and H. Steinkellner (2010) In planta protein sialylation through overexpression of the respective mammalian pathway. J Biol Chem, 285: 15923-15930.
7. Chang, K. H., J. M. Yang, et al. (2005) Enhanced activity of recombinant beta-secretase from Drosophila melanogaster S2 cells transformed with cDNAs encoding human beta1,4-galactosyltransferase and Gal beta1,4-GlcNAc alpha2,6-sialyltransferase. J Biotechnol, 116(4): 359-367.
8. Chung, C. H., Mirakhur, B., Chan, E., Le, Q.-T., Berlin, J., Morse, M., Murphy, B. A., Satinover, S. M., Hosen, J., Mauro, D., Slebos, R. J., Zhou, Q., Gold, D., Hatley, T., Hicklin, D. J., Platts-Mills, T. A. E., 2008. Cetuximab-induced anaphylaxis and IgE specific for galactose-α-1, 3-galactose. New England Journal of Medicine, 358, 1109-1117.
9. Fierfort and Samain, (2008) Genetic Engineering of Escherichia coli for the economical production of sialylated oligosaccharides. J Biotechnol, 134:261-265.
10. Geisler, C., Jarvis, D. L., 2009. Insect cell glycosylation patterns in the context of biopharmaceuticals. In: Walsh, G. (Ed.), Post-translational modifications in the context of biopharmaceuticals. Wiley-VCH, Weinheim, pp. 165-191.
11. Geisler, C., Jarvis, D. L., 2011. Letter to the Glyco-Forum: Effective glycoanalysis with Maackia amurensis lectins requires a clear understanding of their binding specificities. Glycobiology. 21, 988-993.
12. Ghaderi, D., Taylor, R. E., Padler-Karavani, V., Diaz, S., Varki, A., 2010. Implications of the presence of N-glycolylneuraminic acid in recombinant therapeutic glycoproteins. Nat Biotech, 28, 863-867.
13. Ghosh, S. and S. Roseman (1965) The Sialic Acids IV. N-acyl-D-glucosamine 6-phosphate 2-epimerase. J Biol Chem, 240(4): 1525-1530.

14. Gritz and Davis (1983) Plasmid-encoded hygromycin B resistance: the sequence of hygromycin B phosphotransferase gene and its expression in *Escherichia coli* and *Saccharomyces cerevisiae. Gene,* 25(2-3):179-188.
15. Hamilton, S. R., Davidson, R. C., Sethuraman, N., Nett, J. H., Jiang, Y., Rios, S., Bobrowicz, P., Stadheim, T. A., Li, H., Choi, B. K., Hopkins, D., Wischnewski, H., Roser, J., Mitchell, T., Strawbridge, R. R., Hoopes, J., Wildt, S., Gerngross, T. U., (2006) Humanization of yeast to produce complex terminally sialylated glycoproteins. *Science,* 313(5792): 1441-1443.
16. Harrison, R. L., Jarvis, D. L., 2006. Protein N-glycosylation in the baculovirus-insect cell expression system and engineering of insect cells to produce "mammalianized" recombinant glycoproteins. *Adv Virus Res,* 68, 159-191.
17. Harrison, R. L., Jarvis, D. L., 2007a. Transforming lepidopteran insect cells for continuous recombinant protein expression. *Methods in Molecular Biology,* 388, 299-316.
18. Harrison, R. L., Jarvis, D. L., 2007b. Transforming lepidopteran insect cells for improved protein processing. *Methods Mol Biol,* 388, 341-356.
19. Hill, D. R., Aumiller, J. J., Shi, X., Jarvis, D. L., (2006) Isolation and analysis of a baculovirus vector that supports recombinant glycoprotein sialylation by SfSWT-1 cells cultured in serum-free medium. *Biotechnol Bioeng,* 95(1): 37-47.
20. Hinderlich, S., M. Berger, et al. (2001) Biosynthesis of N-acetylneuraminic acid in cells lacking UDP-N-acetylglucosamine 2-epimerase/N-acetylmannosamine kinase. *Biol Chem,* 382(2): 291-297.
21. Hinderlich, S., Stäsche, R., Zeitler, R., Reutter, W., 1997. A bifunctional enzyme catalyzes the first two steps in N-acetylneuraminic acid biosynthesis of rat liver—Purification and characterization of UDP-N-acetylglucosamine 2-epimerase/N-acetylmannosamine kinase. *Journal of Biological Chemistry,* 272, 24313-24318.
22. Hollister, J. and D. L. Jarvis (2001) Engineering lepidopteran insect cells for sialoglycoprotein production by genetic transformation with mammalian beta 1,4-galactosyltransferase and alpha 2,6-sialyltransferase genes. *Glycobiology,* 11: 1-9.
23. Hollister, J. R., Grabenhorst, E., Nimtz, M., Conradt, H., Jarvis, D. L., (2002) Engineering the protein N-glycosylation pathway in insect cells for production of biantennary, complex N-glycans. *Biochemistry,* 41: 15093-15104.
24. Hollister, J. R., Shaper, J. H., and Jarvis, D. L. (1998) Stable expression of mammalian β1,4 galactosyltransferase extends the N-glycosylation pathway in insect cells. *Glycobiology,* 8:473-480.
25. Hooker, A. D., Green, N. H., Baines, A. J., Bull, A. T., Jenkins, N., Strange, P. G., James, D. C., 1999. Constraints on the transport and glycosylation of recombinant IFN-gamma in Chinese hamster ovary and insect cells. *Biotechnol Bioeng,* 63, 559-572.
26. Ishida, N, Ito, M, Yoshioka, S, Sun-Wada, G-H and Kawakita, M (1998) Functional expression of human Golgi CMP-sialic acid transporter in the Golgi complex of a transporter-deficient Chinese hamster ovary cell mutant. *J Biochem,* 124(1): 171-178.
27. Jarvis, D. L., 2009. Baculovirus—insect cell expression systems. In: Richard, R. B., Murray, P. D. (Eds.), Methods in Enzymology, vol. 463. Academic Press, pp. 191-222.
28. Jarvis, D. L., C. Weinkauf, et al. (1996) Immediate-early baculovirus vectors for foreign gene expression in transformed or infected insect cells. *Protein Expr Purif,* 8(2): 191-203.
29. Jarvis, D. L., Finn, E. E., 1996. Modifying the insect cell N-glycosylation pathway with immediate early baculovirus expression vectors. *Nature Biotechnology,* 14, 1288-1292.
30. Jarvis, D. L., Fleming, J. A., Kovacs, G. R., Summers, M. D., Guarino, L. A., 1990. Use of early baculovirus promoters for continuous expression and efficient processing of foreign gene products in stably transformed lepidopteran cells. *Nature Biotechnology,* 8, 950-955.
31. Jarvis, D. L., Howe, D., Aumiller, J. J., 2001. Novel baculovirus expression vectors that provide sialylation of recombinant glycoproteins in lepidopteran insect cells. *Journal of Virology,* 75, 6223-6227.
32. Jin Q, Yuan Z, Xu J, Wang Y, Shen Y, Lu W, Wang J, Liu H, Yang J, Yang F, Zhang X, Zhang J, Yang G, Wu H, Qu D, Dong J, Sun L, Xue Y, Zhao A, Gao Y, Zhu J, Kan B, Ding K, Chen S, Cheng H, Yao Z, He B, Chen R, Ma D, Qiang B, Wen Y, Hou Y, Yu J (2002) Genome sequence of *Shigella flexneri* 2a: insights into pathogenicity through comparison with genomes of *Escherichia coli* K12 and O157. *Nucleic Acids Res,* 30: 4432-4441.
33. Jones, M. B., Teng, H., Rhee, J. K., Lahar, N., Baskaran, G., Yarema, K. J., 2004. Characterization of the cellular uptake and metabolic conversion of acetylated Nacetylmannosamine (ManNAc) analogues to sialic acids. *Biotechnology and Bioengineering,* 85, 394-405.
34. Lawrence, S. M., K. A. Huddleston, et al. (2000) Cloning and expression of the human N-acetylneuraminic acid phosphate synthase gene with 2-keto-3-deoxy-D-glycero-D-galacto-nononic acid biosynthetic ability. *J Biol Chem,* 275(23): 17869-77.
35. Leary, J. J., Brigati, D. J., Ward, D. C., 1983. Rapid and sensitive colorimetric method for visualizing biotin-labeled DNA probes hybridized to DNA or RNA immobilized on nitrocellulose: Bio-blots. *Proc Natl Acad Sci USA,* 80, 4045-4049.
36. Marchal, I., Jarvis, D. L., Cacan, R., Verbert, A., 2001. Glycoproteins from insect cells: sialylated or not? *Biol. Chem,* 382, 151-159.
37. März, L., Altmann, F., Staudacher, E., Kubelka, V., 1995. Protein glycosylation in insects. In: Montreuil, J., Vliegenthart, J. F. G., Schachter, H. (Eds.), Glycoproteins, vol. 29a. Elsevier, Amsterdam, pp. 543-563.
38. Morell, A. G., G. Gregoriadis, et al. (1971) The role of sialic acid in determining the survival of glycoproteins in the circulation. *J Biol Chem,* 246(5): 1461-1467.
39. Münster, A. K., M. Eckhardt, et al. (1998) Mammalian cytidine 5'-monophosphate N-acetylneuraminic acid synthetase: a nuclear protein with evolutionarily conserved structural motifs. *Proc Natl Acad Sci USA,* 95(16): 9140-9145.
40. Nakata, D., B. E. Close, et al. (2000) Molecular cloning and expression of the mouse N-acetylneuraminic acid 9-phosphate synthase which does not have deaminoneuraminic acid (KDN) 9-phosphate synthase activity. *Biochem Biophys Res Commun,* 273(2): 642-648.
41. Ngantung, F. A., Miller, P. G., Brushett, F. R., Tang, G. L., Wang, D. I., (2006) RNA interference of sialidase improves glycoprotein sialic acid content consistency. *Biotechnol Bioeng,* 95(1): 106-19.
42. O'Reilly, D. R., Miller, L. K., and Luckow, V. A. (1992) Baculovirus expression vectors. W.H. Freeman and Company, New York.

43. Perna N T, Plunkett G III, Burland V, Mau B, Glasner J D, Rose D J, Mayhew G F, Evans P S, Gregor J, Kirkpatrick H A, Posfai G, Hackett J, Klink S, Boutin A, Shao Y, Miller L, Grotbeck E J, Davis N W, Lim A, Dimalanta E T, Potamousis K D, Apodaca J, Ananthara- man T S, Lin J, Yen G, Schwartz D C, Welch R A, Blattner F R (2001) Genome sequence of enterohaemorrhagic *Escherichia coli* O157:H7. *Nature*, 409: 529-533.

44. Plumbridge, J. and E. Vimr (1999) Convergent pathways for utilization of the amino sugars N-acetylglucosamine, N-acetylmannosamine, and N-acetylneuraminic acid by *Escherichia coli*. *J Bacteriol*, 181(1): 47-54.

45. Riley M, Abe T, Arnaud M B, Berlyn M K, Blattner F R, Chaudhuri R R, Glasner J D, Horiuchi T, Keseler I M, Kosuge T, Mori H, Perna N T, Plunkett G, Rudd K E, Serres M H, Thomas G H, Thomson N R, Wishart D, Wanner B L (2006) *Escherichia coli* K-12: a cooperatively developed annotation snapshot-2005. *Nucleic Acids Res*, 34: 1-9.

46. Ringenberg, M. A., Steenbergen, S. M., Vimr, E. R., (2003) The first committed step in the biosynthesis of sialic acid by *Escherichia coli* K1 does not involve a phosphorylated N-acetylmannosamine intermediate. *Mol Microbiol*, 50(3): 961-75.

47. Russo, R N, Shaper, N L, and Shaper, J H (1990) Bovine beta 1→4-galactosyltransferase: two sets of mRNA transcripts encode two forms of the protein with different amino-terminal domains. In vitro translation experiments demonstrate that both the short and the long forms of the enzyme are type II membrane-bound glycoproteins. *J Biol Chem*, 265: 3324-3331.

48. Sambrook, J., Fritsch, E. F., Maniatis, T., 1989. Molecular cloning: a laboratory manual (2nd edition). Cold Spring Harbor Laboratory Press, Cold Spring Harbor, N.Y.

49. Sasai, K., Ikeda, Y., Fujii, T., Tsuda, T., Taniguchi, N., (2002) UDP-GlcNAc concentration is an important factor in the biosynthesis of beta1,6-branched oligosaccharides: regulation based on the kinetic properties of N-acetylglucosaminyltransferase V. *Glycobiology*, 12(2): 119-127.

50. Sasaki, K., E. Watanabe, et al. (1993). Expression cloning of a novel Gal β(1-3/1-4) GlcNAc α2,3-sialyltransferase using lectin resistance selection. *J Biol Chem*, 268(30): 22782-22787.

51. Schachter, H. (2000) The joys of HexNAc. The synthesis and function of N- and O-glycan branches. *Glycoconj J*, 17(7-9): 465-83.

52. Seo, N. S., Hollister, J. R., Jarvis, D. L., 2001. Mammalian glycosyltransferase expression allows sialoglycoprotein production by baculovirus-infected insect cells. *Protein Expression and Purification*, 22, 234-241.

53. Seppala, R., Lehto, V.-P., Gahl, W. A., 1999. Mutations in the human UDP-Nacetylglucosamine 2-epimerase gene define the disease sialuria and the allosteric site of the enzyme. *The American Journal of Human Genetics*, 64, 1563-1569.

54. Shaper, N. L., J. H. Shaper, et al. (1986) Bovine galactosyltransferase: identification of a clone by direct immunological screening of a cDNA expression library. *Proc Natl Acad Sci USA*, 83(6): 1573-1577.

55. Shi, X., Jarvis, D. L., 2007. Protein N-glycosylation in the baculovirus-insect cell system. Curr Drug Targets. 8, 1116-1125. Son, Y. D., Jeong, Y. T., Park, S. Y., Kim, J. H., 2011. Enhanced sialylation of recombinant human erythropoietin in Chinese hamster ovary cells by combinatorial engineering of selected genes. *Glycobiology*, 21, 1019-1028.

56. Son, Y-D, Jeong, Y T Park, S-Y and Kim, J H, 2011. Enhanced sialylation of recombinant human erythropoietin in Chinese hamster ovary cells by combinatorial engineering of selected genes. *Glycobiology*, 21(8) 1019-1028

57. Stäsche, R., Hinderlich, S., Weise, C., Effertz, K., Lucka, L., Moormann, P., Reutter, W., 1997. A bifunctional enzyme catalyzes the first two steps in N-acetylneuraminic acid biosynthesis of rat liver. Molecular cloning and functional expression of UDP-N-acetyl-glucosamine 2-epimerase/N-acetylmannosamine kinase. *J Biol Chem*, 272, 24319-24324.

58. Summers, M. D., Smith, G. E., A manual of methods for baculovirus vectors and insect cell culture procedures. *Texas Agricultural Experiment Station Bulletin B-1555*. Texas Agricultural Experiment Station, College Station, Tex., 1987.

59. Tan, J., A. F. D'Agostaro, et al. (1995) The human UDP-N-acetylglucosamine: α-6-D-mannoside-β-1,2-N-acetylglucosaminyltransferase II gene (MGAT2). Cloning of genomic DNA, localization to chromosome 14q21, expression in insect cells and purification of the recombinant protein. *Eur J Biochem*, 231(2): 317-328.

60. Tao, F., Zhang, Y., Ma, C., Xu, P., 2010. Biotechnological production and applications of N-acetyl-D-neuraminic acid: current state and perspectives. *Appl. Microbiol. Biotechnol*, 87, 1281-1289.

61. Thomason L C, Court D L, Datta A R, Khanna R, Rosner J L (2004) Identification of *Escherichia coli* K12 ybhE gene as pgl, encoding 6-phosphogluconolactonase. *J Bacteriol*, 186: 8248-8253.

62. Tomiya, N., Ailor, E., Lawrence, S. M., Betenbaugh, M. J., Lee, Y. C., 2001. Determination of nucleotides and sugar nucleotides involved in protein glycosylation by high-performance anion-exchange chromatography: sugar nucleotide contents in cultured insect cells and mammalian cells. *Analytical Biochemistry*, 293, 129-137.

63. Toth, A. M., Geisler, C., Aumiller, J. J., Jarvis, D. L., 2011. Factors affecting recombinant Western equine encephalitis virus glycoprotein production in the baculovirus system. *Protein Expr. Purif*, 80, 274-282.

64. Vaughn, J. L., Goodwin, R. H., Tompkins, G. J., McCawley, P., (1977) The establishment of two cell lines from the insect *Spodoptera frugiperda* (Lepidoptera; Noctuidae). *In Vitro*, 13(4): 213-217.

65. Vimr, E. R., Kalivoda, K. A., Deszo, E. L., Steenbergen, S. M., 2004. Diversity of microbial sialic acid metabolism. *Microbiol Mol Biol Rev*, 68, 132-153.

66. Viswanathan, K., Narang, S., Hinderlich, S., Lee, Y. C., Betenbaugh, M. J., 2005. Engineering intracellular CMP-sialic acid metabolism into insect cells and methods to enhance its generation. *Biochemistry*, 44, 7526-7534.

67. Viswanathan, K., Lawrence, S., Hinderlich, S., Yarema, K. J., Lee, Y. C., Betenbaugh, M. J., (2003) Engineering sialic acid synthetic ability into insect cells: identifying metabolic bottlenecks and devising strategies to overcome them. *Biochemistry*, 42(51): 15215-15225.

68. Walsh, G., 2010. Biopharmaceutical benchmarks 2010. *Nat Biotech*, 28, 917-924.

69. Walters, D M, Stirewalt, V L, Melville, S B (1999) Cloning, sequence, and transcriptional regulation of the operon encoding a putative N-acetylmannosamine-6-phosphate epimerase (nanE) and sialic acid lyase (nanA) in *Clostridium perfringens*. *J Bacteriol*, 181: 4526-4532.

70. Warren, L., 1959. The thiobarbituric acid assay of sialic acids. *J. Biol. Chem*, 234, 1971-1975.

71. Weinstein et al., (1987) Primary structure of beta-galactoside alpha 2,6-sialyltransferase. Conversion of membrane-bound enzyme to soluble forms by cleavage of the NH2-terminal signal anchor. *J Biol Chem,* 262(36): 17735-17743.

72. Wen, D. X., E. C. Svensson, et al. (1992) Tissue-specific alternative splicing of the β-galactoside α2,6-sialyltransferase gene. *J Biol Chem,* 267(4): 2512-2518.

73. Wickham, T. J., Davis, T., Granados, R. R., Shuler, M. L., Wood, H. A., 1992. Screening of insect cell lines for the production of recombinant proteins and infectious virus in the baculovirus expression system. *Biotechnol Prog,* 8, 391-396.

74. Yang F, Yang J, Zhang X, Chen L, Jiang Y, Yan Y, Tang X, Wang J, Xiong Z, Dong J, Xue Y, Zhu Y, Xu X, Sun L, Chen S, Nie H, Peng J, Xu J, Wang Y, Yuan Z, Wen Y, Yao Z, Shen Y, Qiang B, Hou Y, Yu J, Jin Q (2005) Genome dynamics and diversity of *Shigella* species, the etiologic agents of bacillary dysentery. *Nucleic Acids Res,* 33: 6445-6458.

75. Seal R L, Gordon S M, Lush M J, Wright M W, Bruford E A. (2011 January) genenames.org: the HGNC resources in 2011. Nucleic Acids Res. 39(Database issue):D519-9. PMID: 20929869 PMCID: PMC3013772 (Nucleic Acids Research Advance Access published Oct. 6, 2010, Nucleic Acids Research, 2010, 1-6 doi:10.1093/nar/gkq892).

What is claimed is:

1. An isolated transgenic insect cell which is modified to comprise at least one nucleic acid stably integrated into the genome of said cell, encoding a polypeptide, GlcNAc-6-P 2'-epimerase (GNPE), which is capable of converting intracellular N-acetyl-D-glucosamine-6-phosphate (GlcNAc-6-P) to intracellular N-acetyl-D-mannosamine-6-phosphate (ManNAc-6-P) in an intact cell,
   wherein each nucleic acid encoding said polypeptide is operably-linked to a promoter functional in said cell, and
   wherein said nucleic acid is derived from a source belonging to the domain Bacteria;
   wherein said polypeptide is selected from the group consisting of:
   (a) a polypeptide comprising SEQ ID NO: 6;
   (b) a variant of the polypeptide specified in (b) that contains one or more conservative amino acid substitutions in which GNPE function is retained;
   (c) a truncated or fusion variant of the polypeptide specified in (a) or (b) comprising one or more insertions or deletions of amino acids in which GNPE function is retained;
   wherein each of said one or more insertions or deletions are located between regions that are conserved among
   (1) the polypeptides specified in (a) or (b); and
   (2) a polypeptide capable of converting GlcNAc-6-P to ManNAc-6-P which is obtained from a source belonging to the domain Bacteria;
   (d) a truncated or fusion variant of the polypeptide specified in (a), (b), or (c) comprising one or more insertions or deletions of amino acids in which GNPE function is retained;
   wherein each of said one or more insertions or deletions are located at
   the amino terminus, the carboxy terminus, or both the amino and carboxy termini of
   the polypeptide specified in (a), (b), or (c);
   wherein said polypeptide capable of converting GlcNAc-6-P to ManNAc-6-P is expressed, and GNPE activity is above endogenous levels of activity in a parent cell lacking said nucleic acid.

2. The transgenic insect cell of claim 1, wherein the polypeptide capable of converting GlcNAc-6-P to ManNAc-6-P is
(a) said polypeptide comprising SEQ ID NO: 6.

3. The transgenic insect cell of claim 1, wherein said polypeptide is stably expressed in said cell.

4. A transgenic Lepidopteran insect larva whose genome comprises at least one nucleic acid encoding a polypeptide, GlcNAc-6-P 2'-epimerase (GNPE), which is capable of converting intracellular N acetyl-D-glucosamine-6-phosphate (GlcNAc-6-P) to intracellular N-acetyl-D-mannosamine-6-phosphate (ManNAc-6-P)
wherein each nucleic acid encoding said polypeptide is operably-linked to a promoter functional in said cell, and
wherein said nucleic acid is derived from a source belonging to the domain Bacteria;
wherein said polypeptide is selected from the group consisting of:
(a) a polypeptide comprising SEQ ID NO: 6;
(b) a variant of the polypeptide specified in (b) that contains one or more conservative amino acid substitutions in which GNPE function is retained;
(c) a truncated or fusion variant of the polypeptide specified in (a) or (b) comprising one or more insertions or deletions of amino acids in which GNPE function is retained;
wherein each of said one or more insertions or deletions are located between regions that are conserved among
(1) the polypeptides specified in (a) or (b); and
(2) a polypeptide capable of converting GlcNAc-6-P to ManNAc-6-P which is obtained from a source belonging to the domain Bacteria;
(d) a truncated or fusion variant of the polypeptide specified in (a), (b), or (c) comprising one or more insertions or deletions of amino acids in which GNPE function is retained;
wherein each of said one or more insertions or deletions are located at
the amino terminus, the carboxy terminus, or both the amino and carboxy termini of
the polypeptide specified in (a), (b), or (c);
wherein said polypeptide capable of converting GlcNAc-6-P to ManNAc-6-P is expressed, and GNPE activity is above endogenous levels of activity in a parent cell lacking said nucleic acid;
wherein said transgenic Lepidopteran insect larva is in a genus selected from the group consisting of *Lymantria, Helicoverpa, Heliothis, Mamestra, Malocosoma, Leucania, Trichoplusia, Anticarsia, Spodoptera, Manduca, Choristoneura, Bombyx*, and *Estigmene*.

5. The transgenic insect cell of claim 1, wherein said cell is a somatic cell.

6. The transgenic insect cell of claim 1, wherein said cell is a germ cell.

7. A method of producing a transgenic Lepidopteran insect larva of claim 4, comprising
(a) introducing at least one nucleic acid encoding a functional GNPE polypeptide into a larval cell, wherein each nucleic acid is operably-linked to a promoter functional in said cell, and
(b) growing the larva under conditions wherein said polypeptide is expressed, and GNPE activity is above the endogenous level of GNPE activity in a larval cell lacking said nucleic acid.

8. The method of claim 7, wherein at least one nucleic acid encoding a functional GNPE polypeptide introduced into said larval cell is on an expression vector comprising said nucleic acid.

9. The method of claim 8 wherein said expression vector is a plasmid.

10. The method of claim 8, wherein said expression vector is a virus.

11. The method of claim 8, wherein said expression vector comprises a transposon.

12. The method of claim 11, wherein said transposon is a piggyBac transposon.

13. A fertile, adult form of a transgenic Lepidopteran insect, derived from the transgenic Lepidopteran insect larva of claim 4.

14. A transgenic insect Lepidopteran cell egg, produced by the fertile, adult form of a transgenic Lepidopteran insect of claim 13.

15. The transgenic insect cell of claim 1,
further comprising at least one of the following nucleic acids:
(i) at least one nucleic acid encoding a polypeptide capable of converting ManNAc-6-P to N-acetylneuraminate-9-P;
(ii) at least one nucleic acid encoding a polypeptide capable of converting N-acetyl-neuraminate-9-P to N-acetylneuraminate;
(iii) at least one nucleic acid encoding a polypeptide capable of converting N-acetylneuraminate to CM P-N-acetylneuraminate;
(iv) at least one nucleic acid encoding a polypeptide designated Golgi cytidine 5'-monophosphate sialic acid transporter (CSAT), which is capable of transporting CMP-N-acetylneuraminate (CMP-Neu5Ac) from the cytoplasm to the Golgi;
(v) at least one nucleic acid encoding a polypeptide designated as a glycosyltransferase (GT), classified in enzyme class EC 2.4; or
(vi) at least one nucleic acid encoding a polypeptide designated as a glycosylhydrolase (GH), classified in enzyme class EC 3.2.1;
wherein each nucleic acid encoding a polypeptide is operably-linked to a promoter which is functional in said cell.

16. The transgenic insect cell of claim 15, wherein the polypeptide capable of converting GlcNAc-6-P to ManNAc-6-P is
(a) said polypeptide comprising SEQ ID NO: 6.

17. The transgenic insect cell of claim 15, wherein said polypeptide capable of converting GlcNAc-6-P to ManNAc-6-P is stably expressed in said cell.

18. The transgenic Lepidopteran insect larva of claim 4, whose genome further comprises at least one of the following nucleic acids:
(i) at least one nucleic acid encoding a polypeptide capable of converting ManNAc-6-P to N-acetylneuraminate-9-P;
(ii) at least one nucleic acid encoding a polypeptide capable of converting N-acetyl-neuraminate-9-P to N-acetylneuraminate;
(iii) at least one nucleic acid encoding a polypeptide capable of converting N-acetylneuraminate to CMP-N-acetylneuraminate;
(iv) at least one nucleic acid encoding a polypeptide designated Golgi cytidine 5'-monophosphate sialic acid transporter (CSAT), which is capable of transporting CMP-N-acetylneuraminate (CMP-Neu5Ac) from the cytoplasm to the Golgi;
- (v) at least one nucleic acid encoding a polypeptide designated as a glycosyltransferase (GT), classified in enzyme class EC 2.4; or
- (vi) at least one nucleic acid encoding a polypeptide designated as a glycosylhydrolase (GH), classified in enzyme class EC 3.2.1;
  wherein each nucleic acid encoding a polypeptide is operably-linked to a promoter which is functional in said cell.

19. A fertile, adult form of a transgenic Lepidopteran insect, derived from the transgenic Lepidopteran insect larva of claim 18.

20. A transgenic Lepidopteran insect cell egg, produced by the fertile, adult form of a transgenic Lepidopteran insect of claim 19.

21. A method of producing the transgenic Lepidopteran insect larva of claim 18, comprising
    (a) introducing at least one nucleic acid encoding a functional GNPE into a larval cell, wherein said cell comprises at least one of the following nucleic acids:
    - (i) at least one nucleic acid encoding a polypeptide capable of converting ManNAc-6-P to N-acetylneuraminate-9-P;
    - (ii) at least one nucleic encoding a polypeptide capable of converting N-acetyl-neuraminate-9-P to N-acetylneuraminate;
    - (iii) at least one nucleic acid encoding a polypeptide capable of converting N-acetylneuraminate to CMP-N-acetylneuraminate;
    - (iv) at least one nucleic acid encoding a polypeptide designated Golgi cytidine 5'-monophosphate sialic acid transporter (CSAT), which is capable of transporting CMP-N-acetylneuraminate (CMP-Neu5Ac) from the cytoplasm to the Golgi;
    - (v) at least one nucleic acid encoding a polypeptide designated as a glycosyltransferase (GT), classified in enzyme class EC 2.4; or
    - (vi) at least one nucleic acid encoding a polypeptide designated as a glycosylhydrolase (GH), classified in enzyme class EC 3.2.1;
    wherein each nucleic acid encoding a polypeptide is operably-linked to a promoter which is functional in said cell, and
    (b) growing the larva under conditions wherein said polypeptide capable of converting GlcNAc-6-P to ManNAc-6-P is expressed, and GNPE activity is above endogenous levels of activity in a larval cell lacking said nucleic acid.

22. A method of producing the transgenic Lepidopteran insect larva of claim 18, comprising
    (a) introducing into a larval cell comprising at least one nucleic acid encoding a functional GNPE, at least one of the following nucleic acids:
    - (i) at least one nucleic acid encoding a polypeptide capable of converting ManNAc-6-P to N-acetylneuraminate-9-P;
    - (ii) at least one nucleic acid encoding a polypeptide capable of converting N-acetyl-neuraminate-9-P to N-acetylneuraminate;
    - (iii) at least one nucleic acid encoding a polypeptide capable of converting N-acetylneuraminate to CMP-N-acetylneuraminate;
    - (iv) at least one nucleic acid encoding a polypeptide designated Golgi cytidine 5'-monophosphate sialic acid transporter (CSAT), which is capable of transporting CMP-N-acetylneuraminate (CMP-Neu5Ac) from the cytoplasm to the Golgi;
    - (v) at least one nucleic acid encoding a polypeptide designated as a glycosyltransferase (GT), classified in enzyme class EC 2.4; or
    - (vi) at least one nucleic acid encoding a polypeptide designated as a glycosylhydrolase (GH), classified in enzyme class EC 3.2.1;
    wherein each nucleic acid encoding a polypeptide is operably-linked to a promoter which is functional in said cell, and
    (b) growing the larva under conditions wherein said polypeptide capable of converting GlcNAc-6-P to ManNAc-6-P is expressed, and GNPE activity is above endogenous levels of activity in a larval cell lacking said nucleic acid.

23. A method of producing the transgenic Lepidopteran insect larva of claim 18, comprising
    (a) simultaneously introducing into a larval cell at least one nucleic acid encoding a functional GNPE, and at least one of the following nucleic acids:
    - (i) at least one nucleic acid encoding a polypeptide capable of converting ManNAc-6-P to N-acetylneuraminate-9-P;
    - (ii) at least one nucleic acid encoding a polypeptide capable of converting N-acetyl-neuraminate-9-P to N-acetylneuraminate;
    - (iii) at least one nucleic acid encoding a polypeptide capable of converting N-acetylneuraminate to CMP-N-acetylneuraminate;
    - (iv) at least one nucleic acid encoding a polypeptide designated Golgi cytidine 5'-monophosphate sialic acid transporter (CSAT), which is capable of transporting CMP-N-acetylneuraminate (CMP-Neu5Ac) from the cytoplasm to the Golgi;
    - (v) at least one nucleic acid encoding a polypeptide designated as a glycosyltransferase (GT), classified in enzyme class EC 2.4; or
    - (vi) at least one nucleic acid encoding a polypeptide designated as a glycosylhydrolase (GH), classified in enzyme class EC 3.2.1;
    wherein each nucleic acid encoding a polypeptide is operably-linked to a promoter which is functional in said cell, and
    (b) growing the larva under conditions wherein said polypeptide capable of converting GlcNAc-6-P to ManNAc-6-P is expressed, and GNPE activity is above endogenous levels of activity in a larval cell lacking said nucleic acid.

24. The method of claim 21, wherein at least one nucleic acid introduced into said larval cell is on an expression vector comprising a transposon and a nucleic acid encoding at least one of said polypeptides.

25. The method of claim 22, wherein at least one nucleic acid introduced into said larval cell is on an expression vector comprising a transposon and a nucleic acid encoding at least one of said polypeptides.

26. The method of claim 23, wherein at least one nucleic acid introduced into said larval cell is on an expression vector comprising a transposon and a nucleic acid encoding at least one of said polypeptides.

27. The transgenic insect cell of claim 1, wherein said polypeptide capable of converting GlcNAc-6-P to ManNAc-6-P is (b) a variant of the polypeptide specified in (a) that contains conservative amino acid substitutions in which GNPE function is retained.

28. The transgenic insect cell of claim 1, wherein said polypeptide capable of converting GlcNAc-6-P to ManNAc-6-P is
- (c) a truncated or fusion variant of the polypeptide specified in (a) or (b) comprising one or more insertions or deletions of amino acids in which GNPE function is retained;
    - wherein each of said one or more insertions or deletions are located between regions that are conserved among
        - (1) the polypeptides specified in (a) or (b); and
        - (2) a polypeptide capable of converting GlcNAc-6-P to ManNAc-6-P which is obtained from a source belonging to the domain Bacteria.

29. The transgenic insect cell of claim 1, wherein said polypeptide capable of converting GlcNAc-6-P to ManNAc-6-P is
- (d) a truncated or fusion variant of the polypeptide specified in (a), (b) or (c) comprising one or more insertions or deletions of amino acids in which GNPE function is retained;
    - wherein each of said one or more insertions or deletions are located at
    - the amino terminus, the carboxy terminus, or both the amino and carboxy termini of
    - the polypeptide specified in (a), (b) or (c).

30. The transgenic Lepidopteran insect larva of claim 4, wherein said polypeptide capable of converting GlcNAc-6-P to ManNAc-6-P is
- (a) said polypeptide comprising SEQ ID NO: 6.

31. The transgenic Lepidopteran insect larva of claim 4, wherein said polypeptide capable of converting GlcNAc-6-P to ManNAc-6-P is
- (b) a variant of the polypeptide specified in (a) that contains conservative amino acid substitutions in which GNPE function is retained.

32. The transgenic Lepidopteran insect larva of claim 4, wherein said polypeptide capable of converting GlcNAc-6-P to ManNAc-6-P is
- (c) a truncated or fusion variant of the polypeptide specified in (a) or (b) comprising one or more insertions or deletions of amino acids in which GNPE function is retained;
    - wherein each of said one or more insertions or deletions are located between regions that are conserved among
        - (1) the polypeptides specified in (a) or (b); and
        - (2) a polypeptide capable of converting GlcNAc-6-P to ManNAc-6-P which is obtained from a source belonging to the domain Bacteria.

33. The transgenic Lepidopteran insect larva of claim 4, wherein said polypeptide capable of converting GlcNAc-6-P to ManNAc-6-P is
- (d) a truncated or fusion variant of the polypeptide specified in (a), (b) or (c) comprising one or more insertions or deletions of amino acids in which GNPE function is retained;
    - wherein each of said one or more insertions or deletions are located at
    - the amino terminus, the carboxy terminus, or both the amino and carboxy termini of
    - the polypeptide specified in (a), (b) or (c).

* * * * *

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Synthetic NanE forward Primer 1

<400> SEQUENCE: 1
gcggccgcac catgtcgtta cttgcacaac                                          30

<210> SEQ ID NO 2
<211> LENGTH: 29
<212> TYPE: DNA
<213> ORGANISM: Artificial Sequence
<220> FEATURE:
<223> OTHER INFORMATION: Synthetic NanE Reverse Primer 1

<400> SEQUENCE: 2
atgcggccgc tcatagcacc gccttttc                                            29

<210> SEQ ID NO 3
<211> LENGTH: 19
<212> TYPE: DNA
<213> ORGANISM: Artificial Sequence
<220> FEATURE:
<223> OTHER INFORMATION: Synthetic NanE Forward Primer 2

<400> SEQUENCE: 3
gcggccgcac catgtcgtt                                                      19

<210> SEQ ID NO 4
<211> LENGTH: 19
<212> TYPE: DNA
<213> ORGANISM: Artificial Sequence
<220> FEATURE:
<223> OTHER INFORMATION: Synthetic NanE Reverse Primer 2

<400> SEQUENCE: 4
atgcggccgc tcatagcac                                                      19

<210> SEQ ID NO 5
<211> LENGTH: 711
<212> TYPE: DNA
<213> ORGANISM: Escherichia coli
<220> FEATURE:
<221> NAME/KEY: misc_feature
<222> LOCATION: (1)..(11)
<223> OTHER INFORMATION: Synthetic region of amplified PCR product
      having a NotI recognition site flanking 5' end of ORF encoding E.
      coli GlcNAc-6-P 2' epimerase
```

<220> FEATURE:
<221> NAME/KEY: CDS
<222> LOCATION: (12)..(701)
<223> OTHER INFORMATION: Open Reading Frame (ORF) encoding E. coli K-12
    substrain MG1655 GlcNAc-6-P 2' epimerase flanked by synthetic
    sequences having NotI restriction endonuclease recognition sites
<220> FEATURE:
<221> NAME/KEY: misc_feature
<222> LOCATION: (702)..(711)
<223> OTHER INFORMATION: Synthetic region of amplified PCR product
    having a NotI recognition site flanking 3' end of ORF encoding E.
    coli GlcNAc-6-P 2' epimerase

<400> SEQUENCE: 5

```
gcggccgcac c atg tcg tta ctt gca caa ttg gat caa aaa atc gct gct        50
            Met Ser Leu Leu Ala Gln Leu Asp Gln Lys Ile Ala Ala
            1               5                   10 aac ggt ggc ctg att gtc tcc tgc cag ccg gtt ccg gac agc ccg ctc          98
Asn Gly Gly Leu Ile Val Ser Cys Gln Pro Val Pro Asp Ser Pro Leu
 15                  20                  25 gat aaa ccc gaa atc gtc gcc gcc atg gca tta gcg gca gaa cag gcg        146
Asp Lys Pro Glu Ile Val Ala Ala Met Ala Leu Ala Ala Glu Gln Ala
 30                  35                  40                  45 ggc gcg gtt gcc att cgc att gaa ggt gtg gca aat ctg caa gcc acg        194
Gly Ala Val Ala Ile Arg Ile Glu Gly Val Ala Asn Leu Gln Ala Thr
                 50                  55                  60 cgt gcg gtg gtg agc gtg ccg att att gga att gtg aaa cgc gat ctg        242
Arg Ala Val Val Ser Val Pro Ile Ile Gly Ile Val Lys Arg Asp Leu
                 65                  70                  75 gag gat tct ccg gta cgc atc acg gcc tat att gaa gat gtt gat gcg        290
Glu Asp Ser Pro Val Arg Ile Thr Ala Tyr Ile Glu Asp Val Asp Ala
             80                  85                  90 ctg gcg cag gcg ggc gcg gac att atc gcc att gac ggc acc gac cgc        338
Leu Ala Gln Ala Gly Ala Asp Ile Ile Ala Ile Asp Gly Thr Asp Arg
         95                  100                 105 ccg cgt ccg gtg cct gtt gaa acg ctg ctg gca cgt att cac cat cac        386
Pro Arg Pro Val Pro Val Glu Thr Leu Leu Ala Arg Ile His His His
110                 115                 120                 125 ggt tta ctg gcg atg acc gac tgc tca acg ccg gaa gac ggc ctg gca        434
Gly Leu Leu Ala Met Thr Asp Cys Ser Thr Pro Glu Asp Gly Leu Ala
                130                 135                 140 tgc caa aag ctg gga gcc gaa att att ggc act acg ctt tct ggc tat        482
Cys Gln Lys Leu Gly Ala Glu Ile Ile Gly Thr Thr Leu Ser Gly Tyr
            145                 150                 155 acc acg cct gaa acg cca gaa gag ccg gat ctg gcg ctg gtg aaa acg        530
Thr Thr Pro Glu Thr Pro Glu Glu Pro Asp Leu Ala Leu Val Lys Thr
            160                 165                 170 ttg agc gac gcc gga tgt cgg gtg att gcc gaa ggg cgt tac aac acg        578
Leu Ser Asp Ala Gly Cys Arg Val Ile Ala Glu Gly Arg Tyr Asn Thr
    175                 180                 185 cct gct cag gcg gcg gat gcg atg cgc cac ggc gcg tgg gcg gtg acg        626
Pro Ala Gln Ala Ala Asp Ala Met Arg His Gly Ala Trp Ala Val Thr
190                 195                 200                 205 gtc ggt tct gca atc acg cgt ctt gag cac att tgt cag tgg tac aac        674
Val Gly Ser Ala Ile Thr Arg Leu Glu His Ile Cys Gln Trp Tyr Asn
                210                 215                 220 aca gcg atg aaa aag gcg gtg cta tga gcggccgcat                         711
Thr Ala Met Lys Lys Ala Val Leu
            225
```

<210> SEQ ID NO 6
<211> LENGTH: 229

```
<212> TYPE: PRT
<213> ORGANISM: Escherichia coli

<400> SEQUENCE: 6

Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
                20                  25                  30

Glu Ile Val Ala Ala Met Ala Leu Ala Ala Glu Gln Ala Gly Ala Val
                35                  40                  45

Ala Ile Arg Ile Glu Gly Val Ala Asn Leu Gln Ala Thr Arg Ala Val
        50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

Ala Gly Ala Asp Ile Ile Ala Ile Asp Gly Thr Asp Arg Pro Arg Pro
                100                 105                 110

Val Pro Val Glu Thr Leu Leu Ala Arg Ile His His His Gly Leu Leu
                115                 120                 125

Ala Met Thr Asp Cys Ser Thr Pro Glu Asp Gly Leu Ala Cys Gln Lys
        130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
                180                 185                 190

Ala Ala Asp Ala Met Arg His Gly Ala Trp Ala Val Thr Val Gly Ser
        195                 200                 205

Ala Ile Thr Arg Leu Glu His Ile Cys Gln Trp Tyr Asn Thr Ala Met
        210                 215                 220

Lys Lys Ala Val Leu
225
```